US008013126B2

(12) United States Patent
Jakobovits et al.

(10) Patent No.: US 8,013,126 B2
(45) Date of Patent: Sep. 6, 2011

(54) 84P2A9: A PROSTATE AND TESTIS SPECIFIC PROTEIN HIGHLY EXPRESSED IN PROSTATE CANCER

(75) Inventors: Aya Jakobovits, Beverly Hills, CA (US); Daniel E. H. Afar, Fremont, CA (US); Pia M. Challita-Eid, Encino, CA (US); Elana Levin, Los Angeles, CA (US); Steve Chappell Mitchell, Gurnee, IL (US); Rene S. Hubert, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 279 days.

(21) Appl. No.: 12/324,707

(22) Filed: Nov. 26, 2008

(65) Prior Publication Data

US 2009/0170191 A1    Jul. 2, 2009

Related U.S. Application Data

(63) Continuation of application No. 09/771,312, filed on Jan. 26, 2001, now Pat. No. 7,510,855.

(60) Provisional application No. 60/178,560, filed on Jan. 26, 2000.

(51) Int. Cl.
C12P 21/08 (2006.01)
C07K 16/00 (2006.01)
C07K 17/00 (2006.01)
C07K 17/14 (2006.01)
A61K 39/395 (2006.01)
A61K 39/00 (2006.01)

(52) U.S. Cl. ............... 530/387.9; 530/387.3; 530/388.1; 530/391.1; 530/391.3; 424/130.1; 424/133.1; 424/134.1; 424/139.1

(58) Field of Classification Search .................. None
See application file for complete search history.

(56) References Cited

FOREIGN PATENT DOCUMENTS

| CN | 1328147 | 12/2001 |
|---|---|---|
| EP | 1 033 401 | 9/2000 |
| EP | 1 074 617 | 2/2001 |
| GB | 2211504 | 7/1989 |
| WO | WO 98/37093 | 8/1998 |
| WO | WO 98/45435 | 10/1998 |
| WO | WO 99/38972 | 8/1999 |
| WO | WO 99/42579 | 8/1999 |
| WO | WO 01/51628 | 7/2001 |
| WO | WO 01/55320 | 8/2001 |
| WO | WO 01/55391 | 8/2001 |
| WO | WO 01/75067 | 10/2001 |
| WO | WO 01/77289 | 10/2001 |
| WO | WO 02/10449 | 2/2002 |
| WO | WO 02/22660 | 3/2002 |
| WO | WO 02/29103 | 4/2002 |
| WO | WO 02/31111 | 4/2002 |
| WO | WO 02/059271 | 8/2002 |

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin binding and mitogenic activities of heparin-binding (acidic fibroblast) growth factor 1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Alberts et al., Molecular Biology of the Cell, $3^{rd}$ ed. (1994) p. 465.
Chen et al., J. Biol. Chem. (1998) 273(28):17618-17625.
Database EMBL, Accession No. AA908961, Apr. 16, 1998, XP002177748.
Database EMBL, Accession No. AK001114, Feb. 22, 2000, XP002177749.
Database EMBL, EBI accession No. aw298059, Jan. 17, 2000.
Fu et al., "Translational regulation of human p53 gene expression," EMBO Journal (1996) 15:4392-4401.
Greenbaum et al., "Comparing protein abundance and mRNA expression levels on a genomic scale," Genome Biology (2003) 4(9):117.1-117.8.
Gura, "Systems for Identifying New Drugs are Often Faulty," Science (1997) 275:1041-1042.
Hirosawa et al., DNA Research (1999) 6:329-336.
Hubert et al., "STEAP: a prostate-specific cell-surface antigen highly expressed in human prostate tumors," PNAS USA (1999) 96(25):14523-14528.
Klein et al., "Progression of metastatic human prostate cancer to androgen independence in immunodeficient SCID mice," Nature Med. (1997) 3:402-408.
Lewin, Genes VI, Oxford Univ. Press, Inc. (1997) Chapter 29.
Mallampalli et al., "Betamethasone modulation of sphingomyelin hydrolysis up-regulates CTP:cholinephosphate cytidylyltransferase activity in adult rat lung," Biochem. J. (1996) 318:333-341.
MGC Project Team, Genome Research (2004) 14:2121-2127.
Morton and Myszka, "Kinetic analysis of macromolecular interactions using surface plasmon resonance biosensors," Methods in Enzymology (1998) 295:268-294.
Muller et al., "BCR first exon sequences specifically activate the BCR/ABL tyrosine kinase oncogene of Philadelphia chromosome-positive human leukemias," Mol. Cell Biol. (1991) 11:1785-1792.
Pemberton et al., "Maspin is an intracellular serpin that partitions into secretory vesicles and is present at the cell surface," J. of Histochemistry and Cytochemistry (1997) 45:1697-1706.
Pinto et al., "Prostate-specific membrane antigen: a novel folate hydrolase in human prostatic carcinoma cells," Clin. Cancer Res. (1996) 2(9):1445-1451.

(Continued)

Primary Examiner — Anne M. Gussow
(74) Attorney, Agent, or Firm — Morrison & Foerster LLP

(57) ABSTRACT

A novel gene (designated 84P2A9) and its encoded protein is described. While 84P2A9 exhibits prostate and testis specific expression in normal adult tissue, it is aberrantly expressed multiple cancers including prostate, testis, kidney, brain, bone, skin, ovarian, breast, pancreas, colon, lymphocytic and lung cancers. Consequently, 84P2A9 provides a diagnostic and/or therapeutic target for cancers, and the 84P2A9 gene or fragment thereof, or its encoded protein or a fragment thereof used to elicit an immune response.

14 Claims, 13 Drawing Sheets

OTHER PUBLICATIONS

Reiter et al., "Prostate stem cell antigen: a cell surface marker overexpressed in prostate cancer," PNAS USA (1998) 95:1735-1740.

Storrie et al., "Isolation of subcellular organelles," Methods Enzymol. (1990) 182:203-225.

Strausberg et al., "Generation and initial analysis of more than 15,000 full-length human and mouse cDNA sequences," PNAS (2002) 99(26):16899-16903.

Su et al., "Surface-epitope masking and expression cloning identifies the human prostate carcinoma tumor antigen gene PCTA-1 a member of the galectin gene family," PNAS USA (1996) 93:7252-7.

Walter et al., "A method for constructing radiation hybrid maps of whole genomes," Nat. Genetics (1994) 7:22.

Weiner, "An Overview of Monoclonal Antibody Therapy of Cancer," Seminars Oncology (1999) 26(4):41-50.

Welch et al., "Use of the Membrane Invasion Culture System (MICS) as a screen for anti-invasive agents," Int. J. Cancer (1989) 43:449-457.

Welford, Opt. Quant. Elect. (1991) 23:1.

Office Action for Canadian Application No. 2,398,064, date mailed on Jul. 7, 2007, 5 pages.

Office Action for Japanese Application No. 2001-554420, date mailed on Dec. 13, 2005.

Response to Office Action for European Application No. 01910358.9, date mailed on Dec. 14, 2006, 4 pages.

European Search Report for EP 08154530.3, mailed Aug. 11, 2008, 5 pages.

* cited by examiner

FIG. 1

```
GATCAAGCTTTTTTTTTTTTTTTTTTTTTTGGATAACAACGATGAGGTTTATTTTTGTCAAAACA
TCCAAGGGAAACATTAATTGTTGTTTGTCAACTGTGAACTTCACACTACATTGTCTAAGGATAGAAAAT
TGATGGGTATCACTCTGTCAGAAAATCCTCACCAAGAAGCCAATTCAAGGAATATGAAATTGACAAGCC
TTTCAAACAAAGATGTGTTCGGACTTCACTGATGCGATGGTAGGTCTTTTGGGTTACAATAGATAGGGA
TGATATAAAACACAATCTTTTCCTGTCTATTCCATTTTAGAAACTGGTGGGTGTGCTCACGTTTGTCTG
GGCATTGCAGCACTGCACACATACATGAATTAAGCAAAGCATCGGAAAGTATTGACACATGAGACTAAA
ATAAATAAGAG
```

FIG. 2-1

```
         11          20          29          38          47          56
5' ATT CGG CAC GAG GTG AAA GTC GCC GGT GCT GTT GTA GTT GGA GTC TGT TCA CGG
   --- --- --- --- --- --- --- --- --- --- --- --- --- --- --- --- --- ---
         65          74          83          92         101         110
   GCC TGA GCT TCG AGG CCA GGC TCC TGG GTG TCG TTA ATG TTC GGG GCC GCC GGG
   --- --- --- --- --- --- --- --- --- --- --- --- --- --- --- --- --- ---
        119         128         137         146         155         164
   CGC CAA CCG ATC GGA GCT CCA GCA GCC GGG AAC AGC TGG CAT TTC AGT AGA ACC
   --- --- --- --- --- --- --- --- --- --- --- --- --- --- --- --- --- ---
        173         182         191         200         209         218
   ATG GAG GAG CTG GTT CAT GAC CTT GTC TCA GCA TTG GAA GAG AGC TCA GAG CAA
   --- --- --- --- --- --- --- --- --- --- --- --- --- --- --- --- --- ---
   M   E   E   L   V   H   D   L   V   S   A   L   E   E   S   S   E   Q 227         236         245         254         263         272
   GCT CGA GGT GGA TTT GCT GAA ACA GGA GAC CAT TCT CGA AGT ATA TCT TGC CCT
   --- --- --- --- --- --- --- --- --- --- --- --- --- --- --- --- --- ---
   A   R   G   G   F   A   E   T   G   D   H   S   R   S   I   S   C   P 281         290         299         308         317         326
   CTG AAA CGC CAG GCA AGG AAA AGG AGA GGG AGA AAA CGG AGG TCG TAT AAT GTG
   --- --- --- --- --- --- --- --- --- --- --- --- --- --- --- --- --- ---
   L   K   R   Q   A  |R   K   R   R|  G  |R   K   R   R|  S   Y   N   V 335         344         353         362         371         380
   CAT CAC CCG TGG GAG ACT GGT CAC TGC TTA AGT GAA GGC TCT GAT TCT AGT TTA
   --- --- --- --- --- --- --- --- --- --- --- --- --- --- --- --- --- ---
   H   H   P   W   E   T   G   H   C   L   S   E   G   S   D   S   S   L 389         398         407         416         425         434
   GAA GAA CCA AGC AAG GAC TAT AGA GAG AAT CAC AAT AAT AAT AAA AAA GAT CAC
   --- --- --- --- --- --- --- --- --- --- --- --- --- --- --- --- --- ---
   E   E   P   S   K   D   Y   R   E   N   H   N   N   N   K   K   D   H 443         452         461         470         479         488
   AGT GAC TCT GAT GAC CAA ATG TTA GTA GCA AAG CGC AGG CCG TCA TCA AAC TTA
   --- --- --- --- --- --- --- --- --- --- --- --- --- --- --- --- --- ---
   S   D   S   D   D   Q   M   L   V   A  |K   R   R   P|  S   S   N   L 497         506         515         524         533         542
   AAT AAT AAT GTT CGA GGG AAA AGA CCT CTA TGG CAT GAG TCT GAT TTT GCT GTG
   --- --- --- --- --- --- --- --- --- --- --- --- --- --- --- --- --- ---
   N   N   N   V   R   G   K   R   P   L   W   H   E   S   D   F   A   V 551         560         569         578         587         596
   GAC AAT GTT GGG AAT AGA ACT CTG CGC AGG AGG AGA AAG GTA AAA CGC ATG GCA
   --- --- --- --- --- --- --- --- --- --- --- --- --- --- --- --- --- ---
   D   N   V   G   N   R   T   L  |R   R   R   K|  V   K   R   M   A 605         614         623         632         641         650
   GTA GAT CTC CCA CAG GAC ATC TCT AAC AAA CGG ACA ATG ACC CAG CCA CCT GAG
   --- --- --- --- --- --- --- --- --- --- --- --- --- --- --- --- --- ---
   V   D   L   P   Q   D   I   S   N   K   R   T   M   T   Q   P   P   E 659         668         677         686         695         704
   GGT TGT AGA GAT CAG GAC ATG GAC AGT GAT AGA GCC TAC CAG TAT CAA GAA TTT
   --- --- --- --- --- --- --- --- --- --- --- --- --- --- --- --- --- ---
   G   C   R   D   Q   D   M   D   S   D   R   A   Y   Q   Y   Q   E   F 713         722         731         740         749         758
   ACC AAG AAC AAA GTC AAA AAA AGA AAG TTG AAA ATA ATC AGA CAA GGA CCA AAA
   --- --- --- --- --- --- --- --- --- --- --- --- --- --- --- --- --- ---
   T   K   N   K   V  |K   K   R   K|  L   K   I   I   R   Q   G   P   K
```

FIG. 2-2

```
          767           776           785           794           803           812
ATC  CAA  GAT  GAA  GGA  GTA  GTT  TTA  CAA  AGT  GAG  GAA  ACG  AAC  CAG  ACC  AAT  AAG
---  ---  ---  ---  ---  ---  ---  ---  ---  ---  ---  ---  ---  ---  ---  ---  ---  ---
 I    Q    D    E    G    V    V    L    Q    S    E    E    T    N    Q    T    N    K 821           830           839           848           857           866
GAC  AAA  ATG  GAA  TGT  GAA  GAG  CAA  AAA  GTC  TCA  GAT  GAG  CTC  ATG  AGT  GAA  AGT
---  ---  ---  ---  ---  ---  ---  ---  ---  ---  ---  ---  ---  ---  ---  ---  ---  ---
 D    K    M    E    C    E    E    Q    K    V    S    D    E    L    M    S    E    S 875           884           893           902           911           920
GAT  TCC  AGC  AGT  CTC  AGC  AGC  ACT  GAT  GCT  GGA  TTG  TTT  ACC  AAT  GAT  GAG  GGA
---  ---  ---  ---  ---  ---  ---  ---  ---  ---  ---  ---  ---  ---  ---  ---  ---  ---
 D    S    S    S    L    S    S    T    D    A    G    L    F    T    N    D    E    G 929           938           947           956           965           974
AGA  CAA  GGT  GAT  GAT  GAA  CAG  AGT  GAC  TGG  TTC  TAC  GAA  AAG  GAA  TCA  GGT  GGA
---  ---  ---  ---  ---  ---  ---  ---  ---  ---  ---  ---  ---  ---  ---  ---  ---  ---
 R    Q    G    D    D    E    Q    S    D    W    F    Y    E    K    E    S    G    G 983           992          1001          1010          1019          1028
GCA  TGT  GGT  ATC  ACT  GGA  GTT  GTG  CCC  TGG  TGG  GAA  AAG  GAA  GAT  CCT  ACT  GAG
---  ---  ---  ---  ---  ---  ---  ---  ---  ---  ---  ---  ---  ---  ---  ---  ---  ---
 A    C    G    I    T    G    V    V    P    W    W    E    K    E    D    P    T    E 1037          1046          1055          1064          1073          1082
CTA  GAC  AAA  AAT  GTA  CCA  GAT  CCT  GTC  TTT  GAA  AGT  ATC  TTA  ACT  GGT  TCT  TTT
---  ---  ---  ---  ---  ---  ---  ---  ---  ---  ---  ---  ---  ---  ---  ---  ---  ---
 L    D    K    N    V    P    D    P    V    F    E    S    I    L    T    G    S    F 1091          1100          1109          1118          1127          1136
CCC  CTT  ATG  TCA  CAC  CCA  AGC  AGA  AGA  GGT  TTC  CAA  GCT  AGA  CTC  AGT  CGC  CTT
---  ---  ---  ---  ---  ---  ---  ---  ---  ---  ---  ---  ---  ---  ---  ---  ---  ---
 P    L    M    S    H    P    S    R    R    G    F    Q    A    R    L    S    R    L 1145          1154          1163          1172          1181          1190
CAT  GGA  ATG  TCT  TCA  AAG  AAT  ATT  AAA  AAA  TCT  GGA  GGG  ACT  CCA  ACT  TCA  ATG
---  ---  ---  ---  ---  ---  ---  ---  ---  ---  ---  ---  ---  ---  ---  ---  ---  ---
 H    G    M    S    S    K    N    I    K    K    S    G    G    T    P    T    S    M 1199          1208          1217          1226          1235          1244
GTA  CCC  ATT  CCT  GGC  CCA  GTG  GGT  AAC  AAG  AGA  ATG  GTT  CAT  TTT  TCC  CCG  GAT
---  ---  ---  ---  ---  ---  ---  ---  ---  ---  ---  ---  ---  ---  ---  ---  ---  ---
 V    P    I    P    G    P    V    G    N    K    R    M    V    H    F    S    P    D 1253          1262          1271          1280          1289          1298
TCT  CAT  CAC  CAT  GAC  CAT  TGG  TTT  AGC  CCT  GGG  GCT  AGG  ACA  GAG  CAT  GAC  CAG
---  ---  ---  ---  ---  ---  ---  ---  ---  ---  ---  ---  ---  ---  ---  ---  ---  ---
 S    H    H    H    D    H    W    F    S    P    G    A    R    T    E    H    D    Q 1307          1316          1325          1334          1343          1352
CAT  CAG  CTT  CTG  AGA  GAT  AAT  CGA  GCT  GAA  AGA  GGA  CAC  AAG  AAA  AAT  TGT  TCT
---  ---  ---  ---  ---  ---  ---  ---  ---  ---  ---  ---  ---  ---  ---  ---  ---  ---
 H    Q    L    L    R    D    N    R    A    E    R    G    H    K    K    N    C    S 1361          1370          1379          1388          1397          1406
GTG  AGA  ACA  GCC  AGC  AGG  CAA  ACA  AGC  ATG  CAT  TTA  GGA  TCC  TTA  TGC  ACG  GGA
---  ---  ---  ---  ---  ---  ---  ---  ---  ---  ---  ---  ---  ---  ---  ---  ---  ---
 V    R    T    A    S    R    Q    T    S    M    H    L    G    S    L    C    T    G 1415          1424          1433          1442          1451          1460
GAT  ATC  AAA  CGG  AGA  AGA  AAA  GCT  GCA  CCT  TTG  CCT  GGA  CCT  ACT  ACT  GCA  GGA
---  ---  ---  ---  ---  ---  ---  ---  ---  ---  ---  ---  ---  ---  ---  ---  ---  ---
 D    I   │K    R    R    R    K│   A    A    P    L    P    G    P    T    T    A    G
```

FIG. 2-3

```
         1469        1478        1487        1496        1505        1514
TTT GTA GGT GAA AAT GCC CAG CCA ATC CTA GAA AAT AAT ATT GGA AAC CGA ATG
--- --- --- --- --- --- --- --- --- --- --- --- --- --- --- --- ---
 F   V   G   E   N   A   Q   P   I   L   E   N   N   I   G   N   R   M 1523        1532        1541        1550        1559        1568
CTT CAG AAT ATG GGC TGG ACG CCT GGG TCA GGC CTT GGA CGA GAT GGC AAG GGG
--- --- --- --- --- --- --- --- --- --- --- --- --- --- --- --- ---
 L   Q   N   M   G   W   T   P   G   S   G   L   G   R   D   G   K   G 1577        1586        1595        1604        1613        1622
ATC TCT GAG CCA ATT CAA GCC ATG CAG AGG CCA AAG GGA TTA GGA CTT GGA TTT
--- --- --- --- --- --- --- --- --- --- --- --- --- --- --- --- ---
 I   S   E   P   I   Q   A   M   Q   R   P   K   G   L   G   L   G   F 1631        1640        1649        1658        1667        1676
CCT CTA CCA AAA AGT ACT TCC GCA ACT ACT ACC CCC AAT GCA GGA AAA TCC GCC
--- --- --- --- --- --- --- --- --- --- --- --- --- --- --- --- ---
 P   L   P   K   S   T   S   A   T   T   T   P   N   A   G   K   S   A 1685        1694        1703        1712        1721        1730
TAA GAA AAG CAA AGA AGA AAT GTT TTA CAG ACT TTA TTC ACT ATG TCC CAT TGT
--- --- --- --- --- --- --- --- --- --- --- --- --- --- --- --- ---
 *

1739        1748        1757        1766        1775        1784
TCT AAA ATG ATA ACA TGA CTT CTG TTT TTG AAG CAA AAA TCT ACA TTG CCT CAA
--- --- --- --- --- --- --- --- --- --- --- --- --- --- --- --- ---
         1793        1802        1811        1820        1829        1838
ACA CAT CAC TCT AGC TTC CTT ACT GCA TAC AGT CCT GCC ATA GTG AGA GAA ATG
--- --- --- --- --- --- --- --- --- --- --- --- --- --- --- --- ---
         1847        1856        1865        1874        1883        1892
GGA TTT CAT CAC AAT TCA TGG TGC TAA AAT GAA AAC CTC TGC ACT TTA ATT TTT
--- --- --- --- --- --- --- --- --- --- --- --- --- --- --- --- ---
         1901        1910        1919        1928        1937        1946
TTC AGT AAT TTC CAG CTA TTT CTA GGT ATA AAG AGC AGC TCG TTT CTC TTA TTT
--- --- --- --- --- --- --- --- --- --- --- --- --- --- --- --- ---
         1955        1964        1973        1982        1991        2000
ATT TTA GTC TCA TGT GTC AAT ACT TTC CGA TGC TTT GCT TAA TTC ATG TAT GTG
--- --- --- --- --- --- --- --- --- --- --- --- --- --- --- --- ---
         2009        2018        2027        2036        2045        2054
TGC AGT GCT GCA ATG CCC AGA CAA ACG TGA GCA CAC CCA CCA GTT TCT AAA ATG
--- --- --- --- --- --- --- --- --- --- --- --- --- --- --- --- ---
         2063        2072        2081        2090        2099        2108
GAA TAG ACA GGA AAA GAT TGT GTT TTA TAT CAT CCC TAT CTA TTG TAA CCC AAA
--- --- --- --- --- --- --- --- --- --- --- --- --- --- --- --- ---
         2117        2126        2135        2144        2153        2162
AGA CCT ACC ATC GCA TCA GTG AAG TCC GAA CAC ATC TTT GTT TGA AAG GCT TGT
--- --- --- --- --- --- --- --- --- --- --- --- --- --- --- --- ---
         2171        2180        2189        2198        2207        2216
CAA TTT CAT ATT CCT TGA ATT GGC TTC TTG GTG AGG ATT TTC TGA CAG AGT GAT
--- --- --- --- --- --- --- --- --- --- --- --- --- --- --- --- ---
         2225        2234        2243        2252        2261        2270
ACC CAT CAA TTT TCT ATC CTT AGA CAA TGT AGT GTG AAG TTC ACA GTT GAC AAA
--- --- --- --- --- --- --- --- --- --- --- --- --- --- --- --- ---
         2279        2288        2297        2306        2315        2324
CAA CAA TTA ATG TTT CCC TTG GAT GTT TTG ACA AAA ATA AAC CTC ATC GTT GTT
--- --- --- --- --- --- --- --- --- --- --- --- --- --- --- --- ---
         2333        2342
ATC ACC AAA AAA AAA AAA AAA AA 3'
--- --- --- --- --- --- --- --
```

FIG. 3A

```
  4 MDELVHDLASALEQTSEQNKLG--ELWEEMALSPRQQRRQLRKRRGRKRRS-DFTHLAEH
  1 MEELVHDLVSALEESSEQARGGFAETGDHSRSISCPLKRQARKRRGRKRRSYNVHHPWET
    * ****** ****  ***   *  *              ** **********   *  *

61 TCCYSEASESSLDEATKDCREVAPVT--NFSDSDDTM-VAKRHPA--LNAIVKSKQHSWH
 61 GHCLSEGSDSSLEEPSKDYRENHNNNKKDESDSDDQMLVAKRRPSSNLNNNVRGKRPLWH
      *  ** *  ***  *   **  **         *****  ****  *   **  *   **

116 ESDSFTENAPCRPLRRRRKVKRVTSEVAASLQQKLKVSDWSYERGCRFKSAKKQRLSRWK
121 ESDFAVDNVGNRTLRRRRKVKRMAVDLPQDISNKRTMT--QPPEGCRDQDMDSDRAYQYQ
    ***      *    * *********   *               ***            *

176 ENTPWTSSGH-------GLCESAENRTFLSKTGRKERMECETDEQKQGSDENMSECETSS
179 EFTKNKVKKRKLKIIRQGPKIQDEGVVLESEETNQTNKDKMECEEQKVSDELMSESDSSS
    * *                  *       *      *       *       *** ***    **

229 VCSSSDTGLFINDEGRQGDDEQSDWFYEGECVPGFTVPNLLPKWAPDHCSEVERM--DSG
239 L-SSTDAGLFINDEGRQGDDEQSDWFYEKESGGACGITGVVPWWEKEDPTELDKNVPDPV
     ** *  ********************** *         *  *     *        *

287 LDKFSDSTFLLPSRPAQRGYHTRLNRLPGAAARCLRK
298 FESILTGSFPLMSHPSRRGFQARLSRLHGMSSKNIKK
     *  *  * **   **  ** ** *           *
```

FIG. 3B

```
744 SNIGNKMLQAMGWREGSGLGRKCQGITAPIEAQVRLKGAGLG
444 NNIGNRMLQNMGWTPGSGLGRDGKGISEPIQAMQRPKGLGLG
    **** *** *** ******   **  ** *  * ** ***
```

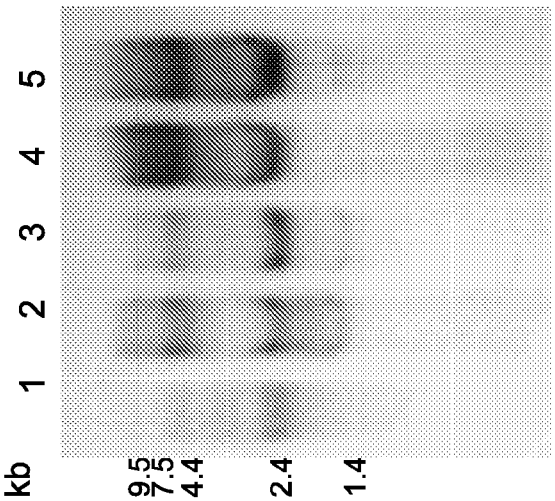
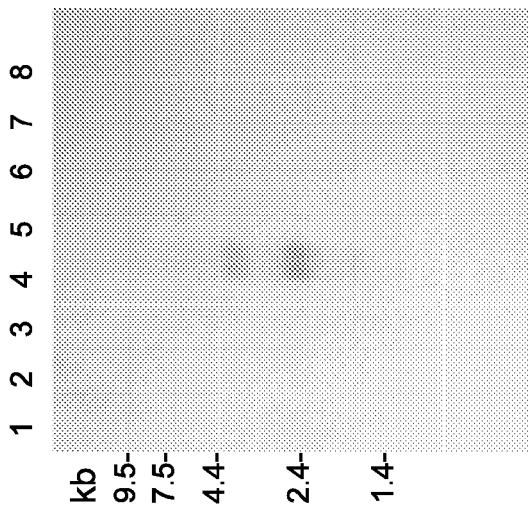
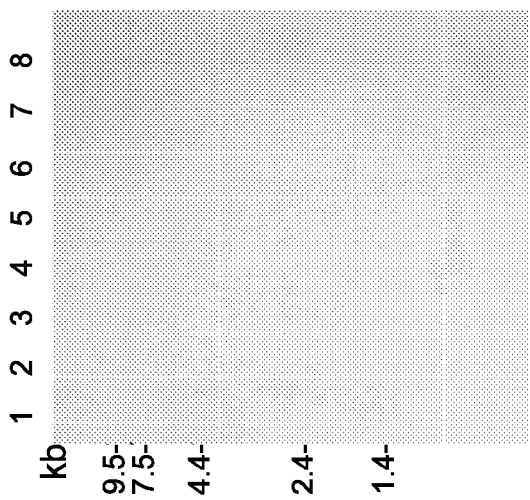
FIG. 4A
FIG. 4B
FIG. 4C

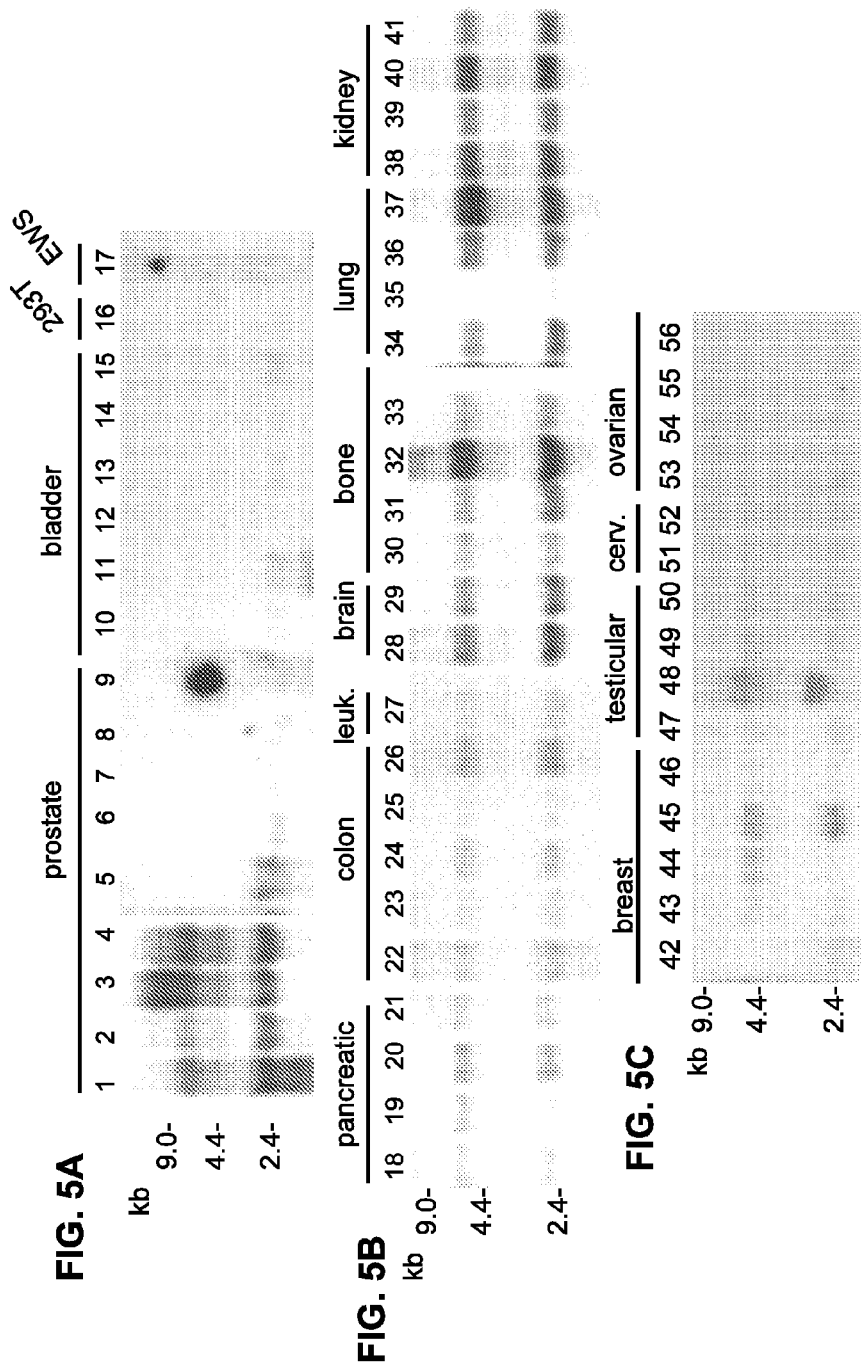

84P2A9: A PROSTATE AND TESTIS SPECIFIC PROTEIN HIGHLY EXPRESSED IN PROSTATE CANCER

CROSS-REFERENCE TO RELATED APPLICATIONS

This application is a continuation of U.S. patent application Ser. No. 09/771,312, filed Jan. 26, 2001 now U.S. Pat. No. 7,510,855, now allowed, which claims the benefit of U.S. provisional patent application No. 60/178,560, filed Jan. 26, 2000, the entire contents of which are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 511582000101Seqlist.txt | Feb. 10, 2009 | 84,549 bytes |

FIELD OF THE INVENTION

The invention described herein relates to a novel gene and its encoded protein, termed 84P2A9, and to diagnostic and therapeutic methods and compositions useful in the management of various cancers that express 84P2A9, particularly prostate cancers.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein, et al., 1997, *Nat. Med.* 3:402). More recently identified prostate cancer markers include PCTA-1 (Su, et al., 1996, *Proc. Natl. Acad. Sci. USA* 93: 7252), prostate-specific membrane (PSM) antigen (Pinto, et al., *Clin Cancer Res* 1996 September; 2(9): 1445-51), STEAP (*Proc Natl Acad Sci USA*. 1999 Dec. 7; 96(25):14523-8) and prostate stem cell antigen (PSCA) (Reiter, et al., 1998, *Proc. Natl. Acad. Sci. USA* 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to a novel, largely prostate and testis-related gene, designated 84P2A9, that is over-expressed in multiple cancers including prostate, testis, kidney, brain, bone, skin, ovarian, breast, pancreas, colon, lymphocytic and lung cancers. Northern blot expression analysis of 84P2A9 gene expression in normal tissues shows a highly prostate and testis-related expression pattern in adult tissues. Analysis of 84P2A9 expression in normal prostate and prostate tumor xenografts shows over-expression in LAPC-4 and LAPC-9 prostate tumor xenografts, with the highest expression in LAPC-9. The nucleotide (SEQ ID NO:1) and amino acid (SEQ ID NO:2) sequences of 84P2A9 are shown in FIG. 2. Portions of the 84P2A9 amino acid sequence show some homologies to ESTs in the dbEST database. The prostate and testis-related expression profile of 84P2A9 in normal adult tissues, combined with the over-expression observed in prostate tumor xenografts, shows that 84P2A9 is aberrantly over-expressed in at least some cancers, and thus serves as a useful diagnostic and/or therapeutic target for cancers such as prostate, testis, kidney, brain, bone, skin, ovarian, breast, pancreas, colon, lymphocytic and lung cancers (see, e.g., FIGS. 4-8).

The invention provides polynucleotides corresponding or complementary to all or part of the 84P2A9 genes, mRNAs, and/or coding sequences, preferably in isolated form, including polynucleotides encoding 84P2A9 proteins and fragments of 4, 5, 6, 7, 8, 9, 10, 11, 12, 13, 14, 15 or more amino acids, DNA, RNA, DNA/RNA hybrids, and related molecules, polynucleotides or oligonucleotides complementary or having at least a 90% homology to the 84P2A9 genes or mRNA sequences or parts thereof, and polynucleotides or oligonucleotides that hybridize to the 84P2A9 genes, mRNAs, or to 84P2A9-encoding polynucleotides. Also provided are means for isolating cDNAs and the genes encoding 84P2A9. Recombinant DNA molecules containing 84P2A9 polynucleotides, cells transformed or transduced with such molecules, and host-vector systems for the expression of 84P2A9 gene products are also provided. The invention further provides antibodies that bind to 84P2A9 proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of 84P2A9 polynucleotides and proteins in various biological samples, as well as methods for identifying cells that express 84P2A9. A typical embodiment of this invention provides methods for monitoring 84P2A9 gene products in a tissue or hematology sample having or suspected of having some form of growth disregulation such as cancer.

The invention further provides various immunogenic or therapeutic compositions and strategies for treating cancers that express 84P2A9 such as prostate cancers, including therapies aimed at inhibiting the transcription, translation, processing or function of 84P2A9 as well as cancer vaccines.

BRIEF DESCRIPTION OF THE FIGURES

FIG. 1 shows the 84P2A9 suppression subtractive hybridization (SSH) DNA sequence of about 425 nucleotides in length (SEQ ID NO:3). This sequence was identified in comparisons of cDNAs from various androgen dependent and androgen independent LAPC xenografts.

FIG. 2 shows the nucleotide (SEQ ID NO:1) and amino acid (SEQ ID NO:2) sequences of 84P2A9. See Example 2, infra. The sequence surrounding the start ATG (AAC ATG G) (SEQ ID NO:4) exhibits a Kozak sequence (A at position −3, and G at position +1). The start methionine with Kozak sequence is indicated in bold, the nuclear localization signals are boxed.

FIGS. 3A and 3B show the amino acid sequence alignment of 84P2A9 (SEQ ID NO:2) with KIAA1552 (SEQ ID NO:5) and LUCA15 (SEQ ID NO:6). FIG. 3A shows that the 84P2A9 protein sequence (bottom line) has some homology to the human brain protein KIAA1152 (39.5% identity over a 337 amino acid region, Score: 407.0; Gap frequency: 5.9%). FIG. 3B shows that the 84P2A9 protein sequence (bottom line) contains a domain that is homologous to a portion of the LUCA15 tumor suppressor protein (64.3% identity over a 42 amino acid region, Score: 138.0; Gap frequency: 0.0%).

FIGS. 4A-4C show the Northern blot analysis of the restricted 84P2A9 expression in various normal human tissues (using the 84P2A9 SSH fragment as a probe) and LAPC xenografts. Two multiple tissue northern blots (Clontech) (FIGS. 4A and 4B) and a xenograft northern blot (FIG. 4C) were probed with the 84P2A9 SSH fragment. Lanes 1-8 in FIG. 4A consist of mRNA from heart, brain, placenta, lung, liver, skeletal muscle, kidney and pancreas respectively. Lanes 1-8 in FIG. 4B consist of total RNA from spleen, thymus, prostate, testis, ovary, small intestine, colon and leukocytes respectively. Lanes 1-5 in FIG. 4C consist of mRNA from prostate, LAPC-4 AD, LAPC-4 AI, LAPC-9 AD and LAPC-9 AI respectively. Size standards in kilobases (kb) are indicated on the side. Each lane contains 2 μg of mRNA for the normal tissues and 10 μg of total RNA for the xenograft tissues. The results show the expression of 84P2A9 in testis and prostate and the LAPC xenografts.

FIGS. 5A-5C show the Northern blot analysis of 84P2A9 expression in prostate and multiple cancer cell lines. Lanes 1-56 show expression in LAPC-4 AD, LAPC4 AI, LAPC-9 AD, LAPC-9 AI, LNCaP, PC-3, DU145, TsuPr1, LAPC-4 CL, HT1197, SCaBER, UM-UC-3, TCCSUP, J82, 5637, 293T, RD-ES, PANC-1, BxPC-3, HPAC, Capan-1, SK-CO-1, CaCo-2, LoVo, T84, Colo-205, KCL 22, PFSK-1, T98G, SK-ES-1, HOS, U2-OS, RD-ES, CALU-1, A427, NCI-H82, NCI-H146, 769-P, A498, CAKI-1, SW839, BT20, CAMA-1, DU4475, MCF-7, MDA-MB-435s, NTERRA-2, NCCIT, TERA-1, TERA-2, A431, HeLa, OV-1063, PA-1, SW626 and CAOV-3 respectively. High levels of 84P2A9 expression were detected in brain (PFSK-1, T98G), bone (HOS, U2-OS), lung (CALU-1, NCI-H82, NCI-H146), and kidney (769-P, A498, CAKI-1, SW839) cancer cell lines. Moderate expression levels were detected in several pancreatic (PANC-1, BxPC-3, HPAC, CAPAN-1), colon (SK-CO-1, CACO-2, LOVO, COLO-205), bone (SK-ES-1, RD-ES), breast (MCF-7, MDA-MB-435s) and testicular cancer (NCCIT) cell lines.

Expression was seen in kidney cancers, breast cancers, prostate cancers, lung cancers, stomach cancers, colon cancers, cervical cancers and rectum cancers. 84P2A9 Was also found to be highly expressed in a panel of cancer cell lines, specially the MOLT-4 lymphoblastic leukemia and the A549 lung carcinoma cell lines. The expression detected in normal adjacent tissues (isolated from diseased tissues) but not in normal tissues, isolated from healthy donors, can indicate that these tissues are not fully normal and that 84P2A9 can be expressed in early stage tumors.

Figure 10:
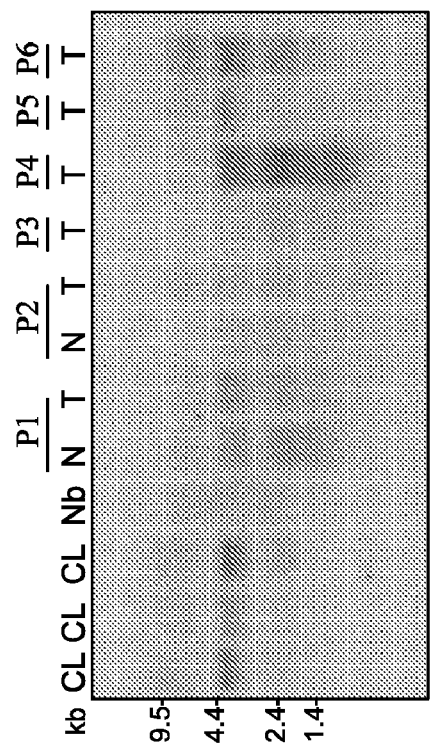

FIG. 10 shows the expression of 84P2A9 in bladder cancer patient specimens. Expression of 84P2A9 was seen in 4 bladder cancer patient specimens tested and in three bladder cell lines (CL), UM-UC-3 (lane 1), J82 (lane 2) and SCABER (lane 3). RNA was isolated from normal bladder (Nb), bladder tumors (I) and their adjacent normal tissues (N) obtained from 6 bladder cancer patients (P). Tumor from P1 is transitional carcinoma, grade 4; P2 is invasive squamous carcinoma; P3 is transitional carcinoma, grade 3; P4 is non-invasive papillary carcinoma, grade 1/3; P5 is papillary carcinoma, grade 3/3; and P6 is transitional carcinoma, grade 3/2. Northern analysis was performed using 10 μg of total RNA for each sample.

Figure 11:
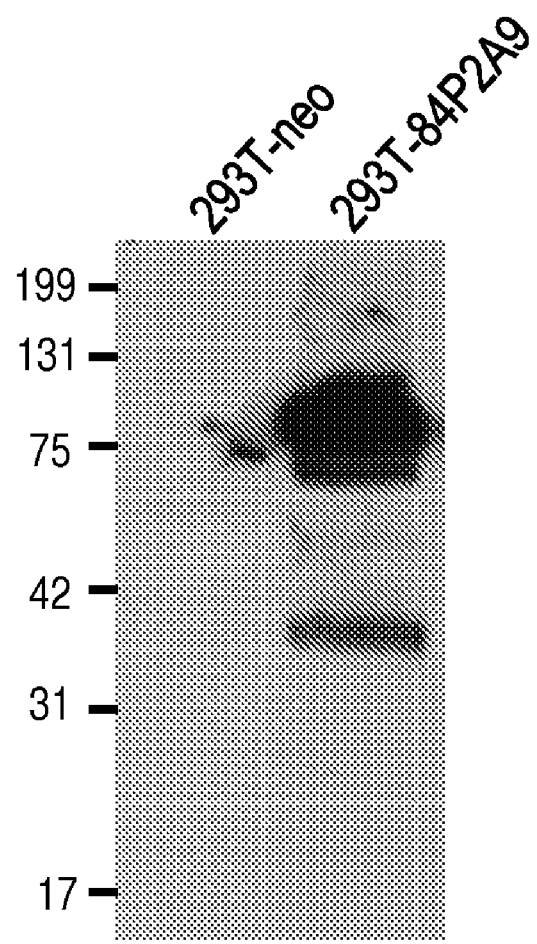

FIG. 11 shows the expression of 84P2A9 protein in 293T cells. 293T Cells were transiently transfected with either pCDNA3.1 V5-HIS epitope tagged 84P2A9 plasmid or with empty control vector and harvested 2 days later. Cells were lysed in SDS-PAGE sample buffer and lysates were separated on a 10-20% SDS-PAGE gel and then transferred to nitrocellulose. The blot was blocked in Tris-buffered saline (TBS)+ 2% non-fat milk and then probed with a 1:3,000 dilution of murine anti-V5 monoclonal Ab (Invitrogen) in TBS+0.15% Tween-20+1% milk. The blot was washed and then incubated with a 1:4,000 dilution of anti-mouse IgG-HRP conjugate secondary antibody. Following washing, anti-V5 epitope immunoreactive bands were developed by enhanced chemiluminescence and visualized by exposure to autoradiographic film. Indicated by arrow is a specific anti-V5 immunoreactive band of approximately 87 Kd that corresponds to expression of the epitope-tagged 84P2A9 protein in the transfected cells.

DETAILED DESCRIPTION OF THE INVENTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are generally well understood and commonly employed using conventional methodology by those skilled in the art, such as, for example, the widely utilized molecular cloning methodologies described in Sambrook, et al., *Molecular Cloning: A Laboratory Manual* 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

DEFINITIONS

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

The term "antibody" is used in the broadest sense. Therefore an "antibody" can be naturally occurring or man made such as monoclonal antibodies produced by conventional hybridoma technology. Anti-84P2A9 antibodies comprise monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region. In one embodiment it specifically covers single anti-84P2A9 antibody (including agonist, antagonist and neutralizing antibodies) and anti-84P2A9 antibody compositions with polyepitopic specificity. The term "monoclonal antibody" as used herein refers to an antibody obtained from a population of substantially homogeneous antibodies, i.e., the antibodies comprising the population are identical except for possible naturally-occurring mutations that are present in minor amounts.

The term "cytotoxic agent" as used herein refers to a substance that inhibits or prevents the function of cells and/or causes destruction of cells. The term is intended to include radioactive isotopes (e.g., $^{211}At$, $^{131}I$, $^{125}I$, $^{90}Y$, $^{186}Re$, $^{188}Re$, $^{153}Sm$, $^{212}Bi$, $^{32}P$ and radioactive isotopes of Lu), chemotherapeutic agents, and toxins such as small molecule toxins or enzymatically active toxins of bacterial, fungal plant or animal origin, including fragments and/or variants thereof.

As used herein, the terms "hybridize", "hybridizing", "hybridizes" and the like, used in the context of polynucleotides, are meant to refer to conventional hybridization conditions, preferably such as hybridization in 50% formamide/ 6×SSC/0.1% SDS/100 μg/ml ssDNA, in which temperatures for hybridization are above 37° C. and temperatures for washing in 0.1×SSC/0.1% SDS are above 55° C.

As used herein, a polynucleotide is said to be "isolated" when it is substantially separated from contaminant polynucleotides that correspond or are complementary to genes other than the 84P2A9 gene or that encode polypeptides other than 84P2A9 gene product or fragments thereof. A skilled artisan can readily employ nucleic acid isolation procedures to obtain an isolated 84P2A9 polynucleotide.

As used herein, a protein is said to be "isolated" when physical, mechanical or chemical methods are employed to remove the 84P2A9 protein from cellular constituents that are normally associated with the protein. A skilled artisan can readily employ standard purification methods to obtain an isolated 84P2A9 protein.

The term "mammal" as used herein refers to any mammal classified as a mammal, including mice, rats, rabbits, dogs, cats, cows, horses and humans. In one preferred embodiment of the invention, the mammal is a mouse. In another preferred embodiment of the invention, the mammal is a human.

As used herein, the terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation, and approximately half of these patients die within 6 months after developing androgen refractory status. The most common site for prostate cancer metastasis is bone. Prostate cancer bone metastases are often characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

"Moderately stringent conditions" are described by, identified but not limited to, those in Sambrook, et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising; 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc., as necessary to accommodate factors such as probe length and the like.

As used herein "motif" as in biological motif of an 84P2A9-realted protein, refers to any set of amino acids forming part of the primary sequence of a protein, either contiguous or capable of being aligned to certain positions that are generally invariant or conserved, that is associated with a particular function or modification (e.g., that is phosphorylated, glycosylated or amidated).

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". As discussed herein, an polynucleotide can comprise a nucleotide sequence disclosed herein wherein thymidine (T) (as shown for example in SEQ ID NO:1) can also be uracil (U). This description pertains to the differences between the chemical structures of DNA and RNA, in particular the observation that one of the four major bases in RNA is uracil (U) instead of thymidine (I).

As used herein, the term "polypeptide" means a polymer of at least about 4, 5, 6, 7, or 8 amino acids. Throughout the specification, standard three letter or single letter designations for amino acids are used. In the art, this term if often used interchangeably with "peptide".

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel, et al., *Current Protocols in Molecular Biology*, Wiley Interscience Publishers, (1995).

"Stringent conditions" or "high stringency conditions", as defined herein, are identified by, but not limited to, those that (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×D Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, the 84P2A9 gene and protein is meant to include the 84P2A9 genes and proteins specifically described herein and the genes and proteins corresponding to other 84P2A9 encoded proteins or peptides and structurally similar variants of the foregoing. Such other 84P2A9 peptides and variants will generally have coding sequences that are highly homologous to the 84P2A9 coding sequence, and preferably share at least about 50% amino acid homology (using BLAST criteria) and preferably 50%, 60%, 70%, 80%, 90% or more nucleic acid homology, and at least about 60% amino acid homology (using BLAST criteria), more preferably sharing 70% or greater homology (using BLAST criteria).

The 84P2A9-related proteins of the invention include those specifically identified herein, as well as allelic variants, conservative substitution variants and homologs that can be isolated/generated and characterized without undue experimentation following the methods outlined herein or are readily available in the art Fusion proteins that combine parts of different 84P2A9 proteins or fragments thereof, as well as fusion proteins of an 84P2A9 protein and a heterologous polypeptide are also included. Such 84P2A9 proteins are collectively referred to as the 84P2A9-related proteins, the proteins of the invention, or 84P2A9. As used herein, the term "84P2A9-related polypeptide" refers to a polypeptide fragment or an 84P2A9 protein sequence of 4, 5, 6, 7, 8, 9, 10, 11, 12, 13, 14, 15 or more ammo acids Structure and Expression of 84P2A9

As discussed in detail below, experiments with the LAPC-4 AD xenograft in male SCID mice have resulted in the identification of genes that are involved in the progression of androgen dependent (AD) prostate cancer to androgen independent (AI) cancer. Briefly, mice that harbored LAPC-4 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually such tumors develop an AI phenotype and start growing again in the castrated males. Tumors were harvested at different time points after castration to identify genes that are turned on or off during the transition to androgen independence.

Suppression subtractive hybridization (SSH) (Diatchenko, et al., 1996, *PNAS* 93:6025) was then used to identify novel genes, such as those that are overexpressed in prostate cancer, by comparing cDNAs from various androgen dependent and androgen independent LAPC xenografts. This strategy resulted in the identification of novel genes exhibiting tissue and cancer specific expression. One of these genes, designated 84P2A9, was identified from a subtraction where cDNA derived from an LAPC-4 AD tumor, 3 days post-castration, was subtracted from cDNA derived from an LAPC-4 AD tumor grown in an intact male. The SSH DNA sequence of about 425 bp (FIG. 1) is novel and exhibits homology only to expressed sequence tags (ESTs) in the dbEST database.

84P2A9 encodes a putative nuclear protein that exhibits prostate and testis-related expression. The initial characterization of 84P2A9 indicates that it is aberrantly expressed multiple cancers including prostate, testis, kidney, brain, bone, skin, ovarian, breast, pancreas, colon, lymphocytic and lung cancers. The expression of 84P2A9 in prostate cancer provides evidence that this protein has a functional role in tumor progression. It is possible that 84P2A9 functions as a transcription factor involved in activating genes involved in tumorigenesis or repressing genes that block tumorigenesis.

As is further described in the Examples that follow, the 84P2A9 genes and proteins have been characterized using a number of analytical approaches. For example, analyses of nucleotide coding and amino acid sequences were conducted in order to identify potentially related molecules, as well as recognizable structural domains, topological features, and other elements within the 84P2A9 mRNA and protein structures. Northern blot analyses of 84P2A9 mRNA expression were conducted in order to establish the range of normal and cancerous tissues expressing 84P2A9 message.

A full length 84P2A9 cDNA clone (clone 1) of 2345 base pairs (SEQ ID NO:1) was cloned from an LAPC-4 AD cDNA library (Lambda ZAP Express, Stratagene) (FIG. 2). The cDNA encodes an open reading frame (ORF) of 504 amino acids (SEQ ID NO:2). Sequence analysis revealed the presence of six potential nuclear localization signals and is predicted to be nuclear using the PSORT program. The protein sequence has some homology to a human brain protein KIAA1152 (SEQ ID NO:5) (39.5% identity over a 337 amino acid region), and contains a domain that is homologous to the LUCA15 tumor suppressor protein (SEQ ID NO:6) (64.3% identity over a 42 amino acid region) (GenBank Accession #P52756) (FIG. 3).

84P2A9 expression is prostate and testis-related in normal adult human tissues, but is also expressed in certain cancers, including prostate, testis, kidney, brain, bone, skin, ovarian, breast, pancreas, colon, lymphocytic and lung cancers (see, e.g., FIGS. 4-8). Human prostate tumor xenografts originally derived from a patient with high grade metastatic prostate cancer express high levels of 84P2A9 (FIG. 4).

As disclosed herein, 84P2A9 exhibits specific properties that are analogous to those found in a family of genes whose polynucleotides, polypeptides, reactive cytotoxic T cells (CTL), helper T cells (HTL) and anti-polypeptide antibodies are used in well known diagnostic assays directed to examining conditions associated with dysregulated cell growth such as cancer, in particular prostate cancer (see, e.g., both its highly specific pattern of tissue expression as well as its overexpression in prostate cancers as described for example in Example 3). The best known member of this class is PSA, the archetypal marker that has been used by medical practitioners for years to identify and monitor the presence of prostate cancer (see, e.g., Merrill, et al., *J. Urol.* 163(2): 503-5120 (2000); Polascik, et al., *J. Urol.* August; 162(2): 293-306 (1999) and Fortier, et al., *J. Nat. Cancer Inst.* 91(19): 1635-1640 (1999)). A variety of other diagnostic markers are also used in this context including p53 and K-ras (see, e.g., Tulchinsky, et al., *Int J Mol Med* 1999 July; 4(1):99-102 and Minimoto, et al., *Cancer Detect Prev* 2000; 24(1):1-12). Therefore, this disclosure of the 84P2A9 polynucleotides and polypeptides (as well as the 84P2A9 polynucleotide probes and anti-84P2A9 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 84P2A9 polynucleotides, polypeptides and antibodies described herein are analogous to those methods from well established diagnostic assays which employ PSA polynucleotides, polypeptides and antibodies. For example, just as PSA polynucleotides are used as probes (for example in Northern analysis, see, e.g., Sharief, et al., *Biochem. Mol. Biol. Int.* 33(3):567-74 (1994)) and primers (for example in PCR analysis, see, e.g., Okegawa, et al., *J. Urol.* 163(4): 1189-1190 (2000)) to observe the presence and/or the level of PSA mRNAs in methods of monitoring PSA overexpression or the metastasis of prostate cancers, the 84P2A9 polynucleotides described herein can be utilized in the same way to detect 84P2A9 overexpression or the metastasis of prostate and other cancers expressing this gene. Alternatively, just as PSA polypeptides are used to generate antibodies specific for PSA which can then be used to observe the presence and/or the level of PSA proteins in methods of monitoring PSA protein overexpression (see, e.g., Stephan, et al., *Urology* 55(4):560-3 (2000)) or the metastasis of prostate cells (see, e.g., Alanen, et al., *Pathol. Res. Pract.* 192(3):233-7 (1996)), the 84P2A9 polypeptides described herein can be utilized to generate antibodies for use in detecting 84P2A9 overexpression or the metastasis of prostate cells and cells of other cancers expressing this gene.

Specifically, because metastases involves the movement of cancer cells from an organ of origin (such as the testis or prostate gland, etc.) to a different area of the body (such as a lymph node), assays which examine a biological sample for the presence of cells expressing 84P2A9 polynucleotides and/or polypeptides can be used to provide evidence of metastasis. For example, when a biological sample from tissue that does not normally contain 84P2A9 expressing cells (lymph node) is found to contain 84P2A9 expressing cells such as the 84P2A9 expression seen in LAPC4 and LAPC9, xenografts isolated from lymph node and bone metastasis, respectively, this finding is indicative of metastasis.

Alternatively 84P2A9 polynucleotides and/or polypeptides can be used to provide evidence of cancer, for example, when a cells in biological sample that do not normally express 84P2A9 or express 84P2A9 at a different level are found to express 84P2A9 or have an increased expression of 84P2A9 (see, e.g., the 84P2A9 expression in kidney, lung and colon cancer cells and in patient samples, etc., shown in FIGS. 4-10). In such assays, artisans may father wish to generate supplementary evidence of metastasis by testing the biological sample for the presence of a second tissue restricted marker (in addition to 84P2A9) such as PSA, PSCA, etc. (see, e.g., Alanen, et al., Pathol. Res. Pract. 192(3): 233-237 (1996)).

Just as PSA polynucleotide fragments and polynucleotide variants are employed by skilled artisans for use in methods of monitoring PSA, 84P2A9 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson, et al., Methods Mol. Biol. 98:121-154 (1998)). An additional illustration of the use of such fragments is provided in Example 3, where an 84P2A9 polynucleotide fragment is used as a probe to show the overexpression of 84P2A9 mRNAs in cancer cells. In addition, in order to facilitate their use by medical practitioners, variant polynucleotide sequences are typically used as primers and probes for the corresponding mRNAs in PCR and Northern analyses (see, e.g., Sawai, et al., Fetal Diagn. Ther. 1996 November-December; 11(6):407-13 and Current Protocols In Molecular Biology, Volume 2, Unit 2, Frederick M. Ausubul, et al. eds., 1995)). Polynucleotide fragments and variants are typically useful in this context as long as they have the common attribute or characteristic of being capable of binding to a target polynucleotide sequence (e.g., the 84P2A9 polynucleotide shown in SEQ ID NO:1) under conditions of high stringency.

Just as PSA polypeptide fragments and polypeptide variants are employed by skilled artisans for use in methods of monitoring the PSA molecule, 84P2A9 polypeptide fragments and polypeptide variants can also be used in an analogous manner. In particular, typical PSA polypeptides used in methods of monitoring PSA are fragments of the PSA protein which contain an antibody epitope that can be recognized by an antibody or T cell that specifically binds to the PSA protein. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubul, et al., eds., 1995). In this context, each epitope(s) in a protein of interest functions to provide the architecture with which an antibody or T cell is reactive. Typically, skilled artisans generally create a variety of different polypeptide fragments that can be used in order to generate antibodies specific for different portions of a polypeptide of interest (see, e.g., U.S. Pat. Nos. 5,840,501 and 5,939,533). For example it may be preferable to utilize a polypeptide comprising one of the 84P2A9 biological motifs discussed herein or available in the art. Polypeptide fragments and variants or analogs are typically useful in this context as long as they comprise an epitope capable of generating an antibody or T cell specific for a target polypeptide sequence (e.g., the 84P2A9 polypeptide shown in SEQ ID NO:2).

As shown herein, the 84P2A9 polynucleotides and polypeptides (as well as the 84P2A9 polynucleotide probes and anti-84P2A9 antibodies or T cells used to identify the presence of these molecules) exhibit specific properties that make them useful in diagnosing cancers of the prostate. Diagnostic assays that measure the presence of 84P2A9 gene products, in order to evaluate the presence or onset of the particular disease conditions described herein such as prostate cancer are particularly useful in identifying patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a testing for PSA alone (see, e.g., Alanen, et al., Pathol. Res. Pract. 192(3): 233-237 (1996)), and consequently, materials such as 84P2A9 polynucleotides and polypeptides (as well as the 84P2A9 polynucleotide probes and anti-84P2A9 antibodies used to identify the presence of these molecules) must be employed to confirm metastases of prostatic origin.

Finally, in addition to their use in diagnostic assays, the 84P2A9 polynucleotides disclosed herein have a number of other specific utilities such as their use in the identification of oncogenetic associated chromosomal abnormalities in 1q32.3. Moreover, in addition to their use in diagnostic assays, the 84P2A9-related proteins and polynucleotides disclosed herein have other utilities such as their use in the forensic analysis of tissues of unknown origin (see, e.g., Takahama, K, Forensic Sci Int 1996 Jun. 28; 80(1-2): 63-9).

84P2A9 Polynucleotides

One aspect of the invention provides polynucleotides corresponding or complementary to all or part of an 84P2A9 gene, mRNA, and/or coding sequence, preferably in isolated form, including polynucleotides encoding an 84P2A9 protein and fragments thereof, DNA, RNA, DNA/RNA hybrid, and related molecules, polynucleotides or oligonucleotides complementary to an 84P2A9 gene or mRNA sequence or a part thereof, and polynucleotides or oligonucleotides that hybridize to an 84P2A9 gene, mRNA, or to an 84P2A9 encoding polynucleotide (collectively, "84P2A9 polynucleotides").

One embodiment of an 84P2A9 polynucleotide is an 84P2A9 polynucleotide having the sequence shown in SEQ ID NO:1. An 84P2A9 polynucleotide can comprise a polynucleotide having the nucleotide sequence of human 84P2A9 as shown in SEQ ID NO:1, wherein T can also be U; a polynucleotide that encodes all or part of the 84P2A9 protein; a sequence complementary to the foregoing; or a polynucleotide fragment of any of the foregoing. Another embodiment comprises a polynucleotide having the sequence as shown in SEQ ID NO:1, from nucleotide residue number 163 through nucleotide residue number 1674, or from residue number 718 through residue number 1390, wherein T can also be U. Another embodiment comprises a polynucleotide encoding an 84P2A9 polypeptide whose sequence is encoded by the cDNA contained in the plasmid as deposited with American Type Culture Collection as Accession No. PTA-1151. Another embodiment comprises a polynucleotide that is capable of hybridizing under stringent hybridization conditions to the human 84P2A9 cDNA shown in SEQ ID NO:1 or to a polynucleotide fragment thereof.

Typical embodiments of the invention disclosed herein include 84P2A9 polynucleotides encoding specific portions of the 84P2A9 mRNA sequence (and those which are complementary to such sequences) such as those that encode the protein and fragments thereof, for example of 4, 5, 6, 7, 8, 9, 10, 11, 12, 13, 14, 15 or more contiguous amino acids. For example, representative embodiments of the invention disclosed herein include: polynucleotides encoding about amino acid position 1 to about amino acid 10 of the 84P2A9 protein shown in FIG. 2 (SEQ ID NO:2), polynucleotides encoding about amino acid 10 to about amino acid 20 of the 84P2A9 protein shown in FIG. 2, polynucleotides encoding about amino acid 20 to about amino acid 30 of the 84P2A9 protein shown in FIG. 2, polynucleotides encoding about amino acid 30 to about amino acid 40 of the 84P2A9 protein shown in FIG. 2, polynucleotides encoding about amino acid 40 to about amino acid 50 of the 84P2A9 protein shown in FIG. 2, polynucleotides encoding about amino acid 50 to about amino acid. Sixty of the 84P2A9 protein shown in FIG. 2, polynucleotides encoding about amino acid 60 to about amino acid 70 of the 84P2A9 protein shown in FIG. 2, polynucleotides encoding about amino acid 70 to about amino acid 80 of the 84P2A9 protein shown in FIG. 2, polynucleotides encoding about amino acid 80 to about amino acid 90 of the 84P2A9 protein shown in FIG. 2 and polynucleotides encoding about amino acid 90 to about amino acid 100 of the 84P2A9 protein shown in FIG. 2, etc. Following this scheme, polynucleotides (of at least 10 nucleic acids) encoding portions of the amino acid sequence of amino acids 100-504 of the 84P2A9 protein are typical embodiments of the invention.

Polynucleotides encoding larger portions of the 84P2A9 protein are also contemplated. For example polynucleotides encoding from about amino acid 1 (or 20 or 30 or 40, etc.) to about amino acid 20, (or 30, or 40 or 50, etc.) of the 84P2A9 protein shown in FIG. 2 can be generated by a variety of techniques well known in the art. An illustrative embodiment of such a polynucleotide consists of a polynucleotide having the sequence as shown in FIG. 2, from nucleotide residue number 718 through nucleotide residue number 1390.

Additional illustrative embodiments of the invention disclosed herein include 84P2A9 polynucleotide fragments encoding one or more of the biological motifs contained within the 84P2A9 protein sequence. In one embodiment, typical polynucleotide fragments of the invention can encode one or more of the nuclear localization sequences disclosed herein. In another embodiment, typical polynucleotide fragments of the invention can encode one or more of the regions of 84P2A9 that exhibit homology to LUCA 15 and/or KIAA1152 and/or NY-Lu-12 lung cancer antigen (AF 042857), which exhibits Zinc finger and RNA binding motifs (see, e.g., Gure, et al., *Cancer Res.* 58(5): 1034-1041 (1998). In another embodiment of the invention, typical polynucleotide fragments can encode one or more of the 84P2A9 N-glycosylation sites, cAMP and cCMP-dependent protein kinase phosphorylation sites, casein kinase II phosphorylation sites or N-myristoylation site and amidation sites as disclosed in greater detail in the text discussing the 84P2A9 protein and polypeptides herein. In yet another embodiment of the invention, typical polynucleotide fragments can encode sequences that are unique to one or more 84P2A9 alternative splicing variants, such as the splice variant that generates the 4.5 KB transcript that is overexpressed in prostate cancers shown in FIG. 4.

The polynucleotides of the preceding paragraphs have a number of different specific uses. For example, because the human 84P2A9 gene maps to chromosome 1q32.3, polynucleotides encoding different regions of the 84P2A9 protein can be used to characterize cytogenetic abnormalities on chromosome 1, band q32 that have been identified as being associated with various cancers. In particular, a variety of chromosomal abnormalities in 1q32 including translocations and deletions have been identified as frequent cytogenetic abnormalities in a number of different cancers (see, e.g., Bieche, et al., *Genes Chromosomes Cancer*, 24(3): 255-263 (1999); Gorunova, et al., *Genes Chromosomes Cancer*, 26(4): 312-321 (1999); Reid, et al., *Cancer Res.* (22): 5415-5423 (1995)). Consequently, polynucleotides encoding specific regions of the 84P2A9 protein provide new tools that can be used to delineate with a greater precision than previously possible, the specific nature of the cytogenetic abnormalities in this region of chromosome 1 that can contribute to the malignant phenotype. In this context, these polynucleotides satisfy a need in the art for expanding the sensitivity of chromosomal screening in order to identify more subtle and less common chromosomal abnormalities (see, e.g., Evans, et al., *Am. J. Obstet. Gynecol* 171(4): 1055-1057 (1994)).

Alternatively, as 84P2A9 is shown to be highly expressed in prostate cancers (FIG. 4), these polynucleotides can be used in methods assessing the status of 84P2A9 gene products in normal versus cancerous tissues. Typically, polynucleotides encoding specific regions of the 84P2A9 protein can be used to assess the presence of perturbations (such as deletions, insertions, point mutations, or alterations resulting in a loss of an antigen, etc.) in specific regions (such regions containing a nuclear localization signal) of the 84P2A9 gene products. Exemplary assays include both RT-PCR assays as well as single-strand conformation polymorphism (SSCP) analysis (see, e.g., Marrogi, et al., *J. Cutan. Pathol.* 26(8): 369-378 (1999), both of which utilize polynucleotides encoding specific regions of a protein to examine these regions within the protein.

Other specifically contemplated nucleic acid related embodiments of the invention disclosed herein are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 84P2A9 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 84P2A9. See for example, Jack Cohen, *OLIGODEOXYNUCLEOTIDES, Antisense Inhibitors of Gene Expression*, CRC Press, 1989; and Synthesis 1:1-5 (1988). The 84P2A9 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent See Iyer, R. P., et al., *J. Org. Chem.* 55:4693-4698 (1990); and Iyer, R. P., et al., *J. Am. Chem. Soc.* 112: 1253-1254 (1990). Additional 84P2A9 antisense oligonucleotides of the present invention include morpholino antisense oligonucleotides known in the art (see, e.g., Partridge, et al., 1996, *Antisense & Nucleic Acid Drug Development* 6: 169-175).

The 84P2A9 antisense oligonucleotides of the present invention typically can be RNA or DNA that is complementary to and stably hybridizes with the first 100 N-terminal codons or last 100 C-terminal codons of the 84P2A9 genomic sequence or the corresponding mRNA. Absolute complementarity is not required, although high degrees of complementarity are preferred. Use of an oligonucleotide complementary to this region allows for the selective hybridization to 84P2A9 mRNA and not to mRNA specifying other regulatory subunits of protein kinase. Preferably, the 84P2A9 antisense oligonucleotides of the present invention are a 15 to 30-mer fragment of the antisense DNA molecule having a sequence that hybridizes to 84P2A9 mRNA. Optionally, 84P2A9 antisense oligonucleotide is a 30-mer oligonucleotide that is complementary to a region in the first 10 N-terminal codons or last 10 C-terminal codons of 84P2A9. Alternatively, the antisense molecules are modified to employ ribozymes in the inhibition of 84P2A9 expression. L. A. Couture & D. T. Stinchcomb; *Trends Genet.* 12: 510-515 (1996).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers can be used to detect the presence of an 84P2A9 polynucleotide in a sample and as a means for detecting a cell expressing an 84P2A9 protein.

Examples of such probes include polypeptides comprising all or part of the human 84P2A9 cDNA sequences shown in FIG. 2. Examples of primer pairs capable of specifically amplifying 84P2A9 mRNAs are also described in the Examples that follow. As will be understood by the skilled artisan, a great many different primers and probes can be prepared based on the sequences provided herein and used effectively to amplify and/or detect an 84P2A9 mRNA.

The 84P2A9 polynucleotides of the invention are useful for a variety of purposes, including but not limited to their use as probes and primers for the amplification and/or detection of the 84P2A9 gene(s), mRNA(s), or fragments thereof; as reagents for the diagnosis and/or prognosis of prostate cancer and other cancers; as coding sequences capable of directing the expression of 84P2A9 polypeptides; as tools for modulating or inhibiting the expression of the 84P2A9 gene(s) and/or translation of the 84P2A9 transcript(s); and as therapeutic agents.

Isolation of 84P2A9-Encoding Nucleic Acid Molecules

The 84P2A9 cDNA sequences described herein enable the isolation of other polynucleotides encoding 84P2A9 gene product(s), as well as the isolation of polynucleotides encoding 84P2A9 gene product homologs, alternatively spliced isoforms, allelic variants, and mutant forms of the 84P2A9 gene product Various molecular cloning methods that can be employed to isolate full length cDNAs encoding an 84P2A9 gene are well known (See, for example, Sambrook, J., et al., *Molecular Cloning: A Laboratory Manual*, 2d edition, Cold Spring Harbor Press, New York, 1989; *Current Protocols in Molecular Biology*. Ausubel, et al., Eds., Wiley and Sons, 1995). For example, lambda phage cloning methodologies can be conveniently employed, using commercially available cloning systems (e.g., Lambda ZAP Express, Stratagene).

Phage clones containing 84P2A9 gene cDNAs can be identified by probing with a labeled 84P2A9 cDNA or a fragment thereof. For example, in one embodiment, the 84P2A9 cDNA (FIG. 2) or a portion thereof can be synthesized and used as a probe to retrieve overlapping and full length cDNAs corresponding to an 84P2A9 gene. The 84P2A9 gene itself can be isolated by screening genomic DNA libraries, bacterial artificial chromosome libraries (BACs), yeast artificial chromosome libraries (YACs), and the like, with 84P2A9 DNA probes or primers.

Recombinant DNA Molecules and Host-Vector Systems

The invention also provides recombinant DNA or RNA molecules containing an 84P2A9 polynucleotide or a fragment or analog or homologue thereof, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook, et al., 1989, supra).

The invention further provides a host-vector system comprising a recombinant DNA molecule containing an 84P2A9 polynucleotide or fragment or analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of 84P2A9 or a fragment or analog or homolog thereof can be used to generate 84P2A9 proteins or fragments thereof using any number of host-vector systems routinely used and widely known in the art.

A wide range of host-vector systems suitable for the expression of 84P2A9 proteins or fragments thereof are available, see for example, Sambrook, et al., 1989, supra; *Current Protocols in Molecular Biology,* 1995, supra). Preferred vectors for mammalian expression include but are not limited to pcDNA 3.1 myc-His-tag (Invitrogen) and the retroviral vector pSR.alpha.tkneo (Muller, et al., 1991, *MCB* 11:1785). Using these expression vectors, 84P2A9 may be preferably expressed in several prostate cancer and non-prostate cell lines, including for example 293, 293T, rat-1, NIH 3T3 and TsuPr1. The host-vector systems of the invention are useful for the production of an 84P2A9 protein or fragment thereof. Such host-vector systems can be employed to study the functional properties of 84P2A9 and 84P2A9 mutations or analogs.

Recombinant human 84P2A9 protein or an analog or homolog or fragment thereof can be produced by mammalian cells transfected with a construct encoding 84P2A9. In an illustrative embodiment described in the Examples, 293T cells can be transfected with an expression plasmid encoding 84P2A9 or fragment or analog or homolog thereof, the 84P2A9 or related protein is expressed in the 293T cells, and the recombinant 84P2A9 protein can be isolated using standard purification methods (e.g., affinity purification using anti-84P2A9 antibodies). In another embodiment, also described in the Examples herein, the 84P2A9 coding sequence is subcloned into the retroviral vector pSR.alpha.MSVtkneo and used to infect various mammalian cell lines, such as NIH 3T3, TsuPr1, 293 and rat-1 in order to establish 84P2A9 expressing cell lines. Various other expression systems well known in the art can also be employed. Expression constructs encoding a leader peptide joined in frame to the 84P2A9 coding sequence can be used for the generation of a secreted form of recombinant 84P2A9 protein.

Proteins encoded by the 84P2A9 genes, or by analogs or homologs or fragments thereof, will have a variety of uses, including but not limited to generating antibodies and in methods for identifying ligands and other agents and cellular constituents that bind to an 84P2A9 gene product Antibodies raised against an 84P2A9 protein or fragment thereof can be useful in diagnostic and prognostic assays, and imaging methodologies in the management of human cancers characterized by expression of 84P2A9 protein, including but not limited to cancers of the prostate and testis. Such antibodies can be expressed intracellularly and used in methods of treating patients with such cancers. Various immunological assays useful for the detection of 84P2A9 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies can be labeled and used as immunological imaging reagents capable of detecting 84P2A9 expressing cells (e.g., in radioscintigraphic imaging methods). 84P2A9 Proteins can also be particularly useful in generating cancer vaccines, as further described below.

84P2A9 Polypeptides

Another aspect of the present invention provides 84P2A9-related proteins and polypeptide fragments thereof. Specific embodiments of 84P2A9 proteins comprise a polypeptide having all or part of the amino acid sequence of human 84P2A9 as shown in FIG. 2. Alternatively, embodiments of 84P2A9 proteins-comprise variant polypeptides having alterations in the amino acid sequence of human 84P2A9 shown in FIG. 2.

In general, naturally occurring allelic variants of human 84P2A9 share a high degree of structural identity and homology (e.g., 90% or more identity). Typically, allelic variants of the 84P2A9-related proteins contain conservative amino acid substitutions within the 84P2A9 sequences described herein or contain a substitution of an amino acid from a corresponding position in a homologue of 84P2A9. One class of 84P2A9 allelic variants are proteins that share a high degree of homology with at least a small region of a particular 84P2A9 amino acid sequence, but further contain a radical departure from the sequence, such as a non-conservative substitution, truncation, insertion or frame shift. In comparisons of protein sequences, the terms, similarity, identity, and homology each have a distinct meaning. Moreover, orthology and paralogy are important concepts describing the relationship of members of a given protein family in one organism to the members of the same family in other organisms.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g., Table 2 herein; pages 13-15 "Biochemistry" $2^{nd}$ ED. Lubert Stryer ed (Stanford University); Henikoff, et al., PNAS 1992 Vol 89 10915-10919; Lei, et al., J Biol Chem 1995 May 19; 270(20):11882-6).

Embodiments of the invention disclosed herein include a wide variety of art accepted variants of 84P2A9 proteins such as polypeptides having amino acid insertions, deletions and substitutions. 84P2A9 Variants can be made using methods known in the art such as site-directed mutagenesis, alanine scanning, and PCR mutagenesis. Site-directed mutagenesis [Carter, et al., Nucl. Adds Res., 13:4331 (1986); Zoller, et al., Nucl. Acids Res., 10:6487 (1987)], cassette mutagenesis [Wells, et al., Gene, 34:315 (1985)], restriction selection mutagenesis [Wells, et al., Philos. Trans. R. Soc. London SerA, 317:415 (1986)] or other known techniques can be performed on the cloned DNA to produce the 84P2A9 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isosteric amino acid can be used.

As defined herein, 84P2A9 variants, analogs or homologs, have the distinguishing attribute of having at least one epitope in common with an 84P2A9 protein having the amino acid sequence of SEQ ID NO:2, such that an antibody or T cell that specifically binds to an 84P2A9 variant will also specifically bind to the 84P2A9 protein-having the amino acid sequence of SEQ ID NO:2. A polypeptide ceases to be a variant of the protein shown in SEQ ID NO:2 when it no longer contains an epitope capable of being recognized by an antibody or T cell that specifically binds to an 84P2A9 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair, et al., J. Immunol. 2000 165(12): 6949-6955; Hebbes, et al., Mol Immunol (1989) 26(9):865-73; Schwartz, et al., J Immunol (1985) 135(4):2598-608. Another specific class of 84P2A9-related protein variants shares 90% or more identity with the amino acid sequence of SEQ ID NO:2 or a fragment thereof. Another specific class of 84P2A9 protein variants or analogs comprise one or more of the 84P2A9 biological motifs described below or presently known in the art. Thus, encompassed by the present invention are analogs of 84P2A9 fragments (nucleic or amino acid) that altered functional (e.g., immunogenic) properties relative to the starting fragment. It is to be appreciated that motifs now or which become part of the art are to be applied to the nucleic or amino acid sequences of FIG. 2.

As discussed herein, embodiments of the claimed invention include polypeptides containing less than the 504 amino acid sequence of the 84P2A9 protein shown in FIG. 2. For example, representative embodiments of the invention comprise peptides/proteins having any 4, 5, 6, 7, 8, 9, 10, 11, 12, 13, 14, 15 or more contiguous amino acids of the 84P2A9 protein shown in FIG. 2 (SEQ ID NO:2). Moreover, representative embodiments of the invention disclosed herein include polypeptides consisting of about amino acid 1 to about amino acid 10 of the 84P2A9 protein shown in FIG. 2, polypeptides consisting of about amino acid 10 to about amino acid 20 of the 84P2A9 protein shown in FIG. 2, polypeptides consisting of about amino acid 20 to about amino acid 30 of the 84P2A9 protein shown in FIG. 2, polypeptides consisting of about amino acid 30 to about amino acid 40 of the 84P2A9 protein shown in FIG. 2, polypeptides consisting of about amino acid 40 to about amino acid 50 of the 84P2-A9 protein shown in FIG. 2, polypeptides consisting of about amino acid 50 to about amino acid 60 of the 84P2A9 protein shown in FIG. 2, polypeptides consisting of about amino acid 60 to about amino acid 70 of the 84P2A9 protein shown in FIG. 2, polypeptides consisting of about amino acid 70 to about amino acid 80 of the 84P2A9 protein shown in FIG. 2, polypeptides consisting of about amino acid 80 to about amino acid 90 of the 84P2A9 protein shown in FIG. 2 and polypeptides consisting of about amino acid 90 to about amino acid 100 of the 84P2A9 protein shown in FIG. 2, etc., throughout the entirety of the 84P2A9 sequence. Following this scheme, polypeptides consisting of portions of the amino acid sequence of amino acids 100-504 of the 84P2A9 protein are typical embodiments of the invention. Polypeptides consisting of larger portions of the 84P2A9 protein are also contemplated. For example polypeptides consisting of about amino acid 1 (or 20 or 30 or 40, etc.) to about amino acid 20, (or 30, or 40 or 50, etc.) of the 84P2A9 protein shown in FIG. 2 can be generated by a variety of techniques well known in the art. It is to be appreciated that the starting and stopping positions in this paragraph refer to the specified position as well as that position plus or minus 5 residues.

Additional illustrative embodiments of the invention disclosed herein include 84P2A9-related proteins containing the amino acid residues of one or more of the biological motifs contained within the 84P2A9-related protein sequence as shown in FIG. 2. In one embodiment, proteins of the invention comprise one or more of the 84P2A9 nuclear localization sequences such as RKRR (SEQ ID NO:449) at residues 42-50 of SEQ ID NO:2, RKRR (SEQ ID NO:449) at residues 47-50 of SEQ ID NO:2, KRRP (SEQ ID NO:450) at residues 101-104 of SEQ ID NO:2, RRRRRK (SEQ ID NO:451) at residues 135-139 of SEQ ID NO:2 and/or KKRK (SEQ ID NO:452) at residues 186-189 of SEQ ID NO:2. In another embodiment, proteins of the invention comprise one or more of the 8P2A9 N-glycosylation sites such as NRTL (SEQ ID NO:453) at residues 131-134 of SEQ ID NO:2, NQTN (SEQ ID NO:454) at residues 212-215 of SEQ ID NO:2 and/or NCSV (SEQ ID NO:455) at residues 394-397 of SEQ ID NO:2. In another embodiment, proteins of the invention comprise one or more of the regions of 84P2A9 that exhibit homology to LUCA 15 and/or KIAA1152. In another embodiment, proteins of the invention comprise one or more of the 84P2A9 cAMP and cGMP-dependent protein kinase phosphorylation sites such as KRRS (SEQ ID NO:456) at residues 48-51 of SEQ ID NO:2 and/or RRPS (SEQ ID NO:457) at residues 102-105 of SEQ ID NO:2. In another embodiment, proteins of the invention comprise one or more of the 84P2A9 Protein Kinase C phosphorylation sites such as TLR (SEQ ID NO:458) at residues 133-135 of SEQ ID NO:2, SNK (SEQ ID NO:459) at residues 152-154 of SEQ ID NO:2, SDR (SEQ ID NO:460) at residues 171-173 of SEQ ID NO:2, TNK (SEQ ID NO:461) at residues 214-216 of SEQ ID NO:2, SRR (SEQ ID NO:462) at residues 313-315 of SEQ ID NO:2, SSK (SEQ ID NO:463) at residues 328-330 of SEQ ID NO:2 and/or SVR (SEQ ID NO:464) at residues 396-398 of SEQ ID NO:2. In another embodiment, proteins of the invention comprise one or more of the 84P2A9 casein kinase II phosphorylation sites such as SALE (SEQ ID NO:465) at residues 10-13 of SEQ ID NO:2, SSLE (SEQ ID NO:466) at residues 70-73 of SEQ ID NO:2, SLEE (SEQ ID NO:467) at residues 71-74 of SEQ ID NO:2, SDSD (SEQ ID NO:468) at residues 91-94 of SEQ ID NO:2, TNKD (SEQ ID NO:469) at residues 214-217 of SEQ ID NO:2, SESD (SEQ ID NO:470) at residues 232-235 of SEQ ID NO:2, SSTD (SEQ ID NO:471) at residues 240-243 of SEQ ID NO:2, TNDE (SEQ ID NO:472) at residues 248-251 of SEQ ID NO:2, TELD (SEQ ID NO:473) at residues 287-290 of SEQ ID NO:2 and/or TEHD (SEQ ID NO:474) at residues 374-377 of SEQ ID NO:2. In another embodiment, proteins of the invention comprise one or more of the N-myristoylation sites such as GSDSSL (SEQ ID NO:475) at residues 67-72 of SEQ ID NO:2, GLFTND (SEQ ID NO:476) at residues 245-250 of SEQ ID NO:2, GGACGI (SEQ ID NO:477) at residues 269-274 of SEQ ID NO:2, GGTPTS (SEQ ID NO:478) at residues 336-341 of SEQ ID NO:2, GTPTSM (SEQ ID NO:479) at residues 337-342 of SEQ ID NO:2, GSLCTG (SEQ ID NO:480) at residues 409-414 of SEQ ID NO:2, GSGLGR (SEQ ID NO:481) at residues 459-464 of SEQ ID NO:2 and/or at residues 481-486 of SEQ ID NO:2. In another embodiment, proteins of the invention comprise one or more amidation sites such as RGRK (SEQ ID NO:483) at residues 45-48 of SEQ ID NO:2 and/or RGKR (SEQ ID NO:484) at residues 113-116 of SEQ ID NO:2. An illustrative embodiment of such a polypeptide includes two or more amino acid sequences selected from the group consisting of KKRK (SEQ ID NO:452), NQTN (SEQ ID NO:454), NCSV (SEQ ID NO:455), TNK (SEQ ID NO:461), SRR (SEQ ID NO:462), SSK (SEQ ID NO:463), SVR (SEQ ID NO:464), GLFTND (SEQ ID NO:476), GGACGI (SEQ ID NO:477), GGTPTS (SEQ ID NO:478), GTPTSM (SEQ ID NO:479) and GSLCTG (SEQ ID NO:480) (as identified above in SEQ ID NO:2). In a preferred embodiment, the polypeptide comprises three or four or five or six or more amino acid sequences KKRK (SEQ ID NO:452), NQTN (SEQ ID NO:454), NCSV (SEQ ID NO:455), TNK (SEQ ID NO:461), SRR (SEQ ID NO:462), SSK (SEQ ID NO:463), SVR (SEQ ID NO:464), GLFTND (SEQ ID NO:476), GGACGI (SEQ ID NO:477), GGTPTS (SEQ ID NO:478), GTPTSM (SEQ ID NO:479) and GSLCTG (SEQ ID NO:480) (as identified above in SEQ ID NO:2).

In another embodiment, proteins of the invention comprise one or more of the immunoreactive epitopes identified by a process described herein such as such as those shown in Table 1. Processes for identifying peptides and analogues having affinities for HLA molecules and which are correlated as immunogenic epitopes, are well known in the art. Also disclosed are principles for creating analogs of such epitopes in order to modulate immunogenicity. A variety of references are useful in the identification of such molecules. See, for example, WO 9733602 to Chestnut, et al.; Sette, *Immunogenetics* 1999 50(3-4): 201-212; Sette, et al., *J. Immunol.* 2001 166(2): 1389-1397; Alexander, et al., *Immunol. Res.* 18(2):

79-92; Sidney, et al., *Hum. Immunol.* 1997 58(1): 12-20; Kondo, et al., *Immunogenetics* 1997 45(4): 249-258; Sidney, et al., *J. Immunol.* 1996 157(8): 3480-90; and Falk, et al., *Nature* 351: 290-6 (1991); Hunt, et al., *Science* 255:1261-3 (1992); Parker, et al., *J. Immunol.* 149:3580-7 (1992); Parker, et al., *J. Immunol.* 152:163-75 (1994)); Kast, et al., 1994 152(8): 3904-12; Borras-Cuesta, et al., *Hum. Immunol.* 2000 61(3): 266-278; Alexander, et al., *J. Immunol.* 2000 164(3); 164(3): 1625-1633; Alexander, et al., *PMID:* 7895164, UI: 95202582; O'Sullivan, et al., *J. Immunol.* 1991 147(8): 2663-2669; Alexander, et al., *Immunity* 1994 1(9): 751-761 and Alexander, et al., *Immunol. Res.* 1998 18(2): 79-92. The disclosures of these publications are hereby incorporated by reference herein in their entireties.

Related embodiments of the invention comprise polypeptides containing combinations of the different motifs discussed herein, where certain embodiments contain no insertions, deletions or substitutions either within the motifs or the intervening sequences of these polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

In another embodiment of the invention, proteins of the invention comprise amino acid sequences that are unique to one or more 84P2A9 alternative splicing variants, such as the splice variant encoded by the 4.5 KB transcript that is overexpressed in prostate cancers and shown in FIG. 4. The monitoring of alternative splice variants of 84P2A9 is useful because changes in the alternative splicing of proteins is suggested as one of the steps in a series of events that lead to the progression of cancers (see, e.g., Carstens, et al., *Oncogene* 15(250: 3059-3065 (1997)). Consequently, monitoring of alternative splice variants of 84P2A9 provides an additional means to evaluate syndromes associated with perturbations in 84P2A9 gene products such as cancers.

Polypeptides comprising one or more of the 84P2A9 motifs discussed herein are useful in elucidating the specific characteristics of a malignant phenotype in view of the observation that the 84P2A9 motifs discussed herein are associated with growth disregulation and because 84P2A9 is overexpressed in cancers (FIG. 4). Thus, the presence in a protein of motifs related to these enzymes or molecules is relevant. For example, Casein kinase II, cAMP and cCMP-dependent protein kinase and Protein Kinase C for example are enzymes known to be associated with the development of the malignant phenotype (see, e.g., Chen, et al., *Lab Invest.*, 78(2): 165-174 (1998); Gaiddon, et al., *Endocrinology* 136(10): 4331-4338 (1995); Hall, et al., *Nucleic Acids Research* 24(6): 1119-1126 (1996); Peterziel, et al., *Oncogene* 18(46): 6322-6329 (1999) and O'Brian, *Oncol. Rep.* 5(2): 305-309 (1998)). Moreover, both glycosylation and myristoylation are protein modifications also associated with cancer and cancer progression (see, e.g., Dennis, et al., *Biochim. Biophys. Acta* 1473 (1):21-34 (1999); Raju, et al., *Exp. Cell Res.* 235(1): 145-154 (1997)). Amidation is another protein modification associated with cancer and cancer progression (see, e.g., Treston, et al., *J. Natl. Cancer Inst. Monogr.* (13): 169-175 (1992)). In addition, nuclear localization sequences are believed to influence the malignant potential of a cell (see, e.g., Mirski, et al., *Cancer Res.* 55(10): 2129-2134 (1995)).

The proteins of the invention have a number of different specific uses. As 84P2A9 is shown to be highly expressed in prostate cancers (FIG. 4), these peptides/proteins are used in methods assessing the status of 84P2A9 gene products in normal versus cancerous tissues and elucidating the malignant phenotype. Typically, polypeptides encoding specific regions of the 84P2A9 protein are used to assess the presence of perturbations (such as deletions, insertions, point mutations, etc.) in specific regions (such regions containing a nuclear localization signal) of the 84P2A9 gene products. Exemplary assays utilize antibodies or T cells targeting 84P2A9-related proteins comprising the amino acid residues of one or more of the biological motifs contained within the 84P2A9 polypeptide sequence in order to evaluate the characteristics of this region in normal versus cancerous tissues. Alternatively, 84P2A9 polypeptides containing the amino acid residues of one or more of the biological motifs contained within the 84P2A9 proteins are used to screen for factors that interact with that region of 84P2A9.

As discussed herein, redundancy in the genetic code permits variation in 84P2A9 gene sequences. In particular, one skilled in the art will recognize specific codon preferences by a specific host species, and can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET. Nucleotide sequences that have been optimized for a particular host species by replacing any codons having a usage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell. Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak *PNAS* 92(7): 2662-2666, (1995) and Kozak *NAR* 15(20): 8125-8148 (1987)). Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

84P2A9 proteins are embodied in many forms, preferably in isolated form. A purified 84P2A9 protein molecule will be substantially free of other proteins or molecules that impair the binding of 84P2A9 to antibody or other ligand. The nature and degree of isolation and purification will depend on the intended use. Embodiments of an 84P2A9 protein include a purified 84P2A9 protein and a functional, soluble 84P2A9 protein. In one embodiment, a functional soluble 84P2A9 protein or fragment thereof retains the ability to be bound by antibody, T cell or other ligand.

The invention also provides 84P2A9 proteins comprising biologically active fragments of the 84P2A9 amino acid sequence corresponding to part of the 84P2A9 amino acid sequence shown in FIG. 2. Such proteins of the invention exhibit properties of the 84P2A9 protein, such as the ability to elicit the generation of antibodies that specifically bind an epitope associated with the 84P2A9 protein; to be bound by such antibodies; to elicit the activation of HTL or CTL; and/or, to be recognized by HTL or CTL.

84P2A9-Related proteins are generated using standard peptide synthesis technology or using chemical cleavage methods well known in the art. Alternatively, recombinant methods can be used to generate nucleic acid molecules that encode an 84P2A9-related protein. In one embodiment, the 84P2A9-encoding nucleic acid molecules described herein provide means for generating defined fragments of 84P2A9 proteins. 84P2A9 Protein fragments/subsequences are particularly useful in generating and characterizing domain specific antibodies (e.g., antibodies recognizing an extracellular or intracellular epitope of an 84P2A9 protein), in identifying agents or cellular factors that bind to 84P2A9 or a particular structural domain thereof, and in various therapeutic contexts, including but not limited to cancer vaccines or methods of preparing such vaccines.

84P2A9 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-84P2A9 antibodies, or T cells or in identifying cellular factors that bind to 84P2A9.

Illustrating this, the binding of peptides from 84P2A9 proteins to the human MHC class I molecule HLA-A2 were predicted. Specifically, the complete amino acid sequence of the 84P2A9 protein was entered into the HLA Peptide Motif Search algorithm found in the Bioinformatics and Molecular Analysis Section (BIMAS) Web site. The HLA Peptide Motif Search algorithm was developed by Dr. Ken Parker based on binding of specific peptide sequences in the groove of HLA Class I molecules and specifically HLA-A2 (see, e.g., Falk, et al. *Nature* 351: 290-6 (1991); Hunt, et al., *Science* 255:1261-3 (1992); Parker, et al., *J. Immunol.* 149:3580-7 (1992); Parker, et al., *J. Immunol.* 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker, et al., *J. Immunol.* 149:3580-7 (1992)). Selected results of 84P2A9 predicted binding peptides are shown in Table 1 below. It is to be appreciated that every epitope predicted by the DIMAS site, or specified by the HLA class I or class I motifs available in the art are to be applied (e.g., visually or by computer based methods, or appreciated by those of skill in the relevant art) or which become part of the art are within the scope of the invention. In Table 1, the top 10 ranking candidates for each family member are shown along with their location, the amino acid sequence of each specific peptide, and an estimated binding score. The binding score corresponds to the estimated half-time of dissociation of complexes containing the peptide at 37° C. at pH 6.5. Peptides with the highest binding score (i.e., 63.04 for 84P2A9) are predicted to be the most tightly bound to HLA Class I on the cell surface for the greatest period of time and thus represent the best immunogenic targets for T-cell recognition. Actual binding of peptides to an HLA allele can be evaluated by stabilization of HLA expression on the antigen-processing defective cell line T2 (see, e.g., Xue, et al., *Prostate* 30:73-8 (1997) and Peshwa, et al., *Prostate* 36:129-38 (1998)). Immunogenicity of specific peptides can be evaluated in vitro by stimulation of CD8+ cytotoxic T lymphocytes (CTL) in the presence of antigen presenting cells such as dendritic cells.

In an embodiment described in the examples that follow, 84P2A9 can be conveniently expressed in cells (such as 293T cells) transfected with a commercially available expression vector such as a CMV-driven expression vector encoding 84P2A9 with a C-terminal 6xHis and MYC tag (pcDNA3.1/myc HIS, Invitrogen or Tag5, GenHunter Corporation, Nashville Term.). The Tag5 vector provides an IgGK secretion signal that can be used to facilitate the production of a secreted 84P2A9 protein in transfected cells. The secreted HIS-tagged 84P2A9 in the culture media can be purified, e.g., using a nickel column using standard techniques.

Modifications of 84P2A9-related proteins such as covalent modifications are included within the scope of this invention. One type of covalent modification includes reacting targeted amino acid residues of an 84P2A9 polypeptide with an organic derivatizing agent that is capable of reacting with selected side chains or the N- or C-terminal residues of the 84P2A9. Another type of covalent modification of the 84P2A9 polypeptide included within the scope of this invention comprises altering the native glycosylation pattern of a protein of the invention. "Altering the native glycosylation pattern" is intended for purposes herein to mean deleting one or more carbohydrate moieties found in native sequence 84P2A9 (either by removing the underlying glycosylation site or by deleting the glycosylation by chemical and/or enzymatic means), and/or adding one or more glycosylation sites that are not present in the native sequence 84P2A9. In addition, the phrase includes qualitative changes in the glycosylation of the native proteins, involving a change in the nature and proportions of the various carbohydrate moieties present. Another type of covalent modification of 84P2A9 comprises lining the 84P2A9 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The 84P2A9 of the present invention can also be modified in a way to form a chimeric molecule comprising 84P2A9 fused to another, heterologous polypeptide or amino acid sequence. Such a chimeric molecule can be synthesized chemically or recombinantly. A chimeric molecule can have a protein of the invention fused to another tumor-associated antigen or fragment thereof, or can comprise fusion of fragments of the 84P2A9 sequence (amino or nucleic acid) such that a molecule is created that is not, through its length, directly homologous to the amino or nucleic acid sequences respectively of FIG. 2 (SEQ ID NO:2); such a chimeric molecule can comprise multiples of the same subsequence of 84P2A9. A chimeric molecule can comprise a fusion of an 84P2A9-related protein with a polyhistidine epitope tag, which provides an epitope to which immobilized nickel can selectively bind. The epitope tag is generally placed at the amino- or carboxyl-terminus of the 84P2A9. In an alternative embodiment, the chimeric molecule can comprise a fusion of an 84P2A9-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated)

form of an 84P2A9 polypeptide in place of at least one variable region within an Ig molecule. In a particularly preferred embodiment, the immunoglobulin fusion includes the hinge, CH2 and CH3, or the hinge, CHI, CH2 and CH3 regions of an IgGI molecule. For the production of immunoglobulin fusions see also U.S. Pat. No. 5,428,130 issued Jun. 27, 1995.
84P2A9 Antibodies Another aspect of the invention provides antibodies that bind to 84P2A9-related proteins and polypeptides. Preferred antibodies specifically bind to an 84P2A9-related protein and will not bind (or will bind weakly) to non-84P2A9 proteins. In another embodiment, antibodies bind 84P2A9-related proteins as well as the homologs thereof.

84P2A9 Antibodies of the invention are particularly useful in prostate cancer diagnostic and prognostic assays, and imaging methodologies. Similarly, such antibodies are useful in the treatment, diagnosis, and/or prognosis of other cancers, to the extent 84P2A9 is also expressed or overexpressed in other types of cancer. Moreover, intracellularly expressed antibodies (e.g., single chain antibodies) are therapeutically useful in treating cancers in which the expression of 84P2A9 is involved, such as for example advanced and metastatic prostate cancers.

The invention also provides various immunological assays useful for the detection and quantification of 84P2A9 and mutant 84P2A9-related proteins. Such assays can comprise one or more 84P2A9 antibodies capable of recognizing and binding an 84P2A9 or mutant 84P2A9 protein, as appropriate, and are performed within various immunological assay formats well known in the art, including but not limited to various types of radioimmunoassays, enzyme-linked immunosorbent assays (ELISA), enzyme-linked immunofluorescent assays (ELIFA), and the like.

Related immunological but non-antibody assays of the invention also comprise T cell immunogenicity assays (inhibitory or stimulatory) as well as major histocompatibility complex (MHC) binding assays. In addition, immunological imaging methods capable of detecting prostate cancer and other cancers expressing 84P2A9 are also provided by the invention, including but limited to radioscintigraphic imaging methods using labeled 84P2A9 antibodies. Such assays are clinically useful in the detection, monitoring, and prognosis of 84P2A9 expressing cancers such as prostate cancer.

84P2A9 Antibodies can also be used in methods for purifying 84P2A9 and mutant 84P2A9 proteins and polypeptides and for isolating 84P2A9 homologues and related molecules. For example, in one embodiment, the method of purifying an 84P2A9 protein comprises incubating an 84P2A9 antibody, which has been coupled to a solid matrix, with a lysate or other solution containing 84P2A9 under conditions that permit the 84P2A9 antibody to bind to 84P2A9; washing the solid matrix to eliminate impurities; and eluting the 84P2A9 from the coupled antibody. Other uses of the 84P2A9 antibodies of the invention include generating anti-idiotypic antibodies that mimic the 84P2A9 protein.

Various methods for the preparation of antibodies are well known in the art. For example, antibodies can be prepared by immunizing a suitable mammalian host using an 84P2A9-related protein, peptide, or fragment, in isolated or immunoconjugated form (*Antibodies: A Laboratory Manual*, CSH Press, Eds., Harlow, and Lane (1988); Harlow, *Antibodies*, Cold Spring Harbor Press, NY (1989)). In addition, fusion proteins of 84P2A9 can also be used, such as an 84P2A9 GST-fusion protein. In a particular embodiment, a GST fusion protein comprising all or most of the open reading frame amino acid sequence of FIG. 2 is produced and used as an immunogen to generate appropriate antibodies. In another embodiment, an 84P2A9 peptide is synthesized and used as an immunogen.

In addition, naked DNA immunization techniques known in the art are used (with or without purified 84P2A9 protein or 84P2A9 expressing cells) to generate an immune response to the encoded immunogen (for review, see Donnelly, et al., 1997, *Ann. Rev. Immunol.* 15: 617-648).

The amino acid sequence of 84P2A9 as shown in FIG. 2 can be used to select specific regions of the 84P2A9 protein for generating antibodies. For example, hydrophobicity and hydrophilicity analyses of the 84P2A9 amino acid sequence are used to identify hydrophilic regions in the 84P2A9 structure. Regions of the 84P2A9 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Thus, each region identified by any of these programs/methods is within the scope of the present invention. Methods for the generation of 84P2A9 antibodies are further illustrated by way of the examples provided herein.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents are used; in other instances linking reagents such as those supplied by Pierce Chemical Co., Rockford, Ill., are effective. Administration of an 84P2A9 immunogen is conducted generally by injection over a suitable time period and with use of a suitable adjuvant, as is generally understood in the art. During the immunization schedule, titers of antibodies can be taken to determine adequacy of antibody formation.

84P2A9 Monoclonal antibodies can be produced by various means well known in the art. For example, immortalized cell lines that secrete a desired monoclonal antibody are prepared using the standard hybridoma technology of Kohler and Milstein or modifications that immortalize producing B cells, as is generally known. The immortalized cell lines that secrete the desired antibodies are screened by immunoassay in which the antigen is an 84P2A9-related protein. When the appropriate immortalized cell culture secreting the desired antibody is identified, the cells can be expanded and antibodies produced either from in vitro cultures or from ascites fluid.

The antibodies or fragments can also be produced, using current technology, by recombinant means. Regions that bind specifically to the desired regions of the 84P2A9 protein can also be produced in the context of chimeric or complementarity determining region (CDR) grafted antibodies of multiple species origin. Humanized or human 84P2A9 antibodies can also be produced and are preferred for use in therapeutic contexts. Methods for humanizing murine and other non-human antibodies, by substituting one or more of the non-human antibody CDRs for corresponding human antibody sequences, are well known (see for example, Jones, et al., 1986, *Nature* 321: 522-525; Riechmnan, et al., 1988, *Nature* 332: 323-327; Verhoeyen, et al., 1988, *Science* 239: 1534-1536). See also, Carter, et al., 1993, *Proc. Natl. Acad. Sci. USA* 89: 4285 and Sims, et al., 1993, *J. Immunol.* 151: 2296. Methods for producing fully human monoclonal antibodies include phage display and transgenic methods (for review, see Vaughan, et al., 1998, *Nature Biotechnology* 16: 535-539).

Fully human 84P2A9 monoclonal antibodies can be generated using cloning technologies employing large human Ig gene combinatorial libraries (i.e., phage display) (Griffiths and Hoogenboom, "Building an in vitro immune system:

human antibodies from phage display libraries." In: *Protein Engineering of Antibody Molecules for Prophylactic and Therapeutic Applications in Man*. Clark, M. (Ed.), Nottingham Academic, pp 45-64 (1993); Burton and Barbas, *Human Antibodies from Combinatorial Libraries*. Id., pp 65-82). Fully human 84P2A9 monoclonal antibodies can also be produced using transgenic mice engineered to contain human immunoglobulin gene loci as described in PCT Patent Application WO98/24893, Kucherlapati and Jakobovits, et al., published Dec. 3, 1997 (see also, Jakobovits, 1998, *Exp. Opin. Invest. Drugs* 7(4): 607-614). This method avoids the in vitro manipulation required with phage display technology and efficiently produces high affinity authentic human antibodies.

Reactivity of 84P2A9 antibodies with an 84P2A9-related protein can be established by a number of well known means, including Western blot, immunoprecipitation, ELISA, and FACS analyses using, as appropriate, 84P2A9-related proteins, peptides, 84P2A9-expressing cells or extracts thereof.

An 84P2A9 antibody or fragment thereof of the invention is labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 84P2A9 epitopes are generated using methods generally known in the art. Homodimeric antibodies can also be generated by cross-linking techniques known in the art (e.g., Wolff, et al., *Cancer Res.* 53: 2560-2565).

84P2A9 Transgenic Animals

Nucleic acids that encode 84P2A9 or its modified forms can also be used to generate either transgenic animals or "knock out" animals which, in turn; are useful in the development and screening of therapeutically useful reagents. In accordance with established techniques, cDNA encoding 84P2A9 can be used to clone genomic DNA encoding 84P2A9 and the genomic sequences used to generate transgenic animals that contain cells that express DNA encoding 84P2A9. Methods for generating transgenic animals, particularly animals such as mice or rats, have become conventional in the art and are described, for example, in U.S. Pat. Nos. 4,736,866 and 4,870,009. Typically, particular cells would be targeted for 84P2A9 transgene incorporation with tissue-specific enhancers.

Transgenic animals that include a copy of a transgene encoding 84P2A9 can be used to examine the effect of increased expression of DNA encoding 84P2A9. Such animals can be used as tester animals for reagents thought to confer protection from, for example, pathological conditions associated with its overexpression. In accordance with this facet of the invention, an animal is treated with a reagent and a reduced incidence of the pathological condition, compared to untreated animals bearing the transgene, would indicate a potential therapeutic intervention for the pathological condition.

Alternatively, non-human homologues of 84P2A9 can be used to construct an 84P2A9 "knock out" animal that has a defective or altered gene encoding 84P2A9 as a result of homologous recombination between the endogenous gene encoding 84P2A9 and altered genomic DNA encoding 84P2A9 introduced into an embryonic cell of the animal. For example, cDNA encoding 84P2A9 can be used to clone genomic DNA encoding 84P2A9 in accordance with established techniques. A portion of the genomic DNA encoding 84P2A9 can be deleted or replaced with another gene, such as a gene encoding a selectable marker that can be used to monitor integration. Typically, several kilobases of unaltered flanking DNA (both at the 5' and 3' ends) are included in the vector [see, e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see, e.g., Li, et al., *Cell*, 69:915 (1992)]. The selected cells are then injected into a blastocyst of an animal (e.g., a mouse or rat) to form aggregation chimeras [see, e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized for instance, for their ability to defend against certain pathological conditions and for their development of pathological conditions due to absence of the 84P2A9 polypeptide.

Methods for the Detection of 84P2A9

Another aspect of the present invention relates to methods for detecting 84P2A9 polynucleotides and 84P2A9-related proteins and variants thereof, as well as methods for identifying a cell that expresses 84P2A9. 84P2A9 Appears to be expressed in the LAPC xenografts that are derived from lymph-node and bone metastasis of prostate cancer. The expression profile of 84P2A9 makes it a potential diagnostic marker for metastasized disease. In this context, the status of 84P2A9 gene products provide information useful for predicting a variety of factors including susceptibility to advanced stage disease, rate of progression, and/or tumor aggressiveness. As discussed in detail below, the status of 84P2A9 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 84P2A9 polynucleotides in a biological sample, such as serum, bone, prostate, and other tissues, urine, semen, cell preparations, and the like. Detectable 84P2A9 polynucleotides include, for example, an 84P2A9 gene or fragments thereof, 84P2A9 mRNA, alternative splice variant 84P2A9 mRNAs, and recombinant DNA or RNA molecules containing an 84P2A9 polynucleotide. A number of methods for amplifying and/or detecting the presence of 84P2A9 polynucleotides are well known in the art and can be employed in the practice of this aspect of the invention.

In one embodiment, a method for detecting an 84P2A9 mRNA in a biological sample comprises producing cDNA from the sample by reverse transcription using at least one primer; amplifying the cDNA so produced using an 84P2A9 polynucleotides as sense and antisense primers to amplify 84P2A9 cDNAs therein; and detecting the presence of the amplified 84P2A9 cDNA. Optionally, the sequence of the amplified 84P2A9 cDNA can be determined.

In another embodiment, a method of detecting an 84P2A9 gene in a biological sample comprises first isolating genomic DNA from the sample; amplifying the isolated genomic DNA using 84P2A9 polynucleotides as sense and antisense primers to amplify the 84P2A9 gene therein; and detecting the presence of the amplified 84P2A9 gene. Any number of appropriate sense and antisense probe combinations can be designed from the nucleotide sequences provided for the 84P2A9 (FIG. 2) and used for this purpose.

The invention also provides assays for detecting the presence of an 84P2A9 protein in a tissue of other biological sample such as serum, bone, prostate, and other tissues, urine, cell preparations, and the like. Methods for detecting an 84P2A9 protein are also well known and include, for example, immunoprecipitation, immunohistochemical analysis, Western Blot analysis, molecular binding assays, ELISA, ELIFA and the like. For example, in one embodiment, a method of detecting the presence of an 84P2A9 protein in a biological sample comprises first contacting the sample with an 84P2A9 antibody, an 84P2A9-reactive fragment thereof, or a recombinant protein containing an antigen binding region of an 84P2A9 antibody; and then detecting the binding of 84P2A9 protein in the sample thereto.

Methods for identifying a cell that expresses 84P2A9 are also provided. In one embodiment, an assay for identifying a cell that expresses an 84P2A9 gene comprises detecting the presence of 84P2A9 mRNA in the cell. Methods for the detection of particular mRNAs in cells are well known and include, for example, hybridization assays using complementary DNA probes (such as in situ hybridization using labeled 84P2A9 riboprobes, Northern blot and related techniques) and various nucleic acid amplification assays (such as RT-PCR using complementary primers specific for 84P2A9, and other amplification type detection methods, such as, for example, branched DNA, SISBA, TMA and the like). Alternatively, an assay for identifying a cell that expresses an 84P2A9 gene comprises detecting the presence of 84P2A9 protein in the cell or secreted by the cell. Various methods for the detection of proteins are well known in the art and are employed for the detection of 84P2A9 proteins and 84P2A9 expressing cells.

84P2A9 expression analysis is also useful as a tool for identifying and evaluating agents that modulate 84P2A9 gene expression. For example, 84P2A9 expression is significantly upregulated in prostate cancer, and is also expressed in other cancers including prostate, testis, kidney, brain, bone, skin, ovarian, breast, pancreas, colon, lymphocytic and lung cancers. Identification of a molecule or biological agent that could inhibit 84P2A9 expression or over-expression in cancer cells is of therapeutic value. For example, such an agent can be identified by using a screen that quantifies 84P2A9 expression by RT-PCR, nucleic acid hybridization or antibody binding.

Monitoring the Status of 84P2A9 and its Products

Assays that evaluate the status of the 84P2A9 gene and 84P2A9 gene products in an individual can provide information on the growth or oncogenic potential of a biological sample from this individual. For example, because 84P2A9 mRNA is so highly expressed in prostate cancers (as well as the other cancer tissues shown for example in FIGS. 4-8) as compared to normal prostate tissue, assays that evaluate the relative levels of 84P2A9 mRNA transcripts or proteins in a-biological sample can be used to diagnose a disease associated with 84P2A9 dysregulation such as cancer and can provide prognostic information useful in defining appropriate therapeutic options.

Because 84P2A9 is expressed, for example, in various prostate cancer xenograft tissues and cancer cell lines, and cancer patient samples, the expression status of 84P2A9 can provide information useful for determining information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an important aspect of the invention is directed to the various molecular prognostic and diagnostic methods for examining the status of 84P2A9 in biological samples such as those from individuals suffering from, or suspected of suffering from a pathology characterized by dysregulated cellular growth such as cancer.

Oncogenesis is known to be a multistep process where cellular growth becomes progressively dysregulated and cells progress from a normal physiological state to precancerous and then cancerous states (see, e.g., Alers, et al., *Lab Invest.* 77(5): 437-438 (1997) and Isaacs, et al., *Cancer Surv.* 23: 19-32 (1995)). In this context, examining a biological sample for evidence of dysregulated cell growth (such as aberrant 84P2A9 expression in prostate cancers) can allow the early detection of such aberrant cellular physiology before a pathology such as cancer has progressed to a stage at which therapeutic options are more limited. In such examinations, the status of 84P2A9 in a biological sample of interest (such as one suspected of having dysregulated cell growth) can be compared, for example, to the status of 84P2A9 in a corresponding normal sample (e.g., a sample from that individual or alternatively another individual that is not effected by a pathology, for example one not suspected of having dysregulated cell growth). Alterations in the status of 84P2A9 in the biological sample of interest (as compared to the normal sample) provides evidence of dysregulated cellular growth. In addition to using a biological sample that is not effected by a pathology as a normal sample, one can also use a predetermined normative value such as a predetermined normal level of mRNA expression (see, e.g., Grever, et al., *J. Comp. Neurol.* 1996 Dec. 9; 376(2):306-14 and U.S. Pat. No. 5,837,501) to compare 84P2A9 in normal versus suspect samples.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 84P2A9 expressing cells) as well as the, level, and biological activity of expressed gene products (such as 84P2A9 mRNA polynucleotides and polypeptides). Alterations in the status of 84P2A9 can be evaluated by a wide variety of methodologies well known in the art, typically those discussed herein. Typically an alteration in the status of 84P2A9 comprises a change in the location of 84P2A9 and/or 84P2A9 expressing cells and/or an increase in 84P2A9 mRNA and/or protein expression.

As discussed in detail herein, in order to identify a condition or phenomenon associated with dysregulated cell growth, the status of 84P2A9 in a biological simple is evaluated by a number of methods utilized by skilled artisans including, but not limited to genomic Southern analysis (to examine, for example perturbations in the 84P2A9 gene), Northern analysis and/or PCR analysis of 84P2A9 mRNA (to examine, for example alterations in the polynucleotide sequences or expression levels of 84P2A9 mRNAs), and Western and/or immunohistochemical analysis (to examine, for example alterations in polypeptide sequences, alterations in polypeptide localization within a sample, alterations in expression levels of 84P2A9 proteins and/or associations of 84P2A9 proteins with polypeptide binding partners). Detectable 84P2A9 polynucleotides include, for example, an 84P2A9 gene or fragments thereof, 84P2A9 mRNA, alternative splice variants 84P2A9 mRNAs, and recombinant DNA or RNA molecules containing an 84P2A9 polynucleotide.

The expression profile of 84P2A9 makes it a diagnostic marker for local and/or metastasized disease. In particular, the status of 84P2A9 provides information useful for predicting susceptibility to particular disease stages, progression, and/or tumor aggressiveness. The invention provides methods and assays for determining 84P2A9 status and diagnosing cancers that express 84P2A9, such as cancers of the prostate, bladder, testis, ovaries, breast, pancreas, colon and lung. 84P2A9 Status in patient samples can be analyzed by a number of means well known in the art including without limitation, immunohistochemical analysis, in situ hybridization, RT-PCR analysis on laser capture micro-dissected samples, Western blot analysis of clinical samples and cell lines, and tissue array analysis. Typical protocols for evaluating the status of the 84P2A9 gene and gene products can be found, for example in Ausubul, et al. eds., 1995, *Current Protocols In Molecular Biology*, Units 2 [Northern Blotting], 4 [Southern Blotting], 15 [Immunoblotting] and 18 [PCR Analysis].

As described above, the status of 84P2A9 in a biological sample can be examined by a number of well known procedures in the art. For example, the status of 84P2A9 in a biological sample taken from a specific location in the body can be examined by evaluating the sample for the presence or absence of 84P2A9 expressing cells (e.g., those that express 84P2A9 mRNAs or proteins). This examination can provide evidence of dysregulated cellular growth, for example, when 84P2A9 expressing cells are found in a biological sample that does not normally contain such cells (such as a lymph node). Such alterations in the status of 84P2A9 in a biological sample are often associated with dysregulated cellular growth. Specifically, one indicator of dysregulated cellular growth is the metastases of cancer cells from an organ of origin (such as the testis or prostate gland) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy, et al., *Prostate* 42(4): 315-317 (2000); Su, et al., *Semin. Surg. Oncol.* 18(1): 17-28 (2000) and Freeman, et al., *J Urol* 1995 August; 154(2 Pt 1):474-8).

In one aspect, the invention provides methods for monitoring 84P2A9 gene products by determining the status of 84P2A9 gene products expressed by cells in a test tissue sample from an individual suspected of having a disease associated with dysregulated cell growth (such as hyperplasia or cancer) and then comparing the status so determined to the status of 84P2A9 gene products in a corresponding normal sample, the presence of aberrant 84P2A9 gene products in the test sample relative to the normal sample providing an indication of the presence of dysregulated cell growth within the cells of the individual.

In another aspect, the invention provides assays useful in determining the presence of cancer in an individual comprising detecting a significant increase in 84P2A9 mRNA or protein expression in a test cell or tissue sample relative to expression levels in the corresponding normal cell or tissue. The presence of 84P2A9 mRNA can, for example, be evaluated in tissue samples including but not limited to prostate, testis, kidney, brain, bone, skin, ovarian, breast, pancreas, colon, lymphocytic and lung tissues (see, e.g., FIGS. 4-8). The presence of significant 84P2A9 expression in any of these tissues is useful to indicate the emergence, presence and/or severity of a cancer, since the corresponding normal tissues do not express 84P2A9 mRNA or express it at lower levels.

In a related embodiment, 84P2A9 status is determined at the protein level rather than at the nucleic acid level. For example, such a method or assay comprises determining the level of 84P2A9 protein expressed by cells in a test tissue sample and comparing the level so determined to the level of 84P2A9 expressed in a corresponding normal sample. In one embodiment, the presence of 84P2A9 protein is evaluated, for example, using immunohistochemical methods. 84P2A9 Antibodies or binding partners capable of detecting 84P2A9 protein expression are used in a variety of assay formats well known in the art for this purpose.

In other related embodiments, one can evaluate the status 84P2A9 nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see, e.g., Marrogi, et al., 1999, *J. Cutan. Pathol.* 26(8):369-378). For example, a mutation is the sequence of 84P2A9 may be indicative of the presence or promotion of a tumor. Such assays can therefore have diagnostic and predictive value where a mutation in 84P2A9 indicates a potential loss of function or increase in tumor growth.

A wide variety of assays for observing perturbations in nucleotide and amino acid sequences are well known in the art. For example, the size and structure of nucleic acid or amino acid sequences of 84P2A9 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 and 5,952,170).

In another embodiment, one can examine the methylation status of the 84P2A9 gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo, et al., *Am. J. Pathol.* 155(6): 1985-1992 (1999)). In addition, this alteration is present in at least 70% of cases of high-grade prostatic intraepithelial neoplasia (PIN) (Brooks, et al., *Cancer Epidemiol. Biomarkers Prev.*, 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe, et al., *Int. J. Cancer* 76(6): 903-908 (1998)). In this context, a variety of assays for examining methylation status of a gene are well known in the art. For example, one can utilize, in Southern hybridization approaches, methylation-sensitive restriction enzymes which can not cleave sequences that contain methylated CpG sites, in order to assess the overall methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA.

Protocols involving methylation interference can also be found for example in *Current Protocols In Molecular Biology*, Units 12, Frederick M. Ausubul, et al. eds., 1995.

Gene amplification provides an additional method of assessing the status of 84P2A9, a locus that maps to 1q32.3, a region shown to be perturbed in a variety of cancers. Gene amplification is measured in a sample directly, for example, by conventional Southern blotting or Northern blotting to quantitate the transcription of mRNA (Thomas, 1980, *Proc. Natl. Acad. Sci. USA*, 77:5201-5205), dot blotting DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

In addition to the tissues discussed herein, biopsied tissue or peripheral blood can be conveniently assayed for the presence of cancer cells, including but not limited to prostate, testis, kidney, brain, bone, skin, ovarian, breast, pancreas, colon, lymphocytic and lung cancers using for example, Northern, dot blot or RT-PCR analysis to detect 84P2A9 expression (see, e.g., FIGS. 4-8). The presence of RT-PCR amplifiable 84P2A9 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik, et al., 1997, *Urol. Res.* 25:373-384; Ghossein, et al., 1995, *J. Clin. Oncol.* 13:1195-2000; Heston, et al., 1995, *Clin. Chem.* 41:1687-1688). RT-PCR assays are well known in the art.

A related aspect of the invention is directed to predicting susceptibility to developing cancer in an individual. In one embodiment, a method for predicting susceptibility to cancer comprises detecting 84P2A9 mRNA or 84P2A9 protein in a tissue sample, its presence indicating susceptibility to cancer, wherein the degree of 84P2A9 mRNA expression present correlates to the degree of susceptibility. In a specific embodiment, the presence of 84P2A9 in prostate or other tissue is examined, with the presence of 84P2A9 in the sample providing an indication of prostate cancer susceptibility (or the emergence or existence of a prostate tumor). In a closely related embodiment, one can evaluate the integrity 84P2A9 nucleotide and amino acid sequences in a biological sample in order to identify perturbations in the structure of these molecules such as insertions, deletions, substitutions and the like, with the presence of one or more perturbations in 84P2A9 gene products in the sample providing an indication of cancer susceptibility (or the emergence or existence of a tumor).

Another related aspect of the invention is directed to methods for gauging tumor aggressiveness. In one embodiment, a method for gauging aggressiveness of a tumor comprises determining the level of 84P2A9 mRNA or 84P2A9 protein expressed by cells in a sample of the tumor, comparing the level so determined to the level of 84P2A9 mRNA or 84P2A9 protein expressed in a corresponding normal tissue taken from the same individual or a normal tissue reference sample, wherein the degree of 84P2A9 mRNA or 84P2A9 protein expression in the tumor sample relative to the normal sample indicates the degree of aggressiveness. In a specific embodiment, aggressiveness of a tumor is evaluated by determining the extent to which 84P2A9 is expressed in the tumor cells, with higher expression levels indicating more aggressive tumors. In a closely related embodiment, one can evaluate the integrity of 84P2A9 nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprise determining the level of 84P2A9 mRNA or 84P2A9 protein expressed by cells in a sample of the tumor, comparing the level so determined to the level of 84P2A9 mRNA or 84P2A9 protein expressed in an equivalent tissue sample taken from the same individual at a different time, wherein the degree of 84P2A9 mRNA or 84P2A9 protein expression in the tumor sample over time provides information on the progression of the cancer. In a specific embodiment, the progression of a cancer is evaluated by determining the extent to which 84P2A9 expression in the tumor cells alters over time, with higher expression levels indicating a progression of the cancer. Also, one can evaluate the integrity 84P2A9 nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches can be combined with any one of a wide variety of prognostic and diagnostic protocols known in the art. For example, another embodiment of the invention disclosed herein is directed to methods for observing a coincidence between the expression of 84P2A9 gene and 84P2A9 gene products (or perturbations in 84P2A9 gene and 84P2A9 gene products) and a factor that is associated with malignancy as a means of diagnosing and prognosticating the status of a tissue sample. In this context, a wide variety of factors associated with malignancy can be utilized such as the expression of genes associated with malignancy (e.g., PSA, PSCA and PSM expression for prostate cancer, etc.) as well as gross cytological observations (see, e.g., Bocking, et al., 1984, *Anal. Quant. Cytol.* 6(2):74-88; Eptsein, 1995, *Hum. Pathol.* 26(2):223-9; Thorson, et al., 1998, *Mod. Pathol.* 11(6):543-51; Baisden, et al., 1999, *Am. J. Surg. Pathol.* 23(8):918-24). Methods for observing a coincidence between the expression of 84P2A9 gene and 84P2A9 gene products (or perturbations in 84P2A9 gene and 84P2A9 gene products) and an additional factor that is associated with malignancy are useful, for example, because the presence of a set of specific factors that coincide with disease provides information crucial for diagnosing and prognosticating the status of a tissue sample.

In a typical embodiment, methods for observing a coincidence between the expression of 84P2A9 gene and 84P2A9 gene products (or perturbations in 84P2A9 gene and 84P2A9 gene products) and a factor that is associated with malignancy entails detecting the overexpression of 84P2A9 mRNA or protein in a tissue sample, detecting the overexpression of PSA mRNA or protein in a tissue sample, and observing a coincidence of 84P2A9 mRNA or protein and PSA mRNA or protein overexpression. In a specific embodiment, the expression of 84P2A9 and PSA mRNA in prostate tissue is examined. In a preferred embodiment, the coincidence of 84P2A9 and PSA mRNA overexpression in the sample provides an indication of prostate cancer, prostate cancer susceptibility or the emergence or status of a prostate tumor.

Methods for detecting and quantifying the expression of 84P2A9 mRNA or protein are described herein and use of standard nucleic acid and protein detection and quantification technologies is well known in the art. Standard methods for the detection and quantification of 84P2A9 mRNA include in situ hybridization using labeled 84P2A9 riboprobes, Northern blot and related techniques using 84P2A9 polynucleotide probes, RT-PCR analysis using primers specific for 84P2A9, and other amplification type detection methods, such as, for example, branched DNA, SISBA, TMA and the like. In a specific embodiment, semi quantitative RT-PCR is used to detect and quantify 84P2A9 mRNA expression as described in the Examples that follow. Any number of primers capable of amplifying 84P2A9 can be used for this purpose, including but not limited to the various primer sets specifically described herein. Standard methods for the detection and quantification of protein are used for this purpose. In a specific embodiment, polyclonal or monoclonal antibodies specifically reactive with the wild-type 84P2A9 protein can be used in an immunohistochemical assay of biopsied tissue.

Identifying Molecules that Interact with 84P2A9

The 84P2A9 protein sequences disclosed herein allow the skilled artisan to identify proteins, small molecules and other agents that interact with 84P2A9 and pathways activated by 84P2A9 via any one of a variety of art accepted protocols. For example, one can utilize one of the variety of so-called interaction trap systems (also referred to as the "two-hybrid assay"). In such systems, molecules that interact reconstitute a transcription factor which directs expression of a reporter gene, whereupon the expression of the reporter gene is assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with 84P2A9 protein sequences by screening peptide libraries. In such methods, peptides that bind to selected receptor molecules such as 84P2A9 are identified by screening libraries that encode a random or controlled collection of amino acids. Peptides encoded by the libraries are expressed as fusion proteins of bacteriophage coat proteins, the bacteriophage particles are then screened against the receptors of interest.

Accordingly, peptides having a wide variety of uses, such as therapeutic or diagnostic reagents, can thus be identified without any prior information on the structure of the expected ligand or receptor molecule. Typical peptide libraries and screening methods that can be used to identify molecules that interact with 84P2A9 protein sequences are disclosed for example in U.S. Pat. Nos. 5,723,286 and 5,733,731.

Alternatively, cell lines that express 84P2A9 are used to identify protein-protein interactions mediated by 84P2A9. Such interactions can be examined using immunoprecipitation techniques as shown by others (Hamilton B J, et al. *Biochem. Biophys. Res. Commun.* 1999, 261:646-51). Typically 84P2A9 protein can be immunoprecipitated from 84P2A9 expressing prostate cancer cell lines using anti-84P2A9 antibodies. Alternatively, antibodies against His-tag can be used in a cell line engineered to express 84P2A9 (vectors mentioned above). The immunoprecipitated complex can be examined for protein association by procedures such as Western blotting, $^{35}$S-methionine labeling of proteins, protein microsequencing, silver staining and two dimensional gel electrophoresis.

Small molecules that interact with 84P2A9 can be identified through related embodiments of such screening assays. For example, small molecules can be identified that interfere with protein function, including molecules that interfere with 84P2A9's ability to mediate phosphorylation and de-phosphorylation, second messenger signaling and tumorigenesis. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contain a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with an 84P2A9 amino acid sequence shown in FIG. 1 (SEQ ID NO:2), comprising the steps of contacting a population of molecules with the 84P2A9 amino acid sequence, allowing the population of molecules and the 84P2A9 amino acid sequence to interact under conditions that facilitate an interaction, determining the presence of a molecule that interacts with the 84P2A9 amino acid sequence and then separating molecules that do not interact with the 84P2A9 amino acid sequence from molecules that do interact with the 84P2A9 amino acid sequence. In a specific embodiment, the method further includes purifying a molecule that interacts with the 84P2A9 amino acid sequence. In a preferred embodiment, the 84P2A9 amino acid sequence is contacted with a library of peptides.

Therapeutic Methods and Compositions

The identification of 84P2A9 as a protein that is normally prostate and testis-related and which is also expressed in cancers of the prostate (and other cancers), opens a number of therapeutic approaches to the treatment of such cancers. As discussed herein, it is possible that 84P2A9 functions as a transcription factor involved in activating tumor-promoting genes or repressing genes that block tumorigenesis.

The expression profile of 84P2A9 is reminiscent of the Cancer-Testis (CT) antigens or MAGE antigens, which are testis-related genes that are up-regulated in melanomas and other cancers (Van den Eynde and Boon, *Int J Clin Lab Res.* 27:81-86, 1997). Due to their tissue-specific expression and high expression levels in cancer, the MAGE antigens are currently being investigated as targets for cancer vaccines (Durrant, *Anticancer Drugs* 8:727-733, 1997; Reynolds, et al., *Int J Cancer* 72:972-976, 1997). The expression pattern of 84P2A9 provides evidence that it is likewise an ideal target for a cancer vaccine approach to prostate cancer. Its structural features indicate that it may be a transcription factor, and provide evidence that 84P2A9 is a small molecule target.

Accordingly, therapeutic approaches aimed at inhibiting the activity of the 84P2A9 protein are expected to be useful for patients suffering from prostate cancer, testicular cancer, and other cancers expressing 84P2A9. These therapeutic approaches generally fall into two classes. One class comprises various methods for inhibiting the binding or association of the 84P2A9 protein with its binding partner or with others proteins. Another class comprises a variety of methods for inhibiting the transcription of the 84P2A9 gene or translation of 84P2A9 mRNA.

84P2A9 as a Target for Antibody-Based Therapy

The structural features of 84P2A9 indicate that this molecule is an attractive target for antibody-based therapeutic strategies. A number of typical antibody strategies are known in the art for targeting both extracellular and intracellular molecules (see, e.g., complement and ADCC mediated killing as well as the use of intrabodies discussed herein). Because 84P2A9 is expressed by cancer cells of various lineages and not by corresponding normal cells, systemic administration of 84P2A9-immunoreactive compositions would be expected to exhibit excellent sensitivity without toxic, non-specific and/or non-target effects caused by binding of the immunotherapy molecule to non-target organs and tissues. Antibodies specifically reactive with domains of 84P2A9 can be useful to treat 84P2A9-expressing cancers systemically, either as conjugates with a toxin or therapeutic agent, or as naked antibodies capable of inhibiting cell proliferation or function.

84P2A9 Antibodies can be introduced into a patient such that the antibody binds to 84P2A9 and modulates or perturbs a function such as an interaction with a binding partner and consequently mediates growth inhibition and/or destruction of the tumor cells and/or inhibits the growth of the tumor cells. Mechanisms by which such antibodies exert a therapeutic effect can include complement-mediated cytolysis, antibody-dependent cellular cytotoxicity, modulating the physiological function of 84P2A9, inhibiting ligand binding or signal transduction pathways, modulating tumor cell differentiation, altering tumor angiogenesis factor profiles, and/or by inducing apoptosis.

Those skilled in the art understand that antibodies can be used to specifically target and bind immunogenic molecules such as an immunogenic region of the 84P2A9 sequence shown in FIG. 1. In addition, skilled artisans understand that it is routine to conjugate antibodies to cytotoxic agents. In this context, skilled artisans understand that when cytotoxic and/or therapeutic agents are delivered directly to cells by conjugating them to antibodies specific for a molecule expressed by that cell (e.g., 84P2A9), it is reasonable to expect that the cytotoxic agent will exert its known biological effect (e.g., cytotoxicity) on those cells.

A wide variety of compositions and methods for using antibodies conjugated to cytotoxic agents to kill cells are known in the art. In the context of cancers, typical methods entail administering to an animal having a tumor a biologically effective amount of a conjugate comprising a selected cytotoxic and/or therapeutic agent linked to a targeting agent (e.g., an anti-84P2A9 antibody) that binds to a marker (e.g., 84P2A9) expressed, accessible to binding or localized on the cell surfaces. A typical embodiment consists of a method of delivering a cytotoxic and/or therapeutic agent to a cell expressing 84P2A9 comprising conjugating the cytotoxic agent to an antibody that immunospecifically binds to an 84P2A9 epitope and exposing the cell to the antibody-agent conjugate. Another specific illustrative embodiment consists of a method of treating an individual suspected of suffering from metastasized cancer comprising the step of administering parenterally to said individual a pharmaceutical composition comprising a therapeutically effective amount of an antibody conjugated to a cytotoxic and/or therapeutic agent.

Cancer immunotherapy using anti-84P2A9 antibodies may follow the teachings generated from various approaches that have been successfully employed in the treatment of other types of cancer, including but not limited to colon cancer (Adlen, et al., 1998, *Crit. Rev. Immunol.* 18:133-138), multiple myeloma (Ozaki, et al., 1997, *Blood* 90:3179-3186; Tsunenari, et al., 1997, *Blood* 90:2437-2444), gastric cancer (Kasprzyk, et al., 1992, *Cancer Res.* 52:2771-2776), B-cell lymphoma (Funakoshi, et al., 1996, *J. Immunother. Emphasis Tumor Immunol.* 19:93-101), leukemia (Zhong, et al., 1996, *Leuk. Res.* 20:581-589), colorectal cancer (Moun, et al., 1994, *Cancer Res.* 54:6160-6166; Velders, et al., 1995, *Cancer Res.* 55:4398-4403), and breast cancer (Shepard, et al., 1991, *J. Clin. Immunol.* 11:117-127). Some therapeutic approaches involve conjugation of naked antibody to a toxin, such as the conjugation of $^{131}$I to anti-CD20 antibodies (e.g., Rituxan™, IDEC Pharmaceuticals Corp.), while others involve co-administration of antibodies and other therapeutic agents, such as Herceptin™ (trastuzumab) with paclitaxel (Genentech, Inc.). For treatment of prostate cancer, for example, 84P2A9 antibodies can be administered in conjunction with radiation, chemotherapy or hormone ablation.

Although 84P2A9 antibody therapy is useful for all stages of cancer, antibody therapy is particularly appropriate in advanced or metastatic cancers. Treatment with the antibody therapy of the invention is indicated for patients who have received one or more rounds of chemotherapy, while combining the antibody therapy of the invention with a chemotherapeutic or radiation regimen is preferred for patients who have not received chemotherapeutic treatment Additionally, antibody therapy can enable the use of reduced dosages of concomitant chemotherapy, particularly for patients who do not tolerate the toxicity of the chemotherapeutic agent very well.

It is desirable for some cancer patients to be evaluated for the presence and level of 84P2A9 expression, preferably using immunohistochemical assessments of tumor tissue, quantitative 84P2A9 imaging, or other techniques capable of reliably indicating the presence and degree of 84P2A9 expression. Immunohistochemical analysis of tumor biopsies or surgical specimens is preferred for this purpose. Methods for immunohistochemical analysis of tumor tissues are well known in the art.

Anti-84P2A9 monoclonal antibodies useful in treating prostate and other cancers include those that are capable of initiating a potent immune response against the tumor or those that are directly cytotoxic. In this regard, anti-84P2A9 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-84P2A9 mAbs that exert a direct biological effect on tumor growth are useful in the practice of the invention. Potential mechanisms by which such directly cytotoxic mAbs can act include inhibition of cell growth, modulation of cellular differentiation, modulation of tumor angiogenesis factor profiles, and the induction of apoptosis. The mechanism by which a particular anti-84P2A9 mAb exerts an anti-tumor effect is evaluated using any number of in vitro assays designed to determine cell death such as ADCC, ADMMC, complement-mediated cell lysis, and so forth, as is generally known in the art.

The use of murine or other non-human monoclonal antibodies, or human/mouse chimeric mAbs can induce moderate to strong immune responses in some patients. In some cases, this will result in clearance of the antibody from circulation and reduced efficacy. In the most severe cases, such an immune response can lead to the extensive formation of immune complexes which, potentially, can cause renal failure. Accordingly, preferred monoclonal antibodies used in the practice of the therapeutic methods of the invention are those that are either fully human or humanized and that bind specifically to the target 84P2A9 antigen with high affinity but exhibit low or no antigenicity in the patient.

Therapeutic methods of the invention contemplate the administration of single anti-84P2A9 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, the administration of anti-84P2A9 mAbs can be combined with other therapeutic agents, including but not limited to various chemotherapeutic agents, androgen-blockers, and immune modulators (e.g., IL-2, GM-CSF). The anti-84P2A9 mAbs are administered in their "naked" or unconjugated form, or can have therapeutic agents conjugated to them.

The anti-84P2A9 antibody formulations are administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the anti-84P2A9 antibody preparation via an acceptable route of administration such as intravenous injection (IV), typically at a dose in the range of about 0.1 to about 10 mg/kg body weight. Doses in the range of 10-500 mg mAb per week are effective and well tolerated.

Based on clinical experience with the Herceptin mAb in the treatment of metastatic breast cancer, an initial loading dose of approximately 4 mg/kg patient body weight IV followed by weekly doses of about 2 mg/kg IV of the anti-84P2A9 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. However, as one of skill in the art will understand, various factors will influence the ideal dose regimen in a particular case. Such factors can include, for example, the binding affinity and half life of the Ab or mAbs used, the degree of 84P2A9 expression in the patient, the extent of circulating shed 84P2A9 antigen, the desired steady-state antibody concentration level frequency of treatment, and the influence of chemotherapeutic agents used in combination with the treatment method of the invention, as well as the health status of a particular patient.

Optionally, patients should be evaluated for the levels of 84P2A9 in a given sample (e.g., the levels of circulating 84P2A9 antigen and/or 84P2A9 expressing cells) in order to assist in the determination of the most effective dosing regimen and related factors. Such evaluations are also used for monitoring purposes throughout therapy, and are useful to gauge therapeutic success in combination with evaluating other parameters (such as serum PSA levels in prostate cancer therapy).

Inhibition of 84P2A9 Protein Function

Within the first class of therapeutic approaches, the invention includes various methods and compositions for inhibiting the binding of 84P2A9 to its binding partner or its association with other protein(s) as well as methods for inhibiting 84P2A9 function.

Inhibition of 84P2A9 with Intracellular Antibodies

In one approach, recombinant vectors encoding single chain antibodies that specifically bind to 84P2A9 are introduced into 84P2A9 expressing cells via gene transfer technologies, wherein the encoded single chain anti-84P2A9 antibody is expressed intracellularly, binds to 84P2A9 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment will be focused. This technology has been successfully applied in the art (for review, see Richardson and Marasco, 1995, *TIBTECH vol.* 13). Intrabodies have been shown to virtually eliminate the expression of otherwise abundant cell surface receptors. See, for example, Richardson, et al., 1995, *Proc. Natl. Acad. Sci. USA* 92: 3137-3141; Beerli, et al., 1994, *J. Biol. Chem.* 289: 23931-23936; Deshane, et al., 1994, *Gene Ther.* 1: 332-337.

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well known intracellular trafficking signals are engineered into recombinant polynucleotide vectors encoding such single chain antibodies in order to precisely target the expressed intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 84P2A9 in the nucleus, thereby preventing its activity within the nucleus. Nuclear targeting signals are engineered into such 84P2A9 intrabodies in order to achieve the desired targeting. Such 84P2A9 intrabodies are designed to bind specifically to a particular 84P2A9 domain. In another embodiment, cytosolic intrabodies that specifically bind to the 84P2A9 protein are used to prevent 84P2A9 from gaining access to the nucleus, thereby preventing it from exerting any biological activity within the nucleus (e.g., preventing 84P2A9 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652).

Inhibition of 84P2A9 with Recombinant Proteins

In another approach, recombinant molecules that bind to 84P2A9 thereby prevent or inhibit 84P2A9 from accessing/binding to its binding partner(s) or associating with other protein(s) are used to inhibit 84P2A9 function. Such recombinant molecules can, for example, contain the reactive part(s) of an 84P2A9 specific antibody molecule. In a particular embodiment, the 84P2A9 binding domain of an 84P2A9 binding partner is engineered into a dimeric fusion protein comprising two 84P2A9 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 84P2A9, including but not limited to prostate and testicular cancers, where the dimeric fusion protein specifically binds to 84P2A9 thereby blocking 84P2A9 interaction with a binding partner. Such dimeric fusion proteins are further combined into multimeric proteins using known antibody linking technologies.

Inhibition of 84P2A9 Transcription or Translation

Within the second class of therapeutic approaches, the invention provides various methods and compositions for inhibiting the transcription of the 84P2A9 gene. Similarly, the invention also provides methods and compositions for inhibiting the translation of 84P2A9 mRNA into protein.

In one approach, a method of inhibiting the transcription of the 84P2A9 gene comprises contacting the 84P2A9 gene with an 84P2A9 antisense polynucleotide. In another approach, a method of inhibiting 84P2A9 mRNA translation comprises contacting the 84P2A9 mRNA with an antisense polynucleotide. In another approach, an 84P2A9 specific ribozyme is used to cleave the 84P2A9 message, thereby inhibiting translation. Such antisense and ribozyme based methods can also be directed to the regulatory regions of the 84P2A9 gene, such as the 84P2A9 promoter and/or enhancer elements. Similarly, proteins capable of inhibiting an 84P2A9 gene transcription factor can be used to inhibit 84P2A9 mRNA transcription. The various polynucleotides and compositions useful in the aforementioned methods have been described above. The use of antisense and ribozyme molecules to inhibit transcription and translation is well known in the art.

Other factors that inhibit the transcription of 84P2A9 through interfering with 84P2A9 transcriptional activation are also useful for the treatment of cancers expressing 84P2A9. Similarly, factors that are capable of interfering with 84P2A9 processing are useful for the treatment of cancers expressing 84P2A9. Cancer treatment methods utilizing such factors are also within the scope of the invention.

General Considerations for Therapeutic Strategies

Gene transfer and gene therapy technologies can be used for delivering therapeutic polynucleotide molecules to tumor cells synthesizing 84P2A9 (I.e., antisense, ribozyme, polynucleotides encoding intrabodies and other 84P2A9 inhibitory molecules). A number of gene therapy approaches are known in the am Recombinant vectors encoding 84P2A9 antisense polynucleotides, ribozymes, factors capable of interfering with 84P2A9 transcription, and so forth, can be delivered to target tumor cells using such gene therapy approaches.

The above therapeutic approaches can be combined with any one of a wide variety of surgical chemotherapy or radiation therapy regimens. These therapeutic approaches can enable the use of reduced dosages of chemotherapy and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of 84P2A9 to a binding partner, etc.

In vivo, the effect of an 84P2A9 therapeutic composition can be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein, et al., 1997, *Nature Medicine* 3: 402-408). For example, PCT Patent Application WO98/16628, Sawyers, et al., published Apr. 23, 1998, describes various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like. See, also, the Examples below.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, *Remington's Pharmaceutical Sciences* 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer, and will generally depend on a number of other factors appreciated in the art.

Cancer Vaccines

As noted above, the expression profile of 84P2A9 shows that it is highly expressed in advanced and metastasized prostate cancer. This expression pattern is reminiscent of the Cancer-Testis (CT) antigens or MAGE antigens, which are testis-specific genes that are up-regulated in melanomas and other cancers (Van den Eynde and Boon, *Int J Clin Lab Res.* 27:81-86, 1997). Due to their tissue-specific expression and high expression levels in cancer, the MAGE antigens are currently being investigated as targets for cancer vaccines (Durrant, *Anticancer Drugs* 8:727-733, 1997; Reynolds, et al., *Int J Cancer* 72:972-976, 1997).

The invention further provides cancer vaccines comprising an 84P2A9-related protein or fragment as well as DNA based vaccines. In view of the expression of 84P2A9, cancer vaccines are effective at specifically preventing and/or treating 84P2A9 expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge, et al., 1995, *Int. J. Cancer* 63:231-237; Fong, et al., 1997, *J. Immunol.* 159:3113-3117).

Such methods can be readily practiced by employing an 84P2A9 protein, or fragment thereof, or an 84P2A9-encoding nucleic acid molecule and recombinant vectors capable of expressing and appropriately presenting the 84P2A9 immunogen (which typically comprises a number of humoral or T cell epitopes immunoreactive epitopes). In this context, skilled artisans understand that a wide variety of different vaccine systems for delivery of immunoreactive epitopes are known in the art (see, e.g., Heryln, et al., Ann Med 1999 February; 31(1):66-78; Maruyama, et al., Cancer Immunol Immunother 2000 June; 49(3):123-32). Briefly, such techniques consists of methods of generating an immune response (e.g., a humoral and/or cell mediated response) in a mammal comprising the steps exposing the mammal's immune system to an immunoreactive epitope (e.g., an epitope of the 84P2A9 protein shown in SEQ ID NO:2) so that the mammal generates an immune response that is specific for that epitope (e.g., generates antibodies that specifically recognize that epitope). In a preferred method, the 84P2A9 immunogen contains a biological motif. In a highly preferred embodiment, the 84P2A9 immunogen contains one or more amino acid sequences identified using one of the pertinent analytical techniques well known in the art such as the sequences shown in Table 1.

A wide variety of methods for generating an immune response in a mammal are well known in the art (for example as the first step in the generation of hybridomas). Methods of generating an immune response in a mammal comprise exposing the mammal's immune system to an exogenous immunogenic epitope on a protein (e.g., the 84P2A9 protein of SEQ ID NO:2) so that an immune response is generated. A typical embodiment consists of a method for generating an immune response to 84P2A9 in a host, by contacting the host with a sufficient amount of 84P2A9 or a B cell or cytotoxic T-cell eliciting epitope or analog thereof; and at least one periodic interval thereafter contacting the host with additional 84P2A9 or a B cell or cytotoxic T-cell eliciting epitope or analog thereof. A specific embodiment consists of a method of generating an immune response against an 84P2A9 protein or a multiepitopic peptide comprising administering 84P2A9 immunogen (e.g., the 84P2A9 protein or a peptide fragment thereof, an 84P2A9 fusion protein, etc.) in a vaccine preparation to humans or animals. Typically, such vaccine preparations further contain a suitable adjuvant. (See, e.g., U.S. Pat. No. 6,146,635). A representative variation on these methods consists of a method of generating an immune response in an individual against an 84P2A9 immunogen comprising administering in vivo to muscle or skin of the individual's body a genetic vaccine facilitator such as one selected from the group consisting of: anionic lipids; saponins; lectins; estrogenic compounds; hydroxylated lower alkyls; dimethyl sulfoxide; and urea; and a DNA molecule that is dissociated from an infectious agent and comprises a DNA sequence that encodes the 84P2A9 immunogen, the DNA sequence operatively linked to regulatory sequences which control the expression of the DNA sequence; wherein the DNA molecule is taken up by cells, the DNA sequence is expressed in the cells and an immune response is generated against the immunogen. (See, e.g., U.S. Pat. No. 5,962,428).

In an illustrative example of a specific method for generating an immune response, viral gene delivery systems are used to deliver an 84P2A9-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and Sindbis virus (Restifo, 1996, Curr. Opin. Immunol. 8:658-663). Non-viral delivery systems can also be employed by using naked DNA encoding an 84P2A9 protein or fragment thereof introduced into the patient (e.g., intramuscularly or intradermally) to induce an anti-tumor response. In one embodiment, the full-length human 84P2A9 cDNA is employed. In another embodiment, 84P2A9 nucleic acid molecules encoding specific cytotoxic T lymphocyte (CTL) epitopes can be employed. CTL epitopes can be determined using specific algorithms (e.g., Epimer, Brown University) to identify peptides within an 84P2A9 protein that are capable of optimally binding to specified HLA alleles.

Various ex vivo strategies can also be employed. One approach involves the use of dendritic cells to present 84P2A9 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa, et al., 1996, Prostate 28:65-69; Murphy, et al., 1996, Prostate 29:371-380). Thus, dendritic cells can be used to present 84P2A9 peptides to T cells in the context of MHC class I and II molecules. In one embodiment, autologous dendritic cells are pulsed with 84P2A9 peptides capable of binding to MHC class I and/or class II molecules. In another embodiment, dendritic cells are pulsed with the complete 84P2A9 protein. Yet another, embodiment involves engineering the overexpression of the 84P2A9 gene in dendritic cells using various implementing vectors known in the art, such as adenovirus (Arthur, et al., 1997, Cancer Gene Ther. 4:17-25), retrovirus (Henderson, et al., 1996, Cancer Res. 56:3763-3770), lentivirus, adeno-associated virus, DNA transfection (Ribas, et al., 1997, Cancer Res. 57:2865-2869), or tumor-derived RNA transfection (Ashley, et al., 1997, J. Exp. Med. 186:1177-1182). Cells expressing 84P2A9 can also be engineered to express immune modulators, such as GM-CSF, and used as immunizing agents.

Anti-idiotypic anti-84P2A9 antibodies can also be used in anti-cancer therapy as a vaccine for inducing an immune response to cells expressing an 84P2A9 protein. Specifically, the generation of anti-idiotypic antibodies is well known in the art and can readily be adapted to generate anti-idiotypic anti-84P2A9 antibodies that mimic an epitope on an 84P2A9 protein (see, for example, Wagner, et al., 1997, Hybridoma 16: 33-40; Foon, et al., 1995, J. Clin. Invest 96:334-342; Herlyn, et al., 1996, Cancer Immunol. Immunother. 43:65-76). Such an anti-idiotypic antibody can be used in cancer vaccine strategies.

Genetic immunization methods can be employed to generate prophylactic or therapeutic humoral and cellular immune responses directed against cancer cells expressing 84P2A9. Constructs comprising DNA encoding an 84P2A9-related protein/immunogen and appropriate regulatory sequences can be injected directly into muscle or skin of an individual, such that the cells of the muscle or skin take-up the construct and express the encoded 84P2A9 protein/immunogen. Alternatively, a vaccine comprises an 84P2A9-related protein. Expression of the 84P2A9 protein immunogen results in the generation of prophylactic or therapeutic humoral and cellular immunity against bone, colon, pancreatic, testicular, cervical and ovarian cancers. Various prophylactic and therapeutic genetic immunization techniques known in the art can be used.

Kits

For use in the diagnostic and therapeutic applications described herein, kits are also provided by the invention. Such kits can comprise a carrier being compartmentalized to receive in close confinement one or more containers such as vials, tubes, and the like, each of the container(s) comprising one of the separate elements to be used in the method. For example, the container(s) can comprise a probe that is or can be detectably labeled. Such probe can be an antibody or polynucleotide specific for an 84P2A9-related protein or an 84P2A9 gene or message, respectively. Where the kit utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label can be present on the container to indicate that the composition is used for a specific therapy or non-therapeutic application, and can also indicate directions for either in vivo or in vitro use, such as those described above.

p84P2A9-1 Has been deposited under the requirements of the Budapest Treaty on Jan. 6, 2000 with the American Type Culture Collection (ATCC), 10801 University Blvd., Manassas, Va. 20110-2209 USA, and have been identified as ATCC Accession No. PTA-1151.

EXAMPLES

Various aspects of the invention are further described and illustrated by way of the several examples that follow, none of which are intended to limit the scope of the invention.

Example 1

SSH-Generated Isolation of cDNA Fragment of the 84P2A9 Gene

Materials and Methods
LAPC Xenografts and Human Tissues

LAPC xenografts were obtained from Dr. Charles Sawyers (UCLA) and generated as described (Klein, et al., 1997, *Nature Med.* 3: 402-408). Androgen dependent and independent LAPC-4 xenografts LAPC-4 AD and AI, respectively) and LAPC-9 AD and AI xenografts were grown in male SCID mice and were passaged as small tissue chunks in recipient males. LAPC-4 and -9 AI xenografts were derived from LAPC-4 or -9 AD tumors, respectively. Male mice bearing AD tumors were castrated and maintained for 2-3 months. After the tumors re-grew, the tumors were harvested and passaged in castrated males or in female SCID mice. Human tissues for RNA and protein analyses were obtained from the Human Tissue Resource Center (HTRC) at the UCLA (Los Angeles, Calif.) and from QualTek, Inc. (Santa Barbara, Calif.). A benign prostatic hyperplasia tissue sample was patient-derived.

Cell Lines

Human cell lines (e.g., HeLa) were obtained from the ATCC and were maintained in DMEM with 5% fetal calf serum.

RNA Isolation

Tumor tissue and cell lines were homogenized in TRIzol® reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides
The following HPLC purified oligonucleotides were used:

DPNCDN (cDNA synthesis primer)
(SEQ ID NO: 7)
5'TTTTGATCAAGGTT$_{30}$3'

Adaptor 1:
(SEQ ID NO: 8)
5'CTAATACGACTCACTATAGGGCTCGAGCGGCCGCCCGGGCAG3'

(SEQ ID NO: 9)
3'GGCCCGTCCTAG5'

Adaptor 2:
(SEQ ID NO: 10)
5'GTAATACGACTCACTATAGGGCAGCGTGGTCGCGGCCGAG3'

(SEQ ID NO: 11)
3'CGGCTCCTAG5'

PCR primer 1:
(SEQ ID NO: 12)
5'CTAATACGACTCACTATAGGGC3'

Nested primer (NP)1:
(SEQ ID NO: 13)
5'TCGAGCGGCCGCCCGGGCAGGA3'

Nested primer (NP)2:
(SEQ ID NO: 14)
5'AGCGTGGTCGCGGCCGAGGA3'

Suppression Subtractive Hybridization

Suppression Subtractive Hybridization (SSH) was used to identify cDNAs corresponding to genes that may be differentially expressed in prostate cancer. The SSH reaction utilized cDNA from two LAPC-4 AD xenografts. Specifically, the 84P2A9 SSH sequence was identified from a subtraction where cDNA derived from an LAPC-4 AD tumor, 3 days post-castration, was subtracted from cDNA derived from an LAPC-4 AD tumor grown in an intact male. The LAPC-4 AD xenograft tumor grown in an intact male was used as the source of the "tester" cDNA, while the cDNA from the LAPC-4 AD tumor, 3 days post-castration, was used as the source of the "driver" cDNA.

Double stranded cDNAs corresponding to tester and driver cDNAs were synthesized from 2 µg of poly(A)$^+$ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hours at 37° C. Digested cDNA was extracted with phenol/chloroform (1:1) and ethanol precipitated.

Driver cDNA was generated by combining in a 1:1 ratio Dpn II digested cDNA from the relevant xenograft source (see above) with a mix of digested cDNAs derived from human benign prostatic hyperplasia (BPH), the human cell lines HeLa, 293, A431, Colo205, and mouse liver.

Tester cDNA was generated by diluting 1 µl of Dpn II digested cDNA from the relevant xenograft source (see above) (400 ng) in 5 µl of water. The diluted cDNA (2 µl, 160 ng) was then ligated to 2 µl of Adaptor 1 and Adaptor 2 (10 µM, in separate ligation reactions, in a total volume of 10 µl at 16° C. overnight, using 400 u of T4 DNA ligase (CLON- TECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hours at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format Plasmid DNA was prepared, sequenced, and subjected to nucleic acid homology searches of the GenBank, dbest, and NCI-CGAP databases.

RT-PCR Expression Analysis

First strand cDNAs can be generated from 1 μg of mRNA with oligo (dT)12-18 priming using the Gibco-BRL Superscript Preamplification system. The manufacturer's protocol can be used and included an incubation for 50 min at 42° C. with reverse transcriptase followed by RNAse H treatment at 37° C. for 20 min. After completing the reaction, the volume can be increased to 200 μl with water prior to normalization. First strand cDNAs from 16 different normal human tissues can be obtained from Clontech.

Normalization of the first strand cDNAs from multiple tissues can be performed by using the primers 5'atatcgccgcgctcgtcgtcgacaa3' (SEQ ID NO:15) and 5'agccacacgcagctcattgtagaagg 3' (SEQ ID NO:16) to amplify beta-actin. First strand cDNA (5 μl) can be amplified in a total volume of 50 μl containing 0.4 μM primers, 0.2 μM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five μl of the PCR reaction can be removed at 18, 20, and 22 cycles and used for agarose gel electrophoresis. PCR can be performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. can be carried out for 2 min. After agarose gel electrophoresis, the band intensities of the 283 bp .beta.-actin bands from multiple tissues can be compared by visual inspection. Dilution factors for the first strand cDNAs can be calculated to result in equal .beta.-actin band intensities in all tissues after 22 cycles of PCR. Three rounds of normalization can be required to achieve equal band intensities in all tissues after 22 cycles of PCR.

To determine expression levels of the 84P2A9 gene, 5 μl of normalized first strand cDNA can be analyzed by PCR using 25, 30, and 35 cycles of amplification using primer pairs that can be designed with the assistance of a MIT web site.

Semi quantitative expression analysis can be achieved by comparing the PCR products at cycle numbers that give light band intensities.

Results

Two SSH experiments described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments that had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the SHH clones comprising about 425 bp, showed significant homology to several testis-derived ESTs but no homology to any known gene, and was designated 84P2A9.

Northern expression analysis of first strand cDNAs from 16 normal tissues showed a highly prostate and testis-related expression pattern in adult tissues (FIG. 4).

Example 2

Full Length Cloning of 84P2A9

A full length 84P2A9 cDNA clone (clone 1) of 2347 base pairs (bp) was cloned from an LAPC-4 AD cDNA library (Lambda ZAP Express, Stratagene) (FIG. 2). The cDNA encodes an open reading frame (ORF) of 504 amino acids. Sequence analysis revealed the presence of six potential nuclear localization signals and is predicted to be nuclear using the PSORT program. The protein sequence is homologous to a human brain protein KIAA1152 (39.5% identity over a 337 amino acid region), and exhibits a domain that is homologous to the LUCA15 tumor suppressor protein (64.3% identity over a 42 amino acid region) (GenBank Accession #P52756) (FIG. 3). The 84P2A9 cDNA was deposited on Jan. 5, 2000 with the American Type Culture Collection (ATCC; Manassas, Va.) as plasmid p84P2A9-1, and has been assigned Accession No. PTA-1151.

The 84P2A9 proteins have no homology to any known proteins, but the sequence does overlap with several ESTs derived from testis.

Example 3

84P2A9 Gene Expression Analysis

84P2A9 mRNA expression in normal human tissues was analyzed by Northern blotting of two multiple tissue blots (Clontech; Palo Alto, Calif.), comprising a total of 16 different normal human tissues, using labeled 84P2A9 SSH fragment (Example 1) as a probe. RNA samples were quantitatively normalized with a .beta.-actin probe. The results demonstrated expression of a 2.4 and 4.5 kb transcript in normal testis and prostate (FIG. 4).

To analyze 84P2A9 expression in prostate cancer tissues lines northern blotting was performed on RNA derived from the LAPC xenografts. The results show high levels of 84P2A9 expression in all the xenografts, with the highest levels detected in LAPC-9 AD, LAPC-9 AI (FIG. 4 and FIG. 5). These results provide evidence that 84P2A9 is up-regulated in prostate cancer.

In addition, high levels of expression were detected in brain (PFSK-1, -T98G), bone (HOS, U2-OS), lung (CALU-1, NCI-H82, NCI-H146), and kidney (769-P, A498, CAKI-1, SW839) cancer cell lines (FIG. 5). Moderate expression levels were detected in several pancreatic (PANC-1, BxPC-3, HPAC, CAPAN-1), colon (SK-CO-1, CACO-2, LOVO, COLO-205), bone (SK-ES-1, RD-ES), breast (MCF-7, MDA-MB435s) and testicular cancer (NCCIT) cell lines (FIG. 5).

Figure 6:
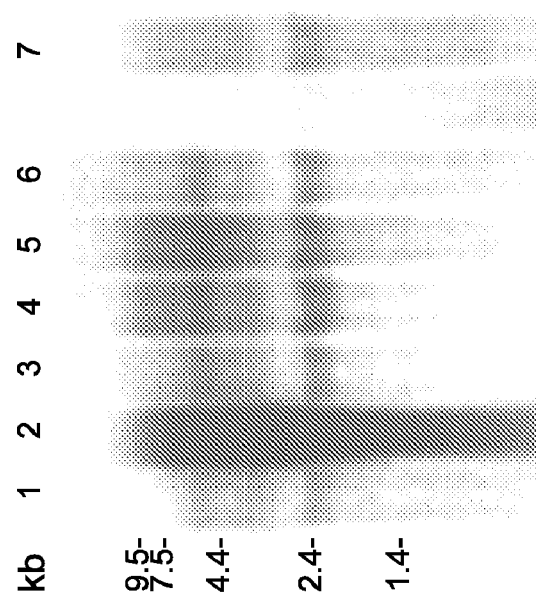
FIG. 6 shows the Northern blot analysis of 84P2A9 expression in prostate cancer patient samples. Prostate cancer patient samples show expression of 84P2A9 in both the normal and the tumor part of the prostate tissues. Lanes 1-7 show Normal prostate, Patient 1 normal adjacent tissue, Patient 1 Gleason 9 tumor, Patient 2 normal adjacent tissue, Patient 2 Gleason 7 tumor and Patient 3 Gleason 7 tumor respectively. These results provide evidence that 84P2A9 is a very testis specific gene that is up-regulated in prostate cancer and potentially other cancers. Similar to the MAGE antigens, 84P2A9 may thus qualify as a cancer-testis antigen (Van den Eynde and Boon, *Int J Clin Lab Res.* 27:81-86, 1997).
Figure 7:
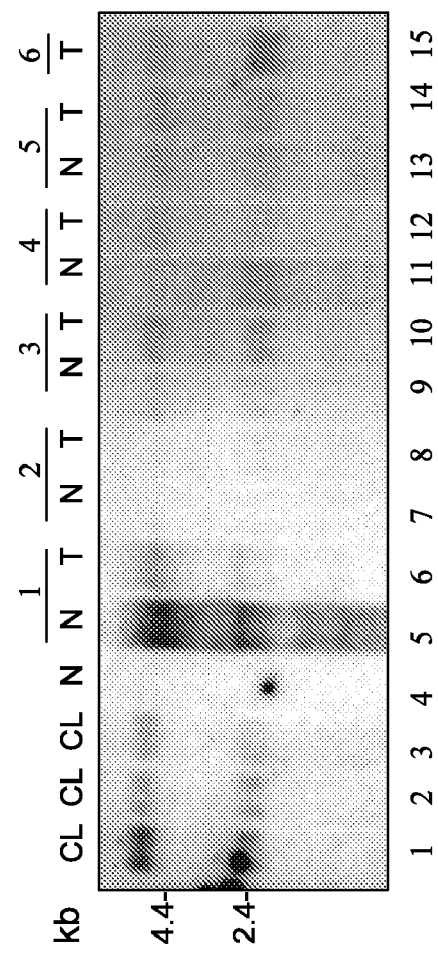
FIG. 7 shows RNA was isolated from kidney cancers (1) and their adjacent normal tissues (N) obtained from kidney cancer patients. Lanes 1-15 show 769-P—clear cell type; A498—clear cell type; SW839—clear cell type; Normal Kidney; Patient 1, N; Patient 1, tumor; Patient 2, N; Patient 2, tumor, clear cell type, grade III; Patient 3, N; Patient 3, tumor, clear cell type, grade II/IV; Patient 4, N; Patient 4, tumor, clear cell type, grade II/IV; Patient 5, N; Patient 5, tumor, clear cell type, grade II; and Patient 6, tumor, metastasis to chest wall respectively (N=normal adjacent tissue and CL=cell line). Northern analysis was performed using 10 μg of total RNA for each sample. Expression of 84P2A9 was seen in all 6 tumor samples tested as well as in the three kidney cell lines, 769-P, A498 and SW839.
Figure 8:
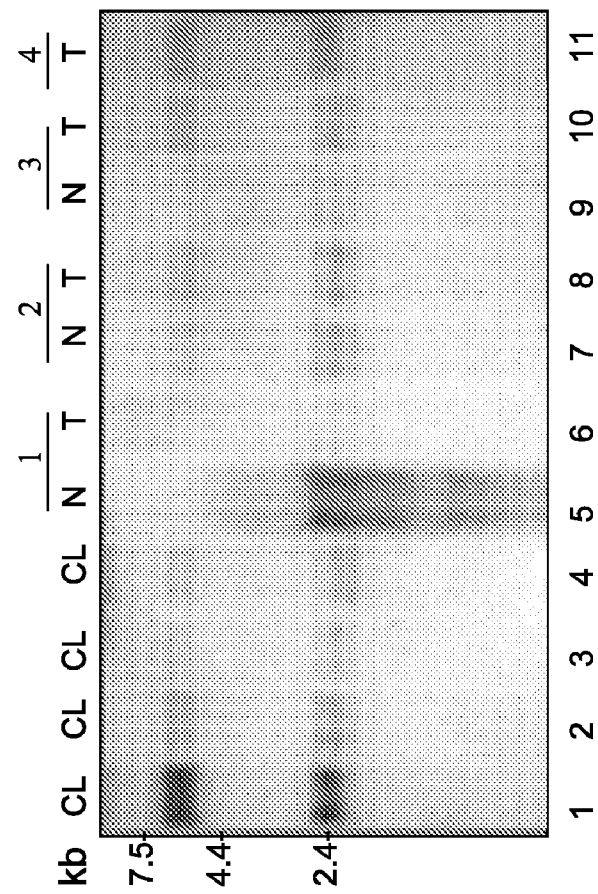
FIG. 8 shows RNA was isolated from colon cancers (1) and their adjacent normal tissues (N) obtained from colon cancer patients. Lanes 1-11 show Colo 205; LoVo; T84; Caco-2; Patient 1, N; Patient 1, tumor, grade 2, T3N1Mx (positive for lymph node metastasis); Patient 2, N; Patient 2, tumor, grade 1, T2N0Mx; Patient 3, N; Patient 3, tumor, grade 1, T2N1Mx (positive for lymph node metastasis); and Patient 4, tumor, grade 2, T3 N1 MX (positive for lymph node metastasis); respectively (N=normal adjacent tissue and CL=cell line). Northern analysis was performed using 10 μg of total RNA for each sample. Expression of 84P2A9 was seen in all 4 tumor samples tested as well as in the 4 colon cancer cell lines Colo 205, LoVo, T84 and Caco-2.
Figure 9:
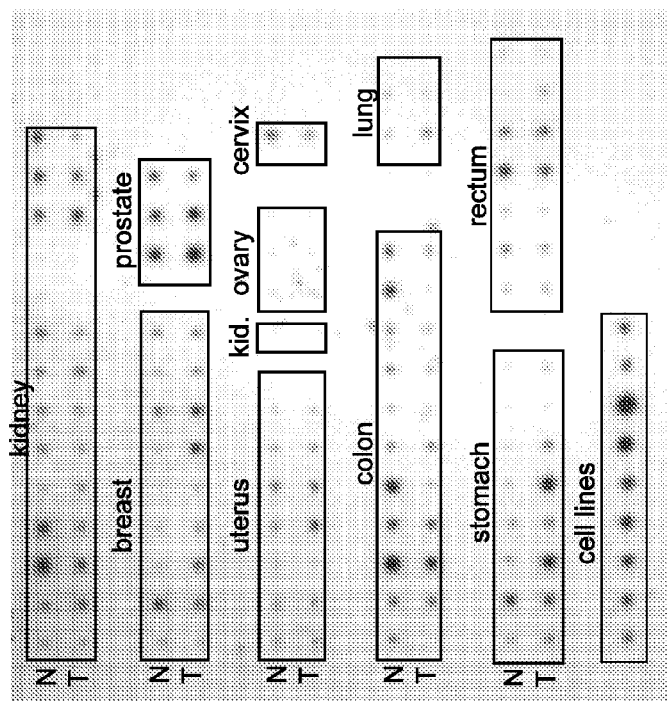
FIG. 9 shows expression of 84P2A9 assayed in a panel of human cancers (T) and their respective matched normal tissues (N) on RNA dot blots. Cancer cell lines from left to right are HeLa (cervical carcinoma), Daudi (Burkitt's lymphoma), K562 (CML), HL-60 (PML), G361 (melanoma), A549 (lung carcinoma), MOLT4 (lymphoblastic leuk.), SW480 (colorectal carcinoma) and Raji (Burkitt's lymphoma). 84P2A9

In addition, prostate cancer patient samples show expression of 84P2A9 in both the normal and the tumor part of the prostate tissues (FIG. 6). These results suggest that 84P2A9 is a very testis specific gene that is up-regulated in prostate cancer and potentially other cancers. Similar to the MAGE antigens, 84P2A9 may thus qualify as a cancer-testis antigen (Van den Eynde and Boon, *Int J Clin Lab Res.* 27:81-86, 1997).

84P2A9 expression in normal tissues can be further analyzed using a multi-tissue RNA dot blot containing different samples (representing mainly normal tissues as well as a few cancer cell lines).

Example 4

Generation of 84P2A9 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Typically a peptide can be designed from a coding region of 84P2A9. Alternatively the immunizing agent may include all or portions of the 84P2A9 protein, or fusion proteins thereof. For example, the 84P2A9 amino acid sequence can be fused to any one of a variety of known fusion protein partners that are well known in the art such as maltose binding protein, LacZ, thioredoxin or an immunoglobulin constant region (see, e.g., *Current Protocols In Molecular Biology*, Volume 2, Unit 16, Frederick M. Ausubul, et al. eds., 1995; Linsley, P. S., Brady, W., Urnes, M., Grosmaire, L., Damle, N., and Ledbetter, L. (1991) *J. Exp. Med.* 174, 561-566). Other such recombinant bacterial proteins include glutathione-S-transferase (GST), and HIS tagged fusion proteins of 84P2A9 (which can be purified from induced bacteria using the appropriate affinity matrix).

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate).

In a typical protocol, rabbits can be initially immunized subcutaneously with about 200 µg of fusion protein or KLH-peptide mixed in complete Freund's adjuvant Rabbits are then injected subcutaneously every two weeks with about 200 µg of immunogen in incomplete Freund's adjuvant. Test bleeds are taken approximately 7-10 days following each immunization and used to monitor the titer of the antiserum by ELISA.

Specificity of the antiserum is tested by Western blot and immunoprecipitation analyses using lysates of genetically engineered cells or cells expressing endogenous 84P2A9. To genetically engineer cells to express 84P2A9, the full length 84P2A9 cDNA can be cloned into an expression vector that provides a 6H is tag at the carboxyl-terminus (pCDNA 3.1 myc-his, InVitrogen). After transfection of the constructs into 293T cells, cell lysates can be immunoprecipitated and Western blotted using anti-His or v5 anti-epitope antibody (Invitrogen) and the anti-84P2A9 serum (see, e.g., FIG. 11). Sera from His-tagged protein and peptide immunized rabbits as well as depleted GST and MBP protein sera are purified by passage over an affinity column composed of the respective immunogen covalently coupled to Affigel matrix (BioRad).

Example 5

Production of Recombinant 84P2A9 in Bacterial and Mammalian Systems

Bacterial Constructs Production of Recombinant 84P2A9 Using pGEX Constructs

To express 84P2A9 in bacterial cells, a portion of 84P2A9 was fused to the Glutathione S-transferase (GST) gene by cloning into pGEX-6P-1 (Amersham Pharmacia Biotech, N.J.). All constructs were made to generate recombinant 84P2A9 protein sequences with GST fused at the N-terminus and a six histidine epitope at the C-terminus. The six histidine epitope tag was generated by adding the histidine codons to the cloning primer at the 3' end of the ORF. A PreScission™ recognition site permits cleavage of the GST tag from 84P2A9. The ampicillin resistance gene and pBR322 origin permits selection and maintenance of the plasmid in *E. coli*. In this construct, a fragment containing amino acids 1 to 151 of 84P2A9 was cloned into pGEX-6P-1. Additional constructs can be made in pGEX-6P-1 spanning regions of the 84P2A9 protein such as amino acids 1 to 504 and amino acids 151 to 504.

Mammalian Constructs

To express recombinant 84P2A9 in mammalian systems, the full length 84P2A9 cDNA can for example, be cloned into an expression vector that provides a 6H is tag at the carboxyl-terminus (pCDNA 3.1 myc-his, InVitrogen). The constructs can be transfected into 293T cells. Transfected 293T cell lysates can be probed with the anti-84P2A9 polyclonal serum described in Example 4 above in a Western blot.

The 84P2A9 genes can also be subcloned into the retroviral expression vector pSR.alpha.MSVtkneo and used to establish 84P2A9 expressing cell lines as follows. The 84P2A9 coding sequence (from translation initiation ATG to the termination codons) is amplified by PCR using ds cDNA template from 84P2A9 cDNA. The PCR product is subcloned into pSR.alpha.MSVtkneo via the EcoR1 (blunt-ended) and Xba 1 restriction sites on the vector and transformed into DH5.alpha. competent cells. Colonies are picked to screen for clones with unique internal restriction sites on the cDNA. The positive clone is confirmed by sequencing of the cDNA insert Retroviruses may thereafter be used for infection and generation of various cell lines using, for example, NIH 3T3, TsuPr1, 293 or rat-1 cells.

Specific mammalian systems are discussed herein.

Production of Recombinant 84P2A9 Using pcDNA3.1/V5-His-TOPO Constructs

To express 84P2A9 in mammalian cells, the 1512 bp (504 amino acid) 84P2A9 ORF along with perfect translational start Kozak consensus sequence was cloned into pcDNA3.1/V5-His-TOPO (Invitrogen, Carlsbad, Calif.). Protein expression is driven from the cytomegalovirus (CMV) promoter. The recombinant protein has the V5 epitope and six histidines fused to the C-terminus. The pcDNA3.1/V5-His-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells expressing the protein and the ampicillin resistance gene and ColE1 origin permits selection and maintenance of the plasmid in *E. coli*.

pSRa Constructs

To generate mammalian cell lines expressing 84P2A9 constitutively, the 1551 bp (517 amino acid) ORF is being cloned into pSRa constructs. Amphotropic and ecotropic retroviruses are generated by transfection of pSRa constructs into the 293T-10A1 packaging line or co-transfection of pSRa and a helper plasmid ((.phi . . . quadrature.) in 293 cells, respectively. The retrovirus can be used to infect a variety of mammalian cell lines, resulting in the integration of the cloned gene, 84P2A9, into the host cell-lines. Protein expression is driven from a long terminal repeat (LTR). The Neomycin resistance gene allows for selection of mammalian cells expressing the protein and the ampicillin resistance gene and ColE1 origin permits selection and maintenance of the plasmid in *E. coli*. Additional pSRa constructs are being made to produce both N-terminal and C-terminal GFP and myc/6 HIS fusion proteins of the fall-length 84P2A9 protein.

Example 6

Production of Recombinant 84P2A9 in a Baculovirus System

To generate a recombinant 84P2A9 protein in a baculovirus expression system, the 84P2A9 cDNA is cloned into the baculovirus transfer vector pBlueBac 4.5 (Invitrogen), which provides a His-tag at the N-terminus Specifically, pBlueBac-84P2A9 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 84P2A9 protein is then generated by infection of HighFive insect cells (InVitrogen) with the purified baculovirus. Recombinant 84P2A9 protein may be detected using anti-84P2A9 antibody. 84P2A9 Protein may be purified and used in various cell based assays or as immunogen to generate polyclonal and monoclonal antibodies specific for 84P2A9.

Example 7

Chromosomal Mapping of the 84P2A9 Gene

The chromosomal localization of 84P2A9 was determined using the GeneBridge4 radiation hybrid panel (Walter, et al., 1994, *Nat. Genetics* 7:22) (Research Genetics, Huntsville Ala.). The following PCR primers were used to localize 84P2A9:

84P2A9.1 gacttcactgatgcgatggtaggt (SEQ ID NO:17)
84P2A9.2 gtcaatactttccgatgctttgct (SEQ ID NO:18)

The resulting mapping vector for the 93 radiation hybrid panel DNAs was: 0000100011001011001000001100010010010010010010010010010010010010010010000100000100000010000. The gene for 84P2A9 was mapped to chromosome 1q32.3 (D1S1602-D1S217).

Example 8

Identification of Potential Signal Transduction Pathways

To determine whether 84P2A9 directly or indirectly activates known signal transduction pathways in cells, luciferase auc) based transcriptional reporter assays are carried out in cells expressing 84P2A9. These transcriptional reporters contain consensus binding sites for known transcription factors that lie downstream of well characterized signal transduction pathways. The reporters and examples of there associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MIAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress 84P2A9-mediated effects may be assayed in cells showing mRNA expression. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 9

Generation of 84P2A9 Monoclonal Antibodies

To generate MAbs to 84P2A9, typically Balb C mice are immunized intraperitoneally with about 10-50 µg of protein immunogen mixed in complete Freund's adjuvant. Protein immunogens include bacterial and baculovirus produced recombinant 84P2A9 proteins and mammalian expressed human IgG FC fusion proteins. Mice are then subsequently immunized every 2-4 weeks with 10-50 µg of antigen mixed in Freund's incomplete adjuvant. Alternatively, Ribi adjuvant is used for initial immunizations. In addition, a DNA-based immunization protocol is used in which a mammalian expression vector such as pCDNA 3.1 encoding the 84P2A9 cDNA alone or as an IgG FC fusion is used to immunize mice by direct injection of the plasmid DNA. This protocol is used alone and in combination with protein immunogens. Test bleeds are taken 7-10 following immunization to monitor titer and specificity of the immune response. Once appropriate reactivity and specificity is obtained as determined by ELISA, Western blotting, and immunoprecipitation analyses, fusion and hybridoma generation is then carried with established procedures well known in the art (Harlow and Lane, 1988).

In a typical specific protocol, a glutathione-S-transferase (GST) fusion protein encompassing an 84P2A9 protein is synthesized and used as immunogen. Balb C mice are initially immunized intraperitoneally with 10-50 μg of the GST-84P2A9 fusion protein mixed in complete Freund's adjuvant Mice are subsequently immunized every 2 weeks with 10-50 μg of GST-84P2A9 protein mixed in Freund's incomplete adjuvant for a total of 3 immunizations. Reactivity of serum from immunized mice to full length 84P2A9 protein is monitored by ELISA using a partially purified preparation of HIS-tagged 84P2A9 protein expressed from 293T cells Example 5). Mice showing the strongest reactivity are rested for 3 weeks and given a final injection of fusion protein in PBS and then sacrificed 4 days later. The spleens of the sacrificed mice are then harvested and fused to SPO/2 myeloma cells using standard procedures (Harlow and Lane, 1988). Supernatants from growth wells following HAT selection are screened by ELISA and Western blot to identify 84P2A9 specific antibody producing clones.

The binding affinity of an 84P2A9 monoclonal antibody may be determined using standard technology. Affinity measurements quantify the strength of antibody to epitope binding and may be used to help define which 84P2A9 monoclonal antibodies are preferred for diagnostic or therapeutic use. The BIAcore system (Uppsala, Sweden) is a preferred method for determining binding affinity. The BIAcore system uses surface plasmon resonance (SPR, Welford K 1991, *Opt. Quant. Elect.* 23:1; Morton and Myszka, 1998, *Methods in Enzymology* 295: 268) to monitor biomolecular interactions in real time. BIAcore analysis conveniently generates association rate constants, dissociation rate constants, equilibrium dissociation constants, and affinity constants.

Example 10

In Vitro Assays of 84P2A9 Function

The expression of 84P2A9 in prostate cancer provides evidence that this gene has a functional role in tumor progression. It is possible that 84P2A9 functions as a transcription factor involved in activating genes involved in tumorigenesis or repressing genes that block tumorigenesis. 84P2A9 Function can be assessed in mammalian cells using in vitro approaches. For mammalian expression, 84P2A9 can be cloned into a number of appropriate vectors, including pcDNA 3.1 myc-His-tag (Example 5) and the retroviral vector pSR.alpha.tkneo (Muller, et al., 1991, MCB 11:1785). Using such expression vectors, 84P2A9 can be expressed in several cell lines, including NIH 3T3, rat-1, TsuPr1 and 293T. Expression of 84P2A9 can be monitored using anti-84P2A9 antibodies (see Examples 4 and 9).

Mammalian cell lines expressing 84P2A9 can be tested in several in vitro and in vivo assays, including cell proliferation in tissue culture, activation of apoptotic signals, tumor formation in SCID mice, and in vitro invasion using a membrane invasion culture system (MICS) (Welch, et al., *Int. J. Cancer* 43: 449-457). 84P2A9 Cell phenotype is compared to the phenotype of cells that lack expression of 84P2A9. The transcriptional effect of 84P2A9 can be tested by evaluating the effect of 84P2A9 on gene expression using gene arrays (Clontech) and transcriptional reporter assays (Stratagene).

Cell lines expressing 84P2A9 can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and 84P2A9 overexpressing PC3, NIH 3T3 and LNCaP cells. To determine whether 84P2A9-expressing cells have chemoattractant properties, indicator cells are monitored for passage through the porous membrane toward a gradient of 84P2A9 conditioned media compared to control media. This assay may also be used to qualify and quantify specific neutralization of the 84P2A9 induced effect by candidate cancer therapeutic compositions.

The function of 84P2A9 can be evaluated using anti-sense RNA technology coupled to the various functional assays described above, e.g., growth, invasion and migration. Antisense RNA oligonucleotides can be introduced into 84P2A9 expressing cells, thereby preventing the expression of 84P2A9. Control and anti-sense containing cells can be analyzed for proliferation, invasion, migration, apoptotic and transcriptional potential. The local as well as systemic effect of the loss of 84P2A9 expression can be evaluated.

Example 11

In Vivo Assay for 84P2A9 Tumor Growth Promotion

The effect of the 84P2A9 protein on tumor cell growth may be evaluated in vivo by gene overexpression in tumor-bearing mice. For example, SCID mice can be injected SQ on each flank with $1 \times 10^6$ of either PC3, TSUPR1, or DU145 cells containing tkNeo empty vector or 84P2A9. At least two strategies may be used: (1) Constitutive 84P2A9 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tet, etc., provided such promoters are compatible with the host cell systems. Tumor volume is then monitored at the appearance of palpable tumors and followed over time to determine if 84P2A9 expressing cells grow at a faster rate and whether tumors produced by 84P2A9-expressing cells demonstrate characteristics of altered aggressiveness (e.g., enhanced metastasis, vasculation, reduced responsiveness to chemotherapeutic drugs). Additionally, mice may be implanted with $1 \times 10^5$ of the same cells orthotopically to determine if 84P2A9 has an effect on local growth in the prostate or on the ability of the cells to metastasize, specifically to lungs, lymph nodes, and bone marrow.

The assay is also useful to determine the 84P2A9 inhibitory effect of candidate therapeutic compositions, such as for example, 84P2A9 intrabodies, 84P2A9 antisense molecules and ribozymes.

Example 12

Western Analysis of 84P2A9 Expression in Subcellular Fractions

Sequence analysis of 84P2A9 revealed the presence of nuclear localization signal. The cellular location of 84P2A9 can be assessed using subcellular fractionation techniques widely used in cellular biology (Storrie B., et al., *Methods Enzymol.* 1990; 182:203-25). Prostate or testis cell lines can be separated into nuclear, cytosolic and membrane fractions. The expression of 84P2A9 in the different fractions can be tested using Western blotting techniques.

Alternatively, to determine the subcellular localization of 84P2A9, 293T cells can be transfected with an expression vector encoding HIS-tagged 84P2A9 (PcDNA 3.1 MYC/HIS, Invitrogen). The transfected cells can be harvested and subjected to a differential subcellular fractionation protocol as previously described (Pemberton, P. A., et al., 1997, *J of Histochemistry and Cytochemistry*, 45:1697-1706). This protocol separates the cell into fractions enriched for nuclei, heavy membranes (lysosomes, peroxisomes, and mitochondria), light membranes (plasma membrane and endoplasmic reticulum), and soluble proteins.

Throughout this application, various publications are referenced (within parentheses for example). The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE 1

Predicted Binding of Peptides from 84P2A9 Proteins to the Human MHC Class I Molecule HLA-A2

| Rank | Start Position | Subsequence Residue Listing | Score (Estimate of half time of disassociation) |
|---|---|---|---|
| 1 | 300 | SILTGSFPL (SEQ ID NO: 19) | 63.04 |
| 2 | 449 | RMLQNMGWT (SEQ ID NO: 20) | 33.75 |
| 3 | 4 | LVHDLVSAL (SEQ ID NO: 21) | 29.97 |
| 4 | 238 | SLSSTDAGL (SEQ ID NO: 22) | 21.36 |
| 5 | 198 | KIQDEGVVL (SEQ ID NO: 23) | 17.28 |
| 6 | 433 | FVGENAQPI (SEQ ID NO: 24) | 17.22 |
| 7 | 301 | ILTGSFPLM (SEQ ID NO: 25) | 16.05 |
| 8 | 218 | KMECEEQKV (SEQ ID NO: 26) | 11.25 |
| 9 | 480 | KGLGLGFPL (SEQ ID NO: 27) | 10.47 |
| 10 | 461 | GLGRDGKGI (SEQ ID NO: 28) | 10.43 |

TABLE 2

Amino Acid Substitution Matrix
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
|  | 9 | -3 | -4 | -2 | -3 | -3 | -1 | -3 | -1 | -1 | -3 | -3 | -3 | -3 | -1 | -1 | -1 | -2 | -2 | C |
|  |  | 6 | 2 | -3 | -1 | -1 | -3 | -1 | -4 | -3 | 1 | -1 | 0 | -2 | 0 | -1 | -3 | -4 | -3 | D |
|  |  |  | 5 | -3 | -2 | 0 | -3 | 1 | -3 | -2 | 0 | -1 | 2 | 0 | 0 | -1 | -2 | -3 | -2 | E |
|  |  |  |  | 6 | -3 | -1 | 0 | -3 | 0 | 0 | -3 | -4 | -3 | -3 | -2 | -2 | -1 | 1 | 3 | F |
|  |  |  |  |  | 6 | -2 | -4 | -2 | -4 | -3 | 0 | -2 | -2 | -2 | 0 | -2 | -3 | -2 | -3 | G |
|  |  |  |  |  |  | 8 | -3 | -1 | -3 | -2 | 1 | -2 | 0 | 0 | -1 | -2 | -3 | -2 | 2 | H |
|  |  |  |  |  |  |  | 4 | -3 | 2 | 1 | -3 | -3 | -3 | -3 | -2 | -1 | 3 | -3 | -1 | I |
|  |  |  |  |  |  |  |  | 5 | -2 | -1 | 0 | -1 | 1 | 2 | 0 | -1 | -2 | -3 | -2 | K |
|  |  |  |  |  |  |  |  |  | 4 | 2 | -3 | -3 | -2 | -2 | -2 | -1 | 1 | -2 | -1 | L |

TABLE 2-continued

Amino Acid Substitution Matrix Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| | | | | | | | | | | 5 | -2 | -2 | 0 | -1 | -1 | -1 | 1 | -1 | -1 | M |
| | | | | | | | | | | | 6 | -2 | 0 | 0 | 1 | 0 | -3 | -4 | -2 | N |
| | | | | | | | | | | | | 7 | -1 | -2 | -1 | -1 | -2 | -4 | -3 | P |
| | | | | | | | | | | | | | 5 | 1 | 0 | -1 | -2 | -2 | -1 | Q |
| | | | | | | | | | | | | | | 5 | -1 | -1 | -3 | -3 | -2 | R |
| | | | | | | | | | | | | | | | 4 | 1 | -2 | -3 | -2 | S |
| | | | | | | | | | | | | | | | | 5 | 0 | -2 | -2 | T |
| | | | | | | | | | | | | | | | | | 4 | -3 | -1 | V |
| | | | | | | | | | | | | | | | | | | 11 | 2 | W |
| | | | | | | | | | | | | | | | | | | | 7 | Y |

HLA Peptide Motif Search Results

| User Parameters and Scoring Information | |
|---|---|
| method selected to limit number of results | explicit number |
| number of results requested | 30 |
| HLA molecule type selected | A1 |
| length selected for subsequences to be scored | 9 |
| echoing mode selected for input sequence | Y |
| echoing format | Numbered lines |

| User Parameters and Scoring Information | |
|---|---|
| length of user's input peptide sequence | 504 |
| number of subsequence scores calculated | 496 |
| number of top-scoring subsequences reported back in scoring output table | 30 |

TABLES 3-16 provide additional analyses of the predicted binding of peptides from 84P2A9 proteins to various HLA molecules.

TABLE 3A

HLA Peptide Scoring Results - 84P2A9 - A1 9-mers
Each peptide is a portion of SEQ ID NO: 2; each start position is specified, the length of peptide is 9 amino acids, and the end position for each peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 1. | 71 | (SEQ ID NO: 29) | SLEEPSKDY | 45.000 |
| 2. | 469 | (SEQ ID NO: 30) | ISEPIQAMQ | 27.000 |
| 3. | 283 | (SEQ ID NO: 31) | KEDPTELDK | 25.000 |
| 4. | 15 | (SEQ ID NO: 32) | SSEQARGGF | 13.500 |
| 5. | 23 | (SEQ ID NO: 33) | FAETGDHSR | 9.000 |
| 6. | 441 | (SEQ ID NO: 34) | ILENNIGNR | 9.000 |
| 7. | 241 | (SEQ ID NO: 35) | STDAGLFTN | 6.250 |
| 8. | 72 | (SEQ ID NO: 36) | LEEPSKDYR | 4.500 |
| 9. | 233 | (SEQ ID NO: 37) | ESDSSSLSS | 3.750 |
| 10. | 92 | (SEQ ID NO: 38) | DSDDQMLVA | 3.750 |
| 11. | 157 | (SEQ ID NO: 39) | MTQPPEGCR | 2.500 |

TABLE 3A-continued

HLA Peptide Scoring Results - 84P2A9 - A1 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 12. | 413 | (SEQ ID NO: 40) | TGDIKRRRK | 2.500 |
| 13. | 256 | (SEQ ID NO: 41) | DDEQSDWFY | 2.250 |
| 14. | 373 | (SEQ ID NO: 42) | RTEHDQHQL | 2.250 |
| 15. | 309 | (SEQ ID NO: 43) | MSHPSRRGF | 1.500 |
| 16. | 207 | (SEQ ID NO: 44) | ESEETNQTN | 1.350 |
| 17. | 231 | (SEQ ID NO: 45) | MSESDSSSL | 1.350 |
| 18. | 64 | (SEQ ID NO: 46) | LSEGSDSSL | 1.350 |
| 19. | 456 | (SEQ ID NO: 47) | WTPGSGLGR | 1.250 |
| 20. | 375 | (SEQ ID NO: 48) | EHDQHQLLR | 1.250 |
| 21. | 293 | (SEQ ID NO: 49) | VPDPVFESI | 1.250 |
| 22. | 93 | (SEQ ID NO: 50) | SDDQMLVAK | 1.000 |
| 23. | 494 | (SEQ ID NO: 51) | ATTTPNAGK | 1.000 |
| 24. | 208 | (SEQ ID NO: 52) | SEETNQTNK | 0.900 |
| 25. | 205 | (SEQ ID NO: 53) | VLESEETNQ | 0.900 |
| 26. | 79 | (SEQ ID NO: 54) | YRENHNNNK | 0.900 |
| 27. | 11 | (SEQ ID NO: 55) | ALEESSEQA | 0.900 |
| 28. | 226 | (SEQ ID NO: 56) | VSDELMSES | 0.750 |
| 29. | 31 | (SEQ ID NO: 57) | RSISCPLKR | 0.750 |
| 30. | 90 | (SEQ ID NO: 58) | HSDSDDQML | 0.750 |

TABLE 3B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT ACFVGENAQP ILENNIGNRM
451 LQNMGWTPGS GLGRDGKGIS EPIQAMQRPK GLGLGFPLPK STSATTTPNA
501 GKSA
```

HLA Peptide Motif Search Results

| User Parameters and Scoring Information | |
|---|---|
| method selected to limit number of results | explicit number |
| number of results requested | 30 |
| HLA molecule type selected | A1 |
| length selected for subsequences to be scored | 10 |
| echoing mode selected for input sequence | Y |

-continued

| User Parameters and Scoring Information | |
|---|---|
| echoing format | Numbered lines |
| length of user's input peptide sequence | 504 |
| number of subsequence scores calculated | 495 |
| number of top-scoring subsequences reported back in scoring output table | 30 |

TABLE 4A

HLA Peptide Scoring Results - 84P2A9 - A1 10-mers
Each peptide is a portion of SEQ ID NO: 2; each start position is specified, the length of peptide is 10 amino acids, and the end position for each peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 469 | (SEQ ID NO: 59) | ISEPIQAMQR | 675.000 |
| 2. | 92 | (SEQ ID NO: 60) | DSDDQMLVAK | 30.000 |
| 3. | 207 | (SEQ ID NO: 61) | ESEETNQTNK | 27.000 |
| 4. | 168 | (SEQ ID NO: 62) | DMDSDRAYQY | 25.000 |
| 5. | 11 | (SEQ ID NO: 63) | ALEESSEQAR | 9.000 |
| 6. | 71 | (SEQ ID NO: 64) | SLEEPSKDYR | 9.000 |
| 7. | 282 | (SEQ ID NO: 65) | EKEDPTELDK | 4.500 |
| 8. | 166 | (SEQ ID NO: 66) | DQDMDSDRAY | 3.750 |
| 9. | 90 | (SEQ ID NO: 67) | HSDSDDQMLV | 3.570 |
| 10. | 177 | (SEQ ID NO: 68) | YQEFTKNKVK | 2.700 |
| 11. | 144 | (SEQ ID NO: 69) | AVDLPQDISN | 2.500 |
| 12. | 373 | (SEQ ID NO: 70) | RTEHDQHQLL | 2.250 |
| 13. | 33 | (SEQ ID NO: 71) | ISCPLKRQAR | 1.500 |
| 14. | 231 | (SEQ ID NO: 72) | MSESDSSSLS | 1.350 |
| 15. | 15 | (SEQ ID NO: 73) | SSEQARGGFA | 1.350 |
| 16. | 254 | (SEQ ID NO: 74) | QGDDEQSDWF | 1.250 |
| 17. | 255 | (SEQ ID NO: 75) | GDDEQSDWFY | 1.250 |
| 18. | 293 | (SEQ ID NO: 76) | VPDPVFESIL | 1.250 |
| 19. | 173 | (SEQ ID NO: 77) | RAYQYQEFTK | 1.000 |
| 20. | 481 | (SEQ ID NO: 78) | GLGLGFPLPK | 1.000 |
| 21. | 205 | (SEQ ID NO: 79) | VLESEETNQT | 0.900 |
| 22. | 79 | (SEQ ID NO: 80) | YRENHNNNKK | 0.900 |
| 23. | 441 | (SEQ ID NO: 81) | ILENNIGNRM | 0.900 |
| 24. | 23 | (SEQ ID NO: 82) | FAETGDHSRS | 0.900 |
| 25. | 121 | (SEQ ID NO: 83) | ESDFAVDNVG | 0.750 |
| 26. | 233 | (SEQ ID NO: 84) | ESDSSLSST | 0.750 |
| 27. | 409 | (SEQ ID NO: 85) | GSLCTGDIKR | 0.750 |
| 28. | 259 | (SEQ ID NO: 86) | QSDWFYEKES | 0.750 |

TABLE 4A-continued

HLA Peptide Scoring Results - 84P2A9 - A1 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 29. | 70 | (SEQ ID NO: 87) | SSLEEPSKDY | 0.750 |
| 30. | 67 | (SEQ ID NO: 88) | GSDSSLEEPS | 0.750 |

TABLE 4B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT AGFVGENAQP ILENNIGNRM
451 LQNMGWTPGS GLGRDGKGIS EPIQAMQRPK GLGLGFPLPK STSATTTPNA
501 GKSA
```

HLA Peptide Motif Search Results

| User Parameters and Scoring Information | |
|---|---|
| method selected to limit number of results | explicit number |
| number of results requested | 30 |
| HLA molecule type selected | A_0201 |
| length selected for subsequences to be scored | 9 |
| echoing mode selected for input sequence | Y |

-continued

| User Parameters and Scoring Information | |
|---|---|
| echoing format | Numbered lines |
| length of user's input peptide sequence | 504 |
| number of subsequence scores calculated | 496 |
| number of top-scoring subsequences reported back in scoring output table | 30 |

TABLE 5A

HLA Peptide Scoring Results - 84P2A9 - A2 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 1. | 300 | (SEQ ID NO: 89) | SILTGSFPL | 63.035 |
| 2. | 449 | (SEQ ID NO: 90) | RMLQNMGWT | 32.748 |
| 3. | 4 | (SEQ ID NO: 91) | LVHDLVSAL | 29.965 |
| 4. | 238 | (SEQ ID NO: 92) | SLSSTDAGL | 21.362 |

TABLE 5A-continued

HLA Peptide Scoring Results - 84P2A9 - A2 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 5. | 198 | (SEQ ID NO: 93) | KIQDEGVVL | 17.282 |
| 6. | 433 | (SEQ ID NO: 94) | FVGENAQPI | 17.217 |
| 7. | 301 | (SEQ ID NO: 95) | ILTGSFPLM | 16.047 |
| 8. | 218 | (SEQ ID NO: 96) | KMECEEQKV | 11.252 |
| 9. | 480 | (SEQ ID NO: 97) | KGLGLGFPL | 10.474 |
| 10. | 461 | (SEQ ID NO: 98) | GLGRDGKGI | 10.433 |
| 11. | 341 | (SEQ ID NO: 99) | SMVPIPGPV | 6.530 |
| 12. | 468 | (SEQ ID NO: 100) | GISEPIQAM | 6.442 |
| 13. | 405 | (SEQ ID NO: 101) | SMHLGSLCT | 5.382 |
| 14. | 191 | (SEQ ID NO: 102) | KIIRQGPKI | 5.021 |
| 15. | 117 | (SEQ ID NO: 103) | PLWHESDFA | 2.445 |
| 16. | 177 | (SEQ ID NO: 104) | YQEFTKNKV | 2.076 |
| 17. | 454 | (SEQ ID NO: 105) | MGWTPGSGL | 1.968 |
| 18. | 156 | (SEQ ID NO: 106) | TMTQPPEGC | 1.758 |
| 19. | 374 | (SEQ ID NO: 107) | TEHDQHQLL | 1.703 |
| 20. | 52 | (SEQ ID NO: 108) | YNVHHPWET | 1.678 |
| 21. | 474 | (SEQ ID NO: 109) | QAMQRPKGL | 1.098 |
| 22. | 240 | (SEQ ID NO: 110) | SSTDAGLFT | 1.097 |
| 23. | 438 | (SEQ ID NO: 111) | AQPILENNI | 1.058 |
| 24. | 269 | (SEQ ID NO: 112) | GGACGITGV | 1.044 |
| 25. | 143 | (SEQ ID NO: 113) | MAVDLPQDI | 1.010 |
| 26. | 206 | (SEQ ID NO: 114) | LESEETNQT | 1.010 |
| 27. | 173 | (SEQ ID NO: 115) | RAYQYQEFT | 0.893 |
| 28. | 3 | (SEQ ID NO: 116) | ELVHDLVSA | 0.857 |
| 29. | 132 | (SEQ ID NO: 117) | RTLRRRRKV | 0.715 |
| 30. | 266 | (SEQ ID NO: 118) | KESGGACGI | 0.710 |

HLA Peptide Motif Search Results

User Parameters and Scoring Information

| | |
|---|---|
| method selected to limit number of results | explicit number |
| number of results requested | 30 |
| HLA molecule type selected | A_0201 |
| length selected for subsequences to be scored | 10 |
| echoing mode selected for input sequence | Y |

-continued

User Parameters and Scoring Information

| | |
|---|---|
| echoing format | Numbered lines |
| length of user's input peptide sequence | 504 |
| number of subsequence scores calculated | 495 |
| number of top-scoring subsequences reported back in scoring output table | 30 |

TABLE 6A

HLA Peptide Scoring Results - 84P2A9 - A2 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 230 | (SEQ ID NO: 119) | LMSESDSSSL | 107.536 |
| 2. | 63 | (SEQ ID NO: 120) | CLSEGSDSSL | 87.586 |
| 3. | 117 | (SEQ ID NO: 121) | PLWHESDFAV | 73.661 |
| 4. | 453 | (SEQ ID NO: 122) | NMGWTPGSGL | 15.428 |
| 5. | 475 | (SEQ ID NO: 123) | AMQRPKGLGL | 15.428 |
| 6. | 433 | (SEQ ID NO: 124) | FVGENAQPIL | 14.454 |
| 7. | 323 | (SEQ ID NO: 125) | RLHGMSSKNI | 10.433 |
| 8. | 142 | (SEQ ID NO: 126) | RMAVDLPQDI | 7.535 |
| 9. | 483 | (SEQ ID NO: 127) | GLGFPLPKST | 7.452 |
| 10. | 300 | (SEQ ID NO: 128) | SILTGSFPLM | 4.802 |
| 11. | 3 | (SEQ ID NO: 129) | ELVHDLVSAL | 3.685 |
| 12. | 473 | (SEQ ID NO: 130) | IQAMQRPKGL | 3.682 |
| 13. | 292 | (SEQ ID NO: 131) | NVPDPVFESI | 3.485 |
| 14. | 124 | (SEQ ID NO: 132) | FAVDNVGNRT | 1.952 |
| 15. | 334 | (SEQ ID NO: 133) | KSGGTPTSMV | 1.589 |
| 16. | 445 | (SEQ ID NO: 134) | NIGNRMLQNM | 1.571 |
| 17. | 315 | (SEQ ID NO: 135) | RGFQARLSRL | 1.187 |
| 18. | 268 | (SEQ ID NO: 136) | SGGACGITGV | 1.044 |
| 19. | 288 | (SEQ ID NO: 137) | ELDKNVPDPV | 1.022 |
| 20. | 486 | (SEQ ID NO: 138) | FPLPKSTSAT | 0.828 |
| 21. | 205 | (SEQ ID NO: 139) | VLESEETNQT | 0.811 |
| 22. | 402 | (SEQ ID NO: 140) | RQTSMHLGSL | 0.648 |
| 23. | 425 | (SEQ ID NO: 141) | LPGPTTAGFV | 0.552 |
| 24. | 441 | (SEQ ID NO: 142) | ILENNIGNRM | 0.541 |
| 25. | 237 | (SEQ ID NO: 143) | SSLSSTDAGL | 0.516 |
| 26. | 10 | (SEQ ID NO: 144) | SALEESSEQA | 0.513 |
| 27. | 212 | (SEQ ID NO: 145) | NQTNKDKMEC | 0.504 |
| 28. | 301 | (SEQ ID NO: 146) | ILTGSFPLMS | 0.481 |
| 29. | 239 | (SEQ ID NO: 147) | LSSTDAGLFT | 0.455 |
| 30. | 103 | (SEQ ID NO: 148) | RPSSNLNNNV | 0.454 |

TABLE 6B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT AGFVGENAQP ILENNIGNRM
451 LQNMGWTPGS GLGRDGKGIS EPIQAMQRPK GLGLGFPLPK STSATTTPNA
501 GKSA
```

HLA Peptide Motif Search Results

User Parameters and Scoring Information

| | |
|---|---|
| method selected to limit number of results | explicit number |
| number of results requested | 30 |
| HLA molecule type selected | A3 |
| length selected for subsequences to be scored | 9 |
| echoing mode selected for input sequence | Y |
| echoing format | Numbered lines |
| length of user's input peptide sequence | 504 |
| number of subsequence scores calculated | 496 |
| number of top-scoring subsequences reported back in scoring output table | 30 |

TABLE 7A

HLA Peptide Scoring Results - 84P2A9 - A3 9-mers
Each peptide is a portion of SEQ ID NO: 2; each start position is specified, the length of peptide is 9 amino acids, and the end position for each peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 1. | 326 | (SEQ ID NO: 149) | GMSSKNIKK | 120.000 |
| 2. | 245 | (SEQ ID NO: 150) | GLFTNDEGR | 60.000 |
| 3. | 133 | (SEQ ID NO: 151) | TLRRRRKVK | 10.000 |
| 4. | 146 | (SEQ ID NO: 152) | DLPQDISNK | 9.000 |
| 5. | 410 | (SEQ ID NO: 153) | SLCTGDIKR | 8.000 |
| 6. | 107 | (SEQ ID NO: 154) | NLNNNVRGK | 6.000 |
| 7. | 258 | (SEQ ID NO: 155) | EQSDWFYEK | 4.860 |
| 8. | 71 | (SEQ ID NO: 156) | SLEEPSKDY | 4.500 |
| 9. | 381 | (SEQ ID NO: 157) | LLRDNRAER | 4.000 |
| 10. | 441 | (SEQ ID NO: 158) | ILENNIGNR | 1.800 |
| 11. | 494 | (SEQ ID NO: 159) | ATTTPNAGK | 1.500 |
| 12. | 301 | (SEQ ID NO: 160) | ILTGSFPLM | 0.900 |
| 13. | 461 | (SEQ ID NO: 161) | GLGRDGKGI | 0.900 |
| 14. | 128 | (SEQ ID NO: 162) | NVGNRTLRR | 0.800 |

TABLE 7A-continued

HLA Peptide Scoring Results - 84P2A9 - A3 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 15. | 238 | (SEQ ID NO: 163) | SLSSTDAGL | 0.600 |
| 16. | 307 | (SEQ ID NO: 164) | PLMSHPSRR | 0.600 |
| 17. | 456 | (SEQ ID NO: 165) | WTPGSGLGR | 0.600 |
| 18. | 218 | (SEQ ID NO: 166) | KMECEEQKV | 0.600 |
| 19. | 283 | (SEQ ID NO: 167) | KEDPTELDK | 0.540 |
| 20. | 409 | (SEQ ID NO: 168) | GSLCTGDIK | 0.450 |
| 21. | 273 | (SEQ ID NO: 169) | GITGVVPWW | 0.405 |
| 22. | 344 | (SEQ ID NO: 170) | PIPGPVGNK | 0.405 |
| 23. | 184 | (SEQ ID NO: 171) | KVKKRKLKI | 0.360 |
| 24. | 156 | (SEQ ID NO: 172) | TMTQPPEGC | 0.300 |
| 25. | 11 | (SEQ ID NO: 173) | ALEESSEQA | 0.300 |
| 26. | 180 | (SEQ ID NO: 174) | FTKNKVKKR | 0.300 |
| 27. | 35 | (SEQ ID NO: 175) | CPLKRQARK | 0.300 |
| 28. | 459 | (SEQ ID NO: 176) | GSGLGRDGK | 0.300 |
| 29. | 191 | (SEQ ID NO: 177) | KIIRQGPKI | 0.270 |
| 30. | 483 | (SEQ ID NO: 178) | GLGFPLPKS | 0.270 |

TABLE 7B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT AGFVGENAQP ILENNIGNRM
451 LQNMGWTPGS GLGRDGKGIS EPIQAMQRPK GLGLGFPLPK STSATTTPNA
501 GKSA
```

HLA Peptide Motif Search Results

User Parameters and Scoring Information

| | |
|---|---|
| method selected to limit number of results | explicit number |
| number of results requested | 30 |
| HLA molecule type selected | A3 |
| length selected for subsequences to be scored | 10 |
| echoing mode selected for input sequence | Y |

User Parameters and Scoring Information -continued

| | |
|---|---|
| echoing format | Numbered lines |
| length of user's input peptide sequence | 504 |
| number of subsequence scores calculated | 495 |
| number of top-scoring subsequences reported back in scoring output table | 30 |

TABLE 8A

HLA Peptide Scoring Results - 84P2A9 - A3 10-mers
Each peptide is a portion of SEQ ID NO: 2; each start position is specified, the length of peptide is 10 amino acids, and the end position for each peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 481 | (SEQ ID NO: 179) | GLGLGFPLPK | 360.000 |
| 2. | 189 | (SEQ ID NO: 180) | KLKIIRQGPK | 18.000 |
| 3. | 71 | (SEQ ID NO: 181) | SLEEPSKDYR | 6.000 |
| 4. | 11 | (SEQ ID NO: 182) | ALEESSEQAR | 6.000 |
| 5. | 380 | (SEQ ID NO: 183) | QLLRDNRAER | 6.000 |
| 6. | 175 | (SEQ ID NO: 184) | YQYQEFTKNK | 4.500 |
| 7. | 274 | (SEQ ID NO: 185) | ITGVVPWWEK | 4.500 |
| 8. | 133 | (SEQ ID NO: 186) | TLRRRKVKR | 4.000 |
| 9. | 168 | (SEQ ID NO: 187) | DMDSDRAYQY | 3.600 |
| 10. | 173 | (SEQ ID NO: 188) | RAYQYQEFTK | 3.000 |
| 11. | 410 | (SEQ ID NO: 189) | SLCTGDIKRR | 3.000 |
| 12. | 156 | (SEQ ID NO: 190) | TMTQPPEGCR | 1.800 |
| 13. | 146 | (SEQ ID NO: 191) | DLPQDISNKR | 1.800 |
| 14. | 107 | (SEQ ID NO: 192) | NLNNNVRGKR | 1.800 |
| 15. | 475 | (SEQ ID NO: 193) | AMQRPKGLGL | 1.200 |
| 16. | 63 | (SEQ ID NO: 194) | CLSEGSDSSL | 0.900 |
| 17. | 453 | (SEQ ID NO: 195) | NMGWTPGSGL | 0.900 |
| 18. | 230 | (SEQ ID NO: 196) | LMSESDSSSL | 0.900 |
| 19. | 3 | (SEQ ID NO: 197) | ELVHDLVSAL | 0.810 |
| 20. | 132 | (SEQ ID NO: 198) | RTLRRRKVK | 0.750 |
| 21. | 180 | (SEQ ID NO: 199) | FTKNKVKKRK | 0.750 |
| 22. | 343 | (SEQ ID NO: 200) | VPIPGPVGNK | 0.608 |
| 23. | 238 | (SEQ ID NO: 201) | SLSSTDAGLF | 0.600 |
| 24. | 142 | (SEQ ID NO: 202) | RMAVDLPQDI | 0.600 |
| 25. | 257 | (SEQ ID NO: 203) | DEQSDWFYEK | 0.486 |
| 26. | 323 | (SEQ ID NO: 204) | RLHGMSSKNI | 0.450 |
| 27. | 301 | (SEQ ID NO: 205) | ILTGSFPLMS | 0.360 |
| 28. | 117 | (SEQ ID NO: 206) | PLWHESDFAV | 0.300 |

TABLE 8A-continued

HLA Peptide Scoring Results - 84P2A9 - A3 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 29. | 493 | (SEQ ID NO: 207) | SATTTPNAGK | 0.300 |
| 30. | 177 | (SEQ ID NO: 208) | YQEFTKNKVK | 0.300 |

TABLE 8B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT AGFVGENAQP ILENNIGNRM
451 LQNMGWTPGS GLGRDGKGIS EPIQAMQRPK GLGLGFPLPK STSATTTPNA
501 GKSA
```

HLA Peptide Motif Search Results

| User Parameters and Scoring Information | |
|---|---|
| method selected to limit number of results | explicit number |
| number of results requested | 30 |
| HLA molecule type selected | A_1101 |
| length selected for subsequences to be scored | 9 |
| echoing mode selected for input sequence | Y |

-continued

| User Parameters and Scoring Information | |
|---|---|
| echoing format | Numbered lines |
| length of user's input peptide sequence | 504 |
| number of subsequence scores calculated | 496 |
| number of top-scoring subsequences reported back in scoring output table | 30 |

TABLE 9A

HLA Peptide Scoring Results - 84P2A9 - A11 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 1. | 326 | (SEQ ID NO: 209) | GMSSKNIKK | 2.400 |
| 2. | 174 | (SEQ ID NO: 210) | AYQYQEFTK | 1.200 |
| 3. | 494 | (SEQ ID NO: 211) | ATTTPNAGK | 1.000 |
| 4. | 128 | (SEQ ID NO: 212) | NVGNRTLRR | 0.800 |
| 5. | 245 | (SEQ ID NO: 213) | GLFTNDEGR | 0.480 |

TABLE 9A-continued

HLA Peptide Scoring Results - 84P2A9 - A11 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 6. | 456 | (SEQ ID NO: 214) | WTPGSGLGR | 0.400 |
| 7. | 258 | (SEQ ID NO: 215) | EQSDWFYEK | 0.360 |
| 8. | 283 | (SEQ ID NO: 216) | KEDPTELDK | 0.360 |
| 9. | 35 | (SEQ ID NO: 217) | CPLKRQARK | 0.300 |
| 10. | 133 | (SEQ ID NO: 218) | TLRRRRKVK | 0.200 |
| 11. | 176 | (SEQ ID NO: 219) | QYQEFTKNK | 0.200 |
| 12. | 157 | (SEQ ID NO: 220) | MTQPPEGCR | 0.200 |
| 13. | 40 | (SEQ ID NO: 221) | QARKRRGRK | 0.200 |
| 14. | 80 | (SEQ ID NO: 222) | RENHNNNKK | 0.180 |
| 15. | 410 | (SEQ ID NO: 223) | SLCTGDIKR | 0.160 |
| 16. | 210 | (SEQ ID NO: 224) | ETNQTNKDK | 0.150 |
| 17. | 146 | (SEQ ID NO: 225) | DLPQDISNK | 0.120 |
| 18. | 184 | (SEQ ID NO: 226) | KVKKRKLKI | 0.120 |
| 19. | 180 | (SEQ ID NO: 227) | FTKNKVKKR | 0.100 |
| 20. | 409 | (SEQ ID NO: 228) | GSLCTGDIK | 0.090 |
| 21. | 381 | (SEQ ID NO: 229) | LLRDNRAER | 0.080 |
| 22. | 441 | (SEQ ID NO: 230) | ILENNIGNR | 0.080 |
| 23. | 482 | (SEQ ID NO: 231) | LGLGFPLPK | 0.060 |
| 24. | 459 | (SEQ ID NO: 232) | GSGLGRDGK | 0.060 |
| 25. | 275 | (SEQ ID NO: 233) | TGVVPWWEK | 0.060 |
| 26. | 139 | (SEQ ID NO: 234) | KVKRMAVDL | 0.060 |
| 27. | 208 | (SEQ ID NO: 235) | SEETNQTNK | 0.060 |
| 28. | 306 | (SEQ ID NO: 236) | FPLMSHPSR | 0.060 |
| 29. | 178 | (SEQ ID NO: 237) | QEFTKNKVK | 0.060 |
| 30. | 179 | (SEQ ID NO: 238) | EFTKNKVKK | 0.060 |

TABLE 9B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLETND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
```

TABLE 9B-continued

Echoed User Peptide Sequence (length = 504 residues) (SEQ ID NO: 2)

```
351 NKRMVHFSPD SHHHDHWFSP GARTEHDQHQ LLRDNRAERG HKKNCSVRTA

401 SRQTSMHLGS LCTGDIKRRR KAAPLPGPTT AGFVGENAQP ILENNIGNRM

451 LQNMGWTPGS GLGRDGKGIS EPIQAMQRPK GLGLGFPLPK STSATTTPNA

501 GKSA
```

HLA Peptide Motif Search Results

| User Parameters and Scoring Information | |
|---|---|
| method selected to limit number of results | explicit number |
| number of results requested | 30 |
| HLA molecule type selected | A_1101 |
| length selected for subsequences to be scored | 10 |
| echoing mode selected for input sequence | Y |
| echoing format | Numbered lines |
| length of user's input peptide sequence | 504 |
| number of subsequence scores calculated | 495 |
| number of top-scoring subsequences reported back in scoring output table | 30 |

TABLE 10A

HLA Peptide Scoring Results - 84P2A9 - A11 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 173 | (SEQ ID NO: 239) | RAYQYQEFTK | 3.600 |
| 2. | 481 | (SEQ ID NO: 240) | GLGLGFPLPK | 2.400 |
| 3. | 132 | (SEQ ID NO: 241) | RTLRRRRKVK | 2.250 |
| 4. | 274 | (SEQ ID NO: 242) | ITGVVPWWEK | 2.000 |
| 5. | 39 | (SEQ ID NO: 243) | RQARKRRGRK | 1.800 |
| 6. | 189 | (SEQ ID NO: 244) | KLKIIRQGPK | 1.200 |
| 7. | 175 | (SEQ ID NO: 245) | YQYQEFTKNK | 0.600 |
| 8. | 180 | (SEQ ID NO: 246) | FTKNKVKKRK | 0.500 |
| 9. | 177 | (SEQ ID NO: 247) | YQEFTKNKVK | 0.300 |
| 10. | 343 | (SEQ ID NO: 248) | VPIPGPVGNK | 0.300 |
| 11. | 493 | (SEQ ID NO: 249) | SATTTPNAGK | 0.200 |
| 12. | 34 | (SEQ ID NO: 250) | SCPLKRQARK | 0.200 |
| 13. | 178 | (SEQ ID NO: 251) | QEFTKNKVKK | 0.120 |
| 14. | 78 | (SEQ ID NO: 252) | DYRENHNNNK | 0.120 |
| 15. | 380 | (SEQ ID NO: 253) | QLLRDNRAER | 0.120 |
| 16. | 22 | (SEQ ID NO: 254) | GFAETGDHSR | 0.120 |
| 17. | 412 | (SEQ ID NO: 255) | CTGDIKRRRK | 0.100 |
| 18. | 133 | (SEQ ID NO: 256) | TLRRRRKVKR | 0.080 |
| 19. | 71 | (SEQ ID NO: 257) | SLEEPSKDYR | 0.080 |
| 20. | 325 | (SEQ ID NO: 258) | HGMSSKNIKK | 0.080 |
| 21. | 107 | (SEQ ID NO: 259) | NLNNNVRGKR | 0.080 |

TABLE 10A-continued

HLA Peptide Scoring Results - 84P2A9 - A11 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 22. | 11 | (SEQ ID NO: 260) | ALEESSEQAR | 0.080 |
| 23. | 156 | (SEQ ID NO: 261) | TMTQPPEGCR | 0.080 |
| 24. | 182 | (SEQ ID NO: 262) | KNKVKKRKLK | 0.060 |
| 25. | 216 | (SEQ ID NO: 263) | KDKMECEEQK | 0.060 |
| 26. | 383 | (SEQ ID NO: 264) | RDNRAERGHK | 0.060 |
| 27. | 306 | (SEQ ID NO: 265) | FPLMSHPSRR | 0.060 |
| 28. | 128 | (SEQ ID NO: 266) | NVGNRTLRRR | 0.040 |
| 29. | 111 | (SEQ ID NO: 267) | NVRGKRPLWH | 0.040 |
| 30. | 311 | (SEQ ID NO: 268) | HPSRRGFQAR | 0.040 |

TABLE 10B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT AGFVGENAQP ILENNIGNRM
451 LQNMGWTPGS GLGRDKGIS EPIQAMQRPK GLGLGFPLPK STSATTTPNA
501 GKSA
```

HLA Peptide Motif Search Results

| User Parameters and Scoring Information | |
|---|---|
| method selected to limit number of results | explicit number |
| number of results requested | 30 |
| HLA molecule type selected | A24 |
| length selected for subsequences to be scored | 9 |
| echoing mode selected for input sequence | Y |
| echoing format | Numbered lines |

-continued

| User Parameters and Scoring Information | |
|---|---|
| length of user's input peptide sequence | 504 |
| number of subsequence scores calculated | 496 |
| number of top-scoring subsequences reported back in scoring output table | 30 |

TABLE 11A

HLA Peptide Scoring Results - 84P2A9 - A1 10-mers
Each peptide is a portion of SEQ ID NO: 2; each start position is specified, the length of peptide is 10 amino acids, and the end position for each peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 316 | (SEQ ID NO: 269) | GFQARLSRL | 30.000 |
| 2. | 480 | (SEQ ID NO: 270) | KGLGLGFPL | 14.400 |
| 3. | 198 | (SEQ ID NO: 271) | KIQDEGVVL | 14.400 |
| 4. | 373 | (SEQ ID NO: 272) | RTEHDQHQL | 12.000 |
| 5. | 182 | (SEQ ID NO: 273) | KNKVKKRKL | 8.800 |
| 6. | 139 | (SEQ ID NO: 274) | KVKRMAVDL | 8.000 |
| 7. | 263 | (SEQ ID NO: 275) | FYEKESGGA | 7.500 |
| 8. | 78 | (SEQ ID NO: 276) | DYRENHNNN | 7.200 |
| 9. | 300 | (SEQ ID NO: 277) | SILTGSFPL | 6.000 |
| 10. | 474 | (SEQ ID NO: 278) | QAMQRPKGL | 6.000 |
| 11. | 116 | (SEQ ID NO: 279) | RPLWHESDF | 6.000 |
| 12. | 110 | (SEQ ID NO: 280) | NNVRGKRPL | 6.000 |
| 13. | 231 | (SEQ ID NO: 281) | MSESDSSSL | 6.000 |
| 14. | 434 | (SEQ ID NO: 282) | VGENAQPIL | 6.000 |
| 15. | 64 | (SEQ ID NO: 283) | LSEGSDSSL | 6.000 |
| 16. | 443 | (SEQ ID NO: 284) | ENNIGNRML | 6.000 |
| 17. | 4 | (SEQ ID NO: 285) | LVHDLVSAL | 5.760 |
| 18. | 29 | (SEQ ID NO: 286) | HSRSISCPL | 5.600 |
| 19. | 56 | (SEQ ID NO: 287) | HPWETGHCL | 4.800 |
| 20. | 90 | (SEQ ID NO: 288) | HSDSDDQML | 4.800 |
| 21. | 478 | (SEQ ID NO: 289) | RPKGLGLGF | 4.800 |
| 22. | 476 | (SEQ ID NO: 290) | MQRPKGLGL | 4.800 |
| 23. | 400 | (SEQ ID NO: 291) | ASRQTSMHL | 4.000 |
| 24. | 454 | (SEQ ID NO: 292) | MGWTPGSGL | 4.000 |
| 25. | 238 | (SEQ ID NO: 293) | SLSSTDAGL | 4.000 |
| 26. | 403 | (SEQ ID NO: 294) | QTSMHLGSL | 4.000 |
| 27. | 191 | (SEQ ID NO: 295) | KIIRQGPKI | 3.300 |
| 28. | 349 | (SEQ ID NO: 296) | VGNKRMVHF | 3.000 |
| 29. | 15 | (SEQ ID NO: 297) | SSEQARGGF | 3.000 |
| 30. | 143 | (SEQ ID NO: 298) | MAVDLPQDI | 2.592 |

TABLE 11B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR

51 SYNVHHPWET GHCLSEGSDS SLEEPSKDYR ENHNNNKKDH SDSDDQMLVA

101 KRRPSSNLNN NVRGKRPLWH ESDFAVDNVG NRTLRRRRKV KRMAVDLPQD

151 ISNKRTMTQP PEGCRDQDMD SDRAYQYQEF TKNKVKKRKL KIIRQGPKIQ

201 DEGVVLESEE TNQTNKDKME CEEQKVSDEL MSESDSSSLS STDAGLFTND

251 EGRQGDDEQS DWFYEKESGG ACGITGVVPW WEKEDPTELD KNVPDPVFES

301 ILTGSFPLMS HPSRRGFQAR LSRLHGMSSK NIKKSGGTPT SMVPIPGPVG

351 NKRMVHFSPD SHHHDHWFSP GARTEHDQHQ LLRDNRAERG HKKNCSVRTA

401 SRQTSMHLGS LCTGDIKRRR KAAPLPGPTT AGFVGENAQP ILENNIGNRM

451 LQNMGWTPGS GLGRDKGIS EPIQAMQRPK GLGLGFPLPK STSATTTPNA

501 GKSA
```

HLA Peptide Motif Search Results

| User Parameters and Scoring Information | |
|---|---|
| method selected to limit number of results | explicit number |
| number of results requested | 30 |
| HLA molecule type selected | A24 |
| length selected for subsequences to be scored | 10 |
| echoing mode selected for input sequence | Y |

| User Parameters and Scoring Information | |
|---|---|
| echoing format | Numbered lines |
| length of user's input peptide sequence | 504 |
| number of subsequence scores calculated | 495 |
| number of top-scoring subsequences reported back in scoring output table | 30 |

TABLE 12A

HLA Peptide Scoring Results - 84P2A9 - A24 10-mers
Each peptide is a portion of SEQ ID NO: 2; each start position is specified, the length of peptide is 10 amino acids, and the end position for each peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 297 | (SEQ ID NO: 299) | VFESILTGSF | 18.000 |
| 2. | 373 | (SEQ ID NO: 300) | RTEHDQHQLL | 14.400 |
| 3. | 176 | (SEQ ID NO: 301) | QYQEFTKNKV | 11.880 |
| 4. | 174 | (SEQ ID NO: 302) | AYQYQEFTKN | 9.900 |
| 5. | 432 | (SEQ ID NO: 303) | GFVGENAQPI | 9.000 |
| 6. | 51 | (SEQ ID NO: 304) | SYNVHHPWET | 8.250 |
| 7. | 402 | (SEQ ID NO: 305) | RQTSMHLGSL | 8.000 |
| 8. | 315 | (SEQ ID NO: 306) | RGFQARLSRL | 8.000 |
| 9. | 263 | (SEQ ID NO: 307) | FYEKESGGAC | 7.500 |
| 10. | 3 | (SEQ ID NO: 308) | ELVHDLVSAL | 7.200 |
| 11. | 280 | (SEQ ID NO: 309) | WWEKEDPTEL | 6.600 |
| 12. | 237 | (SEQ ID NO: 310) | SSLSSTDAGL | 6.000 |
| 13. | 299 | (SEQ ID NO: 311) | ESILTGSFPL | 6.000 |
| 14. | 475 | (SEQ ID NO: 312) | AMQRPKGLGL | 6.000 |

TABLE 12A-continued

HLA Peptide Scoring Results - 84P2A9 - A24 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 15. | 109 | (SEQ ID NO: 313) | NNNVRGKRPL | 6.000 |
| 16. | 230 | (SEQ ID NO: 314) | LMSESDSSSL | 4.800 |
| 17. | 293 | (SEQ ID NO: 315) | VPDPVFESIL | 4.800 |
| 18. | 433 | (SEQ ID NO: 316) | FVGENAQPIL | 4.800 |
| 19. | 63 | (SEQ ID NO: 317) | CLSEGSDSSL | 4.800 |
| 20. | 125 | (SEQ ID NO: 318) | AVDNVGNRTL | 4.000 |
| 21. | 99 | (SEQ ID NO: 319) | VAKRRPSSNL | 4.000 |
| 22. | 473 | (SEQ ID NO: 320) | IQAMQRPKGL | 4.000 |
| 23. | 453 | (SEQ ID NO: 321) | NMGWTPGSGL | 4.000 |
| 24. | 399 | (SEQ ID NO: 322) | TASRQTSMHL | 4.000 |
| 25. | 292 | (SEQ ID NO: 323) | NVPDPVFESI | 3.024 |
| 26. | 142 | (SEQ ID NO: 324) | RMAVDLPQDI | 2.880 |
| 27. | 437 | (SEQ ID NO: 325) | NAQPILENNI | 2.592 |
| 28. | 254 | (SEQ ID NO: 326) | QGDDEQSDWF | 2.400 |
| 29. | 14 | (SEQ ID NO: 327) | ESSEQARGGF | 2.400 |
| 30. | 323 | (SEQ ID NO: 328) | RLHGMSSKNI | 2.000 |

TABLE 12B

| Echoed User Peptide Sequence (length = 504 residues) (SEQ ID NO: 2) |
|---|
| 1 MEELVHDLVS ALEESSEQAR GGFAETGDHS RSISCPLKRQ ARKRRGRKRR |
| 51 SYNVHHPWET GHCLSEGSDS SLEEPSKDYR ENHNNNKKDH SDSDDQMLVA |
| 101 KRRPSSNLNN NVRGKRPLWH ESDFAVDNVG NRTLRRRRKV KRMAVDLPQD |
| 151 ISNKRTMTQP PEGCRDQDMD SDRAYQYQEF TKNKVKKRKL KIIRQGPKIQ |
| 201 DEGVVLESEE TNQTNKDKME CEEQKVSDEL MSESDSSSLS STDAGLFTND |
| 251 EGRQGDDEQS DWFYEKESGG ACGITGVVPW WEKEDPTELD KNVPDPVFES |
| 301 ILTGSFPLMS HPSRRGFQAR LSRLHGMSSK NIKKSGGTPT SMVPIPGPVG |
| 351 NKRMVHFSPD SHHHDHWFSP GARTEHDQHQ LLRDNRAERG HKKNCSVRTA |
| 401 SRQTSMHLGS LCTGDIKRRR KAAPLPGPTT AGFVGENAQP ILENNIGNRM |
| 451 LQNMGWTPGS GLGRDGKGIS EPIQAMQRPK GLGLGFPLPK STSATTTPNA |
| 501 GKSA |

HLA Peptide Motif Search Results

User Parameters and Scoring Information

| | |
|---|---|
| method selected to limit number of results | explicit number |
| number of results requested | 30 |
| HLA molecule type selected | B7 |
| length selected for subsequences to be scored | 9 |
| echoing mode selected for input sequence | Y |

User Parameters and Scoring Information -continued

| | |
|---|---|
| echoing format | Numbered lines |
| length of user's input peptide sequence | 504 |
| number of subsequence scores calculated | 496 |
| number of top-scoring subsequences reported back in scoring output table | 30 |

TABLE 13A

HLA Peptide Scoring Results - 84P2A9 - B7 9-mers
Each peptide is a portion of SEQ ID NO: 2; each start position is specified, the length of peptide is 9 amino acids, and the end position for each peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 1. | 400 | (SEQ ID NO: 329) | ASRQTSMHL | 120.000 |
| 2. | 56 | (SEQ ID NO: 330) | HPWETGHCL | 80.000 |
| 3. | 476 | (SEQ ID NO: 331) | MQRPKGLGL | 40.000 |
| 4. | 29 | (SEQ ID NO: 332) | HSRSISCPL | 40.000 |
| 5. | 474 | (SEQ ID NO: 333) | QAMQRPKGL | 36.000 |
| 6. | 4 | (SEQ ID NO: 334) | LVHDLVSAL | 20.000 |
| 7. | 139 | (SEQ ID NO: 335) | KVKRMAVDL | 20.000 |
| 8. | 100 | (SEQ ID NO: 336) | AKRRPSSNL | 18.00 |
| 9. | 423 | (SEQ ID NO: 337) | APLPGPTTA | 6.000 |
| 10. | 454 | (SEQ ID NO: 338) | MGWTPGSGL | 6.000 |
| 11. | 396 | (SEQ ID NO: 339) | SVRTASRQT | 5.000 |
| 12. | 196 | (SEQ ID NO: 340) | GPKIQDEGV | 4.000 |
| 13. | 182 | (SEQ ID NO: 341) | KNKVKKRKL | 4.000 |
| 14. | 110 | (SEQ ID NO: 342) | NNVRGKRPL | 4.000 |
| 15. | 198 | (SEQ ID NO: 343) | KIQDEGVVL | 4.000 |
| 16. | 403 | (SEQ ID NO: 344) | QTSMHLGSL | 4.000 |
| 17. | 238 | (SEQ ID NO: 345) | SLSSTDAGL | 4.000 |
| 18. | 285 | (SEQ ID NO: 346) | DPTELDKNV | 4.000 |
| 19. | 300 | (SEQ ID NO: 347) | SILTGSFPL | 4.000 |
| 20. | 347 | (SEQ ID NO: 348) | GPVGNKRMV | 4.000 |
| 21. | 480 | (SEQ ID NO: 349) | KGLGLGFPL | 4.000 |
| 22. | 417 | (SEQ ID NO: 350) | KRRRKAAPL | 4.000 |
| 23. | 443 | (SEQ ID NO: 351) | ENNIGNRML | 4.000 |
| 24. | 313 | (SEQ ID NO: 352) | SRRGFQARL | 4.000 |
| 25. | 18 | (SEQ ID NO: 353) | QARGGFAET | 3.000 |
| 26. | 293 | (SEQ ID NO: 354) | VPDPVFESI | 2.400 |
| 27. | 295 | (SEQ ID NO: 355) | DPVFESILT | 2.000 |
| 28. | 311 | (SEQ ID NO: 356) | HPSRRGFQA | 2.000 |

TABLE 13A-continued

HLA Peptide Scoring Results - 84P2A9 - B7 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 29. | 433 | (SEQ ID NO: 357) | FVGENAQPI | 2.000 |
| 30. | 486 | (SEQ ID NO: 358) | FPLPKSTSA | 2.000 |

TABLE 13B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT AGFVGENAQP ILENNIGNRM
451 LQNMGWTPGS GLGRDGKGIS EPIQAMQRPK GLGLGFPLPK STSATTTPNA
501 GKSA
```

HLA Peptide Motif Search Results

User Parameters and Scoring Information

| | |
|---|---|
| method selected to limit number of results | explicit number |
| number of results requested | 30 |
| HLA molecule type selected | B7 |
| length selected for subsequences to be scored | 10 |
| echoing mode selected for input sequence | Y |

-continued

User Parameters and Scoring Information

| | |
|---|---|
| echoing format | Numbered lines |
| length of user's input peptide sequence | 504 |
| number of subsequence scores calculated | 495 |
| number of top-scoring subsequences reported back in scoring output table | 30 |

TABLE 14A

HLA Peptide Scoring Results - 84P2A9 - B7 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 318 | (SEQ ID NO: 359) | QARLSRLHGM | 30.000 |
| 2. | 293 | (SEQ ID NO: 360) | VPDPVFESIL | 24.000 |
| 3. | 345 | (SEQ ID NO: 361) | IPGPVGNKRM | 20.000 |
| 4. | 433 | (SEQ ID NO: 362) | FVGENAQPIL | 20.000 |
| 5. | 125 | (SEQ ID NO: 363) | AVDNVGNRTL | 18.000 |

TABLE 14A-continued

HLA Peptide Scoring Results - 84P2A9 - B7 10-mers
Each peptide is a portion of SEQ ID NO: 2; each
start position is specified, the length of peptide
is 10 amino acids, and the end position for each
peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 6. | 99 | (SEQ ID NO: 364) | VAKRRPSSNL | 18.000 |
| 7. | 399 | (SEQ ID NO: 365) | TASRQTSMHL | 12.000 |
| 8. | 475 | (SEQ ID NO: 366) | AMQRPKGLGL | 12.000 |
| 9. | 453 | (SEQ ID NO: 367) | NMGWTPGSGL | 6.000 |
| 10. | 230 | (SEQ ID NO: 368) | LMSESDSSSL | 4.000 |
| 11. | 473 | (SEQ ID NO: 369) | IQAMQRPKGL | 4.000 |
| 12. | 312 | (SEQ ID NO: 370) | PSRRGFQARL | 4.000 |
| 13. | 425 | (SEQ ID NO: 371) | LPGPTTAGFV | 4.000 |
| 14. | 103 | (SEQ ID NO: 372) | RPSSNLNNNV | 4.000 |
| 15. | 109 | (SEQ ID NO: 373) | NNNVRGKRPL | 4.000 |
| 16. | 63 | (SEQ ID NO: 374) | CLSEGSDSSL | 4.000 |
| 17. | 315 | (SEQ ID NO: 375) | RGFQARLSRL | 4.000 |
| 18. | 237 | (SEQ ID NO: 376) | SSLSSTDAGL | 4.000 |
| 19. | 416 | (SEQ ID NO: 377) | IKRRRKAAPL | 4.000 |
| 20. | 196 | (SEQ ID NO: 378) | GPKIQDEGVV | 4.000 |
| 21. | 299 | (SEQ ID NO: 379) | ESILTGSFPL | 4.000 |
| 22. | 402 | (SEQ ID NO: 380) | RQTSMHLGSL | 4.000 |
| 23. | 3 | (SEQ ID NO: 381) | ELVHDLVSAL | 4.000 |
| 24. | 147 | (SEQ ID NO: 382) | LPQDISNKRT | 2.000 |
| 25. | 116 | (SEQ ID NO: 383) | RPLWHESDFA | 2.000 |
| 26. | 278 | (SEQ ID NO: 384) | VPWWEKEDPT | 2.000 |
| 27. | 488 | (SEQ ID NO: 385) | LPKSTSATTT | 2.000 |
| 28. | 292 | (SEQ ID NO: 386) | NVPDPVFESI | 2.000 |
| 29. | 45 | (SEQ ID NO: 387) | RGRKRRSYNV | 2.000 |
| 30. | 486 | (SEQ ID NO: 388) | FPLPKSTSAT | 2.000 |

TABLE 14B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR

51 SYNVHHPWET GHCLSEGSDS SLEEPSKDYR ENHNNNKKDH SDSDDQMLVA

101 KRRPSSNLNN NVRGKRPLWH ESDFAVDNVG NRTLRRRRKV KRMAVDLPQD

151 ISNKRTMTQP PEGCRDQDMD SDRAYQYQEF TKNKVKKRKL KIIRQGPKIQ

201 DEGVVLESEE TNQTNKDKME CEEQKVSDEL MSESDSSSLS STDAGLFTND

251 EGRQGDDEQS DWFYEKESGG ACGITGVVPW WEKEDPTELD KNVPDPVFES

301 ILTGSFPLMS HPSRRGFQAR LSRLHGMSSK NIKKSGGTPT SMVPIPGPVG
```

TABLE 14B-continued

Echoed User Peptide Sequence (length = 504 residues) (SEQ ID NO: 2)

```
351 NKRMVHFSPD SHHHDHWFSP GARTEHDQHQ LLRDNRAERG HKKNCSVRTA

401 SRQTSMHLGS LCTGDIKRRR KAAPLPGPTT AGFVGENAQP ILENNIGNRM

451 LQNMGWTPGS GLGRDGKGIS EPIQAMQRPK GLGLGFPLPK STSATTTPNA

501 GKSA
```

HLA Peptide Motif Search Results

| User Parameters and Scoring Information | |
|---|---|
| method selected to limit number of results | explicit number |
| number of results requested | 30 |
| HLA molecule type selected | B_3501 |
| length selected for subsequences to be scored | 9 |
| echoing mode selected for input sequence | Y |
| echoing format | Numbered lines |
| length of user's input peptide sequence | 504 |
| number of subsequence scores calculated | 496 |
| number of top-scoring subsequences reported back in scoring output table | 30 |

TABLE 15A

HLA Peptide Scoring Results - 84P2A9 - B35 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 1. | 478 | (SEQ ID NO: 389) | RPKGLGLGF | 120.000 |
| 2. | 56 | (SEQ ID NO: 390) | HPWETGHCL | 40.000 |
| 3. | 116 | (SEQ ID NO: 391) | RPLWHESDF | 40.000 |
| 4. | 425 | (SEQ ID NO: 392) | LPGPTTAGF | 20.000 |
| 5. | 334 | (SEQ ID NO: 393) | KSGGTPTSM | 20.000 |
| 6. | 400 | (SEQ ID NO: 394) | ASRQTSMHL | 15.000 |
| 7. | 29 | (SEQ ID NO: 395) | HSRSISCPL | 15.000 |
| 8. | 196 | (SEQ ID NO: 396) | GPKIQDEGV | 12.000 |
| 9. | 285 | (SEQ ID NO: 397) | DPTELDKNV | 8.000 |
| 10. | 239 | (SEQ ID NO: 398) | LSSTDAGLF | 7.500 |
| 11. | 139 | (SEQ ID NO: 399) | KVKRMAVDL | 6.000 |
| 12. | 233 | (SEQ ID NO: 400) | EQKVSDELM | 6.000 |
| 13. | 488 | (SEQ ID NO: 401) | LPKSTSATT | 6.000 |
| 14. | 198 | (SEQ ID NO: 402) | KIQDEGVVL | 6.000 |
| 15. | 182 | (SEQ ID NO: 403) | KNKVKKRKL | 6.000 |
| 16. | 309 | (SEQ ID NO: 404) | MSHPSRRGF | 5.000 |
| 17. | 360 | (SEQ ID NO: 405) | DSHHHDHWF | 5.000 |
| 18. | 50 | (SEQ ID NO: 406) | RSYNVHHPW | 5.000 |
| 19. | 103 | (SEQ ID NO: 407) | RPSSNLNNN | 4.000 |
| 20. | 468 | (SEQ ID NO: 408) | GISEPIQAM | 4.000 |
| 21. | 347 | (SEQ ID NO: 409) | GPVGNKRMV | 4.000 |

TABLE 15A-continued

HLA Peptide Scoring Results - 84P2A9 - B35 9-mers
Each peptide is a portion of SEQ ID NO: 2; each
start position is specified, the length of peptide
is 9 amino acids, and the end position for each
peptide is the start position plus eight

| Rank | Start Position | SEQ ID NO: | Subsequence Residue Listing | Score (Estimate of Half Time of Disassociation of a Molecule Containing This Subsequence) |
|---|---|---|---|---|
| 22. | 398 | (SEQ ID NO: 410) | RTASRQTSM | 4.000 |
| 23. | 295 | (SEQ ID NO: 411) | DPVFESILT | 3.000 |
| 24. | 476 | (SEQ ID NO: 412) | MQRPKGLGL | 3.000 |
| 25. | 74 | (SEQ ID NO: 413) | EPSKDYREN | 3.000 |
| 26. | 474 | (SEQ ID NO: 414) | QAMQRPKGL | 3.000 |
| 27. | 143 | (SEQ ID NO: 415) | MAVDLPQDI | 2.400 |
| 28. | 184 | (SEQ ID NO: 416) | KVKKRKLKI | 2.400 |
| 29. | 293 | (SEQ ID NO: 417) | VPDPVFESI | 2.400 |
| 30. | 90 | (SEQ ID NO: 418) | HSDSDDQML | 2.250 |

TABLE 15B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
101 KRRPSSNLNN NVRGKRPLWH ESDFAVDNVG NRTLRRRRKV KRMAVDLPQD
151 ISNKRTMTQP PEGCRDQDMD SDRAYQYQEF TKNKVKKRKL KIIRQGPKIQ
201 DEGVVLESEE TNQTNKDKME CEEQKVSDEL MSESDSSSLS STDAGLFTND
251 EGRQGDDEQS DWFYEKESGG ACGITGVVPW WEKEDPTELD KNVPDPVFES
301 ILTGSFPLMS HPSRRGFQAR LSRLHGMSSK NIKKSGGTPT SMVPIPGPVG
351 NKRMVHFSPD SHHHDHWFSP GARTEHDQHQ LLRDNRAERG HKKNCSVRTA
401 SRQTSMHLGS LCTGDIKRRR KAAPLPGPTT AGFVGENAQP ILENNIGNRM
451 LQNMGWTPGS GLGRDKGIS EPIQAMQRPK GLGLGFPLPK STSATTTPNA
501 GKSA
```

HLA Peptide Motif Search Results

| User Parameters and Scoring Information | |
|---|---|
| method selected to limit number of results | explicit number |
| number of results requested | 30 |
| HLA molecule type selected | B_3501 |
| length selected for subsequences to be scored | 10 |
| echoing mode selected for input sequence | Y |
| echoing format | Numbered lines |
| length of user's input peptide sequence | 504 |
| number of subsequence scores calculated | 495 |
| number of top-scoring subsequences reported back in scoring output table | 30 |

TABLE 16A

HLA Peptide Scoring Results - 84P2A9 - B35 10-mers
Each peptide is a portion of SEQ ID NO: 2; each start position is specified, the length of peptide is 10 amino acids, and the end position for each peptide is the start position plus nine

| Rank | Start Position | SEQ ID NO: | Subsequence Residue Listing | Score (Estimate of Half Time of Disassociation of a Molecule Containing This Subsequence) |
|---|---|---|---|---|
| 1. | 345 | (SEQ ID NO: 419) | IPGPVGNKRM | 40.000 |
| 2. | 70 | (SEQ ID NO: 420) | SSLEEPSKDY | 20.000 |
| 3. | 196 | (SEQ ID NO: 421) | GPKIQDEGVV | 18.000 |
| 4. | 318 | (SEQ ID NO: 422) | QARLSRLHGM | 18.000 |
| 5. | 14 | (SEQ ID NO: 423) | ESSEQARGGF | 10.000 |
| 6. | 99 | (SEQ ID NO: 424) | VAKRRPSSNL | 9.000 |
| 7. | 103 | (SEQ ID NO: 425) | RPSSNLNNNV | 8.000 |
| 8. | 116 | (SEQ ID NO: 426) | RPLWHESDFA | 6.000 |
| 9. | 488 | (SEQ ID NO: 427) | LPKSTSATTT | 6.000 |
| 10. | 293 | (SEQ ID NO: 428) | VPDPVFESIL | 6.000 |
| 11. | 299 | (SEQ ID NO: 429) | ESILTGSFPL | 5.000 |
| 12. | 237 | (SEQ ID NO: 430) | SSLSSTDAGL | 5.000 |
| 13. | 467 | (SEQ ID NO: 431) | KGISEPIQAM | 4.000 |
| 14. | 56 | (SEQ ID NO: 432) | HPWETGHCLS | 4.000 |
| 15. | 147 | (SEQ ID NO: 433) | LPQDISNKRT | 4.000 |
| 16. | 425 | (SEQ ID NO: 434) | LPGPTTAGFV | 4.000 |
| 17. | 358 | (SEQ ID NO: 435) | SPDSHHHDHW | 3.000 |
| 18. | 230 | (SEQ ID NO: 436) | LMSESDSSSL | 3.000 |
| 19. | 253 | (SEQ ID NO: 437) | RQGDDEQSDW | 3.000 |
| 20. | 399 | (SEQ ID NO: 438) | TASRQTSMHL | 3.000 |
| 21. | 184 | (SEQ ID NO: 439) | KVKKRKLKII | 2.400 |
| 22. | 445 | (SEQ ID NO: 440) | NIGNRMLQNM | 2.000 |
| 23. | 402 | (SEQ ID NO: 441) | RQTSMHLGSL | 2.000 |
| 24. | 300 | (SEQ ID NO: 442) | SILTGSFPLM | 2.000 |
| 25. | 334 | (SEQ ID NO: 443) | KSGGTPTSMV | 2.000 |
| 26. | 433 | (SEQ ID NO: 444) | FVGENAQPIL | 2.000 |
| 27. | 210 | (SEQ ID NO: 445) | ETNQTNKDKM | 2.000 |
| 28. | 63 | (SEQ ID NO: 446) | CLSEGSDSSL | 2.000 |
| 29. | 486 | (SEQ ID NO: 447) | FPLPKSTSAT | 2.000 |
| 30. | 315 | (SEQ ID NO: 448) | RGFQARLSRL | 2.000 |

TABLE 16B

Echoed User Peptide Sequence (length = 504 residues) (SEQ ID NO: 2)

```
  1 MEELVHDLVS ALEESSEQAR GGFAETGDHS RSISCPLKRQ ARKRRGRKRR
 51 SYNVHHPWET GHCLSEGSDS SLEEPSKDYR ENHNNNKKDH SDSDDQMLVA
```

TABLE 16B-continued

Echoed User Peptide Sequence (length = 504 residues) (SEQ ID NO: 2)

```
101 KRRPSSNLNN NVRGKRPLWH ESDFAVDNVG NRTLRRRRKV KRMAVDLPQD

151 ISNKRTMTQP PEGCRDQDMD SDRAYQYQEF TKNKVKKRKL KIIRQGPKIQ

201 DEGVVLESEE TNQTNKDKME CEEQKVSDEL MSESDSSSLS STDAGLFTND

251 EGRQGDDEQS DWFYEKESGG ACGITGVVPW WEKEDPTELD KNVPDPVFES

301 ILTGSFPLMS HPSRRGFQAR LSRLHGMSSK NIKKSGGTPT SMVPIPGPVG

351 NKRMVHFSPD SHHHDHWFSP GARTEHDQHQ LLRDNRAERG HKKNCSVRTA

401 SRQTSMHLGS LCTGDIKRRR KAAPLPGPTT AGFVGENAQP ILENNIGNRM

451 LQNMGWTPGS GLGRDGKGIS EPIQAMQRPK GLGLGFPLPK STSATTTPNA

501 GKSA
```

The invention claimed is:

1. An isolated antibody or fragment thereof that immunospecifically binds to an epitope on a 84P2A9 protein comprising an amino acid sequence shown in SEQ ID NO:2.

2. The isolated antibody or fragment thereof of claim 1, wherein the 84P2A9 protein is encoded by a polynucleotide comprising the sequence of SEQ ID NO:1.

3. The isolated antibody or fragment thereof of claim 1, which is monoclonal.

4. A hybridoma that produces the antibody of claim 3.

5. The isolated antibody or fragment thereof of claim 3, wherein the monoclonal antibody is a recombinant protein.

6. The isolated antibody or fragment thereof of claim 5, which is a single chain monoclonal antibody.

7. The isolated antibody or fragment thereof of claim 1, wherein the fragment is a Fab, F(ab')2, Fv or Sfv fragment.

8. The isolated antibody or fragment thereof of claim 1, which is a human antibody.

9. The isolated antibody or fragment thereof of claim 1, which is labeled with a cytotoxic agent.

10. The isolated antibody or fragment thereof of claim 9, wherein the cytotoxic agent is selected from the group consisting of radioactive isotopes, chemotherapeutic agents and toxins.

11. The isolated antibody or fragment thereof of claim 10, wherein the radioactive isotope is selected from the group consisting of $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

12. The isolated antibody or fragment thereof of claim 10, wherein the chemotherapeutic agent is selected from the group consisting of taxol, actinomycin, mitomycin, etoposide, tenoposide, vincristine, vinblastine, colchicine, gelonin, and calicheamicin.

13. The isolated antibody or fragment thereof of claim 10, wherein the toxin is selected from the group consisting of diphtheria toxin, neomycin, phenomycin, Pseudomonas exotoxin (PE) A, PE40, abrin, abrin A chain, mitogellin, modeccin A chain, and alpha-sarcin.

14. A vector comprising a polynucleotide encoding a single chain monoclonal antibody of claim 6.

* * * * *

SEQUENCE LISTING

<160> NUMBER OF SEQ ID NOS: 484

<210> SEQ ID NO 1
<211> LENGTH: 2345
<212> TYPE: DNA
<213> ORGANISM: Homo Sapiens
<220> FEATURE:
<221> NAME/KEY: CDS
<222> LOCATION: (163)...(1674)

<400> SEQUENCE: 1

```
attcggcacg aggtggaagt cgccggtgct gttgtagttg gagtctgttc acgggcctga      60
gcttcgaggc caggctcctg ggtgtcgtta atgttcgggg ccgccggggcg ccaaccgatc     120 ggagctccag cagccgggaa cagctggcat ttcagtagaa cc atg gag gag ctg         174
                                                Met Glu Glu Leu
                                                  1 gtt cat gac ctt gtc tca gca ttg gaa gag agc tca gag caa gct cga        222
Val His Asp Leu Val Ser Ala Leu Glu Glu Ser Ser Glu Gln Ala Arg
  5                  10                  15                  20 ggt gga ttt gct gaa aca gga gac cat tct cga agt ata tct tgc cct        270
Gly Gly Phe Ala Glu Thr Gly Asp His Ser Arg Ser Ile Ser Cys Pro
                 25                  30                  35 ctg aaa cgc cag gca agg aaa agg aga ggg aga aaa cgg agg tcg tat        318
Leu Lys Arg Gln Ala Arg Lys Arg Arg Gly Arg Lys Arg Arg Ser Tyr
             40                  45                  50 aat gtg cat cac ccg tgg gag act ggt cac tgc tta agt gaa ggc tct        366
Asn Val His His Pro Trp Glu Thr Gly His Cys Leu Ser Glu Gly Ser
         55                  60                  65 gat tct agt tta gaa gaa cca agc aag gac tat aga gag aat cac aat        414
Asp Ser Ser Leu Glu Glu Pro Ser Lys Asp Tyr Arg Glu Asn His Asn
     70                  75                  80 aat aat aaa aaa gat cac agt gac tct gat gac caa atg tta gta gca        462
Asn Asn Lys Lys Asp His Ser Asp Ser Asp Asp Gln Met Leu Val Ala
 85                  90                  95                 100 aag cgc agg ccg tca tca aac tta aat aat aat gtt cga ggg aaa aga        510
Lys Arg Arg Pro Ser Ser Asn Leu Asn Asn Asn Val Arg Gly Lys Arg
                105                 110                 115 cct cta tgg cat gag tct gat ttt gct gtg gac aat gtt ggg aat aga        558
Pro Leu Trp His Glu Ser Asp Phe Ala Val Asp Asn Val Gly Asn Arg
            120                 125                 130
```

| | | |
|---|---|---|
| act ctg cgc agg agg aga aag gta aaa cgc atg gca gta gat ctc cca<br>Thr Leu Arg Arg Arg Arg Lys Val Lys Arg Met Ala Val Asp Leu Pro<br>           135                  140                  145 | | 606 |
| cag gac atc tct aac aaa cgg aca atg acc cag cca cct gag ggt tgt<br>Gln Asp Ile Ser Asn Lys Arg Thr Met Thr Gln Pro Pro Glu Gly Cys<br>150                      155                  160 | | 654 |
| aga gat cag gac atg gac agt gat aga gcc tac cag tat caa gaa ttt<br>Arg Asp Gln Asp Met Asp Ser Asp Arg Ala Tyr Gln Tyr Gln Glu Phe<br>165                      170                  175                  180 | | 702 |
| acc aag aac aaa gtc aaa aaa aga aag ttg aaa ata atc aga caa gga<br>Thr Lys Asn Lys Val Lys Lys Arg Lys Leu Lys Ile Ile Arg Gln Gly<br>                  185                  190                  195 | | 750 |
| cca aaa atc caa gat gaa gga gta gtt tta gaa agt gag gaa acg aac<br>Pro Lys Ile Gln Asp Glu Gly Val Val Leu Glu Ser Glu Glu Thr Asn<br>           200                  205                  210 | | 798 |
| cag acc aat aag gac aaa atg gaa tgt gaa gag caa aaa gtc tca gat<br>Gln Thr Asn Lys Asp Lys Met Glu Cys Glu Glu Gln Lys Val Ser Asp<br>                  215                  220                  225 | | 846 |
| gag ctc atg agt gaa agt gat tcc agc agt ctc agc agc act gat gct<br>Glu Leu Met Ser Glu Ser Asp Ser Ser Ser Leu Ser Ser Thr Asp Ala<br>230                      235                  240 | | 894 |
| gga ttg ttt acc aat gat gag gga aga caa ggt gat gat gaa cag agt<br>Gly Leu Phe Thr Asn Asp Glu Gly Arg Gln Gly Asp Asp Glu Gln Ser<br>245                      250                  255                  260 | | 942 |
| gac tgg ttc tac gaa aag gaa tca ggt gga gca tgt ggt atc act gga<br>Asp Trp Phe Tyr Glu Lys Glu Ser Gly Gly Ala Cys Gly Ile Thr Gly<br>                  265                  270                  275 | | 990 |
| gtt gtg ccc tgg tgg gaa aag gaa gat cct act gag cta gac aaa aat<br>Val Val Pro Trp Trp Glu Lys Glu Asp Pro Thr Glu Leu Asp Lys Asn<br>                    280                  285                  290 | | 1038 |
| gta cca gat cct gtc ttt gaa agt atc tta act ggt tct ttt ccc ctt<br>Val Pro Asp Pro Val Phe Glu Ser Ile Leu Thr Gly Ser Phe Pro Leu<br>                  295                  300                  305 | | 1086 |
| atg tca cac cca agc aga aga ggt ttc caa gct aga ctc agt cgc ctt<br>Met Ser His Pro Ser Arg Arg Gly Phe Gln Ala Arg Leu Ser Arg Leu<br>310                      315                  320 | | 1134 |
| cat gga atg tct tca aag aat att aaa aaa tct ggg act cca act<br>His Gly Met Ser Ser Lys Asn Ile Lys Lys Ser Gly Gly Thr Pro Thr<br>325                      330                  335                  340 | | 1182 |
| tca atg gta ccc att cct ggc cca gtg ggt aac aag aga atg gtt cat<br>Ser Met Val Pro Ile Pro Gly Pro Val Gly Asn Lys Arg Met Val His<br>                  345                  350                  355 | | 1230 |
| ttt tcc ccg gat tct cat cac cat gac cat tgg ttt agc cct ggg gct<br>Phe Ser Pro Asp Ser His His His Asp His Trp Phe Ser Pro Gly Ala<br>                  360                  365                  370 | | 1278 |
| agg aca gag cat gac cag cat cag ctt ctg aga gat aat cga gct gaa<br>Arg Thr Glu His Asp Gln His Gln Leu Leu Arg Asp Asn Arg Ala Glu<br>375                      380                  385 | | 1326 |
| aga gga cac aag aaa aat tgt tct gtg aga aca gcc agc agg caa aca<br>Arg Gly His Lys Lys Asn Cys Ser Val Arg Thr Ala Ser Arg Gln Thr<br>           390                  395                  400 | | 1374 |
| agc atg cat tta gga tcc tta tgc acg gga gat atc aaa cgg aga aga<br>Ser Met His Leu Gly Ser Leu Cys Thr Gly Asp Ile Lys Arg Arg Arg<br>405                      410                  415                  420 | | 1422 |
| aaa gct gca cct ttg cct gga cct act act gca gga ttt gta ggt gaa<br>Lys Ala Ala Pro Leu Pro Gly Pro Thr Thr Ala Gly Phe Val Gly Glu<br>                  425                  430                  435 | | 1470 |
| aat gcc cag cca atc cta gaa aat aat att gga aac cga atg ctt cag<br>Asn Ala Gln Pro Ile Leu Glu Asn Asn Ile Gly Asn Arg Met Leu Gln<br>           440                  445                  450 | | 1518 |

```
aat atg ggc tgg acg cct ggg tca ggc ctt gga cga gat ggc aag ggg     1566
Asn Met Gly Trp Thr Pro Gly Ser Gly Leu Gly Arg Asp Gly Lys Gly
        455                 460                 465 atc tct gag cca att caa gcc atg cag agg cca aag gga tta gga ctt     1614
Ile Ser Glu Pro Ile Gln Ala Met Gln Arg Pro Lys Gly Leu Gly Leu
    470                 475                 480 gga ttt cct cta cca aaa agt act tcc gca act act acc ccc aat gca     1662
Gly Phe Pro Leu Pro Lys Ser Thr Ser Ala Thr Thr Thr Pro Asn Ala
485                 490                 495                 500 gga aaa tcc gcc taagaaaagc aagaagaaa tgttttacag actttattca          1714
Gly Lys Ser Ala ctatgtccca ttgttctaaa atgataacat gacttctgtt tttgaagcaa aaatctacat    1774
tgcctcaaac acatcactct agcttcctta ctgcatacag tcctgccata gtgagagaaa   1834
tgggatttca tcacaattca tggtgctaaa atgaaaacct ctgcacttta attttttttca  1894
gtaatttcca gctatttcta ggtataaaga gcagctcgtt tctcttattt attttagtct   1954
catgtgtcaa tactttccga tgctttgctt aattcatgta tgtgtgcagt gctgcaatgc   2014
ccagacaaac gtgagcacac ccaccagttt ctaaaatgga atagacagga aaagattgtg  2074
ttttatatca tccctatcta ttgtaaccca aaagacctac catcgcatca gtgaagtccg   2134
aacacatctt tgtttgaaag gcttgtcaat ttcatattcc ttgaattggc ttcttggtga  2194
ggattttctg acagagtgat acccatcaat tttctatcct tagacaatgt agtgtgaagt  2254
tcacagttga caaacaacaa ttaatgtttc ccttggatgt tttgacaaaa ataaacctca  2314
tcgttgttat caccaaaaaa aaaaaaaaaa a                                   2345

<210> SEQ ID NO 2
<211> LENGTH: 504
<212> TYPE: PRT
<213> ORGANISM: Homo Sapiens

<400> SEQUENCE: 2

Met Glu Glu Leu Val His Asp Leu Val Ser Ala Leu Glu Glu Ser Ser
 1               5                  10                  15

Glu Gln Ala Arg Gly Gly Phe Ala Glu Thr Gly Asp His Ser Arg Ser
            20                  25                  30

Ile Ser Cys Pro Leu Lys Arg Gln Ala Arg Lys Arg Gly Arg Lys
        35                  40                  45

Arg Arg Ser Tyr Asn Val His His Pro Trp Glu Thr Gly His Cys Leu
    50                  55                  60

Ser Glu Gly Ser Asp Ser Ser Leu Glu Glu Pro Ser Lys Asp Tyr Arg
65                  70                  75                  80

Glu Asn His Asn Asn Lys Lys Asp His Ser Asp Ser Asp Asp Gln
                85                  90                  95

Met Leu Val Ala Lys Arg Arg Pro Ser Ser Asn Leu Asn Asn Val
            100                 105                 110

Arg Gly Lys Arg Pro Leu Trp His Glu Ser Asp Phe Ala Val Asp Asn
        115                 120                 125

Val Gly Asn Arg Thr Leu Arg Arg Arg Lys Val Lys Arg Met Ala
    130                 135                 140

Val Asp Leu Pro Gln Asp Ile Ser Asn Lys Arg Thr Met Thr Gln Pro
145                 150                 155                 160

Pro Glu Gly Cys Arg Asp Gln Asp Met Asp Ser Asp Arg Ala Tyr Gln
                165                 170                 175

Tyr Gln Glu Phe Thr Lys Asn Lys Val Lys Lys Arg Lys Leu Lys Ile
```

```
                       180             185                 190
Ile Arg Gln Gly Pro Lys Ile Gln Asp Glu Gly Val Val Leu Glu Ser
            195                 200                 205
Glu Glu Thr Asn Gln Thr Asn Lys Asp Lys Met Glu Cys Glu Glu Gln
    210                 215                 220
Lys Val Ser Asp Glu Leu Met Ser Glu Ser Asp Ser Ser Leu Ser
225                 230                 235                 240
Ser Thr Asp Ala Gly Leu Phe Thr Asn Asp Glu Gly Arg Gln Gly Asp
                245                 250                 255
Asp Glu Gln Ser Asp Trp Phe Tyr Glu Lys Glu Ser Gly Gly Ala Cys
            260                 265                 270
Gly Ile Thr Gly Val Val Pro Trp Trp Glu Lys Glu Asp Pro Thr Glu
            275                 280                 285
Leu Asp Lys Asn Val Pro Asp Pro Val Phe Glu Ser Ile Leu Thr Gly
    290                 295                 300
Ser Phe Pro Leu Met Ser His Pro Ser Arg Arg Gly Phe Gln Ala Arg
305                 310                 315                 320
Leu Ser Arg Leu His Gly Met Ser Ser Lys Asn Ile Lys Lys Ser Gly
                325                 330                 335
Gly Thr Pro Thr Ser Met Val Pro Ile Pro Gly Pro Val Gly Asn Lys
            340                 345                 350
Arg Met Val His Phe Ser Pro Asp Ser His His Asp His Trp Phe
            355                 360                 365
Ser Pro Gly Ala Arg Thr Glu His Asp Gln His Gln Leu Leu Arg Asp
    370                 375                 380
Asn Arg Ala Glu Arg Gly His Lys Lys Asn Cys Ser Val Arg Thr Ala
385                 390                 395                 400
Ser Arg Gln Thr Ser Met His Leu Gly Ser Leu Cys Thr Gly Asp Ile
                405                 410                 415
Lys Arg Arg Arg Lys Ala Ala Pro Leu Pro Gly Pro Thr Thr Ala Gly
            420                 425                 430
Phe Val Gly Glu Asn Ala Gln Pro Ile Leu Glu Asn Asn Ile Gly Asn
            435                 440                 445
Arg Met Leu Gln Asn Met Gly Trp Thr Pro Gly Ser Gly Leu Gly Arg
    450                 455                 460
Asp Gly Lys Gly Ile Ser Glu Pro Ile Gln Ala Met Gln Arg Pro Lys
465                 470                 475                 480
Gly Leu Gly Leu Gly Phe Pro Leu Pro Lys Ser Thr Ser Ala Thr Thr
                485                 490                 495
Thr Pro Asn Ala Gly Lys Ser Ala
            500

<210> SEQ ID NO 3
<211> LENGTH: 425
<212> TYPE: DNA
<213> ORGANISM: Homo Sapiens

<400> SEQUENCE: 3
gatcaagctt tttttttttt tttttttttt ttttggataa caacgatgag gtttattttt     60
gtcaaaacat ccaagggaaa cattaattgt tgtttgtcaa ctgtgaactt cacactacat    120
tgtctaagga tagaaaattg atgggtatca ctctgtcaga aaatcctcac caagaagcca    180
attcaaggaa tatgaaattg acaagccttt caaacaaaga tgtgttcgga cttcactgat    240
gcgatggtag gtcttttggg ttacaataga tagggatgat ataaaacaca atcttttcct    300
```

```
gtctattcca ttttagaaac tggtgggtgt gctcacgttt gtctgggcat tgcagcactg    360
cacacataca tgaattaagc aaagcatcgg aaagtattga cacatgagac taaataaat     420 aagag                                                                425
```

<210> SEQ ID NO 4
<211> LENGTH: 7
<212> TYPE: DNA
<213> ORGANISM: Homo Sapiens

<400> SEQUENCE: 4

```
aacatgg                                                              7
```

<210> SEQ ID NO 5
<211> LENGTH: 320
<212> TYPE: PRT
<213> ORGANISM: Homo Sapiens

<400> SEQUENCE: 5

```
Met Asp Glu Leu Val His Asp Leu Ala Ser Ala Leu Glu Gln Thr Ser
 1               5                  10                  15

Glu Gln Asn Lys Leu Gly Glu Leu Trp Glu Met Ala Leu Ser Pro
            20                  25                  30

Arg Gln Gln Arg Arg Gln Leu Arg Lys Arg Gly Arg Lys Arg Arg
        35                  40                  45

Ser Asp Phe Thr His Leu Ala Glu His Thr Cys Cys Tyr Ser Glu Ala
 50                  55                  60

Ser Glu Ser Ser Leu Asp Glu Ala Thr Lys Asp Cys Arg Glu Val Ala
 65                  70                  75                  80

Pro Val Thr Asn Phe Ser Asp Ser Asp Thr Met Val Ala Lys Arg
                85                  90                  95

His Pro Ala Leu Asn Ala Ile Val Lys Ser Lys Gln His Ser Trp His
            100                 105                 110

Glu Ser Asp Ser Phe Thr Glu Asn Ala Pro Cys Arg Pro Leu Arg Arg
            115                 120                 125

Arg Arg Lys Val Lys Arg Val Thr Ser Glu Val Ala Ala Ser Leu Gln
        130                 135                 140

Gln Lys Leu Lys Val Ser Asp Trp Ser Tyr Glu Arg Gly Cys Arg Phe
145                 150                 155                 160

Lys Ser Ala Lys Lys Gln Arg Leu Ser Arg Trp Lys Glu Asn Thr Pro
                165                 170                 175

Trp Thr Ser Ser Gly His Gly Leu Cys Glu Ser Ala Glu Asn Arg Thr
            180                 185                 190

Phe Leu Ser Lys Thr Gly Arg Lys Glu Arg Met Glu Cys Glu Thr Asp
        195                 200                 205

Glu Gln Lys Gln Gly Ser Asp Glu Asn Met Ser Glu Cys Glu Thr Ser
        210                 215                 220

Ser Val Cys Ser Ser Ser Asp Thr Gly Leu Phe Thr Asn Asp Glu Gly
225                 230                 235                 240

Arg Gln Gly Asp Asp Glu Gln Ser Asp Trp Phe Tyr Glu Gly Glu Cys
                245                 250                 255

Val Pro Gly Phe Thr Val Pro Asn Leu Leu Pro Lys Trp Ala Pro Asp
            260                 265                 270

His Cys Ser Glu Val Glu Arg Met Asp Ser Gly Leu Asp Lys Phe Ser
        275                 280                 285

Asp Ser Thr Phe Leu Leu Pro Ser Arg Pro Ala Gln Arg Gly Tyr His
        290                 295                 300
```

Thr Arg Leu Asn Arg Leu Pro Gly Ala Ala Ala Arg Cys Leu Arg Lys
305                 310                 315                 320

<210> SEQ ID NO 6
<211> LENGTH: 42
<212> TYPE: PRT
<213> ORGANISM: Homo Sapiens

<400> SEQUENCE: 6

Ser Asn Ile Gly Asn Lys Met Leu Gln Ala Met Gly Trp Arg Glu Gly
 1               5                  10                  15

Ser Gly Leu Gly Arg Lys Cys Gln Gly Ile Thr Ala Pro Ile Glu Ala
            20                  25                  30

Gln Val Arg Leu Lys Gly Ala Gly Leu Gly
        35                  40

<210> SEQ ID NO 7
<211> LENGTH: 44
<212> TYPE: DNA
<213> ORGANISM: Artificial Sequence
<220> FEATURE:
<223> OTHER INFORMATION: Primer

<400> SEQUENCE: 7
ttttgatcaa gctttttttt tttttttttt tttttttttt tttt            44

<210> SEQ ID NO 8
<211> LENGTH: 42
<212> TYPE: DNA
<213> ORGANISM: Artificial Sequence
<220> FEATURE:
<223> OTHER INFORMATION: Adaptor

<400> SEQUENCE: 8
ctaatacgac tcactatagg gctcgagcgg ccgcccgggc ag              42

<210> SEQ ID NO 9
<211> LENGTH: 12
<212> TYPE: DNA
<213> ORGANISM: Artificial Sequence
<220> FEATURE:
<223> OTHER INFORMATION: Adaptor

<400> SEQUENCE: 9
ggcccgtcct ag                                               12

<210> SEQ ID NO 10
<211> LENGTH: 40
<212> TYPE: DNA
<213> ORGANISM: Artificial Sequence
<220> FEATURE:
<223> OTHER INFORMATION: Adaptor

<400> SEQUENCE: 10
gtaatacgac tcactatagg gcagcgtggt cgcggccgag                 40

<210> SEQ ID NO 11
<211> LENGTH: 10
<212> TYPE: DNA
<213> ORGANISM: Artificial Sequence
<220> FEATURE:
<223> OTHER INFORMATION: Adaptor

<400> SEQUENCE: 11
cggctcctag                                                  10

-continued

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ctaatacgac tcactatagg gc                                              22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
tcgagcggcc gcccgggcag ga                                              22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
agcgtggtcg cggccgagga                                                 20

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
atatcgccgc gctcgtcgtc gacaa                                           25

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
agccacacgc agctcattgt agaagg                                          26

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
gacttcactg atgcgatggt aggt                                            24

<210> SEQ ID NO 18
<211> LENGTH: 24
<212> TYPE: DNA
<213> ORGANISM: Artificial Sequence
<220> FEATURE:
<223> OTHER INFORMATION: Primer

```
<400> SEQUENCE: 18
gtcaatactt tccgatgctt tgct                                          24

<210> SEQ ID NO 19
<211> LENGTH: 9
<212> TYPE: PRT
<213> ORGANISM: Homo Sapiens

<400> SEQUENCE: 19

Ser Ile Leu Thr Gly Ser Phe Pro Leu
1               5

<210> SEQ ID NO 20
<211> LENGTH: 9
<212> TYPE: PRT
<213> ORGANISM: Homo Sapiens

<400> SEQUENCE: 20

Arg Met Leu Gln Asn Met Gly Trp Thr
1               5

<210> SEQ ID NO 21
<211> LENGTH: 9
<212> TYPE: PRT
<213> ORGANISM: Homo Sapiens

<400> SEQUENCE: 21

Leu Val His Asp Leu Val Ser Ala Leu
1               5

<210> SEQ ID NO 22
<211> LENGTH: 9
<212> TYPE: PRT
<213> ORGANISM: Homo Sapiens

<400> SEQUENCE: 22

Ser Leu Ser Ser Thr Asp Ala Gly Leu
1               5

<210> SEQ ID NO 23
<211> LENGTH: 9
<212> TYPE: PRT
<213> ORGANISM: Homo Sapiens

<400> SEQUENCE: 23

Lys Ile Gln Asp Glu Gly Val Val Leu
1               5

<210> SEQ ID NO 24
<211> LENGTH: 9
<212> TYPE: PRT
<213> ORGANISM: Homo Sapiens

<400> SEQUENCE: 24

Phe Val Gly Glu Asn Ala Gln Pro Ile
1               5

<210> SEQ ID NO 25
<211> LENGTH: 9
<212> TYPE: PRT
<213> ORGANISM: Homo Sapiens

<400> SEQUENCE: 25

Ile Leu Thr Gly Ser Phe Pro Leu Met
```

<210> SEQ ID NO 26
<211> LENGTH: 9
<212> TYPE: PRT
<213> ORGANISM: Homo Sapiens

<400> SEQUENCE: 26

Lys Met Glu Cys Glu Glu Gln Lys Val
1               5

<210> SEQ ID NO 27
<211> LENGTH: 9
<212> TYPE: PRT
<213> ORGANISM: Homo Sapiens

<400> SEQUENCE: 27

Lys Gly Leu Gly Leu Gly Phe Pro Leu
1               5

<210> SEQ ID NO 28
<211> LENGTH: 9
<212> TYPE: PRT
<213> ORGANISM: Homo Sapiens

<400> SEQUENCE: 28

Gly Leu Gly Arg Asp Gly Lys Gly Ile
1               5

<210> SEQ ID NO 29
<211> LENGTH: 9
<212> TYPE: PRT
<213> ORGANISM: Homo sapiens

<400> SEQUENCE: 29

Ser Leu Glu Glu Pro Ser Lys Asp Tyr
1               5

<210> SEQ ID NO 30
<211> LENGTH: 9
<212> TYPE: PRT
<213> ORGANISM: Homo sapiens

<400> SEQUENCE: 30

Ile Ser Glu Pro Ile Gln Ala Met Gln
1               5

<210> SEQ ID NO 31
<211> LENGTH: 9
<212> TYPE: PRT
<213> ORGANISM: Homo sapiens

<400> SEQUENCE: 31

Lys Glu Asp Pro Thr Glu Leu Asp Lys
1               5

<210> SEQ ID NO 32
<211> LENGTH: 9
<212> TYPE: PRT
<213> ORGANISM: Homo sapiens

<400> SEQUENCE: 32

Ser Ser Glu Gln Ala Arg Gly Gly Phe
1               5

```
<210> SEQ ID NO 33
<211> LENGTH: 9
<212> TYPE: PRT
<213> ORGANISM: Homo sapiens

<400> SEQUENCE: 33

Phe Ala Glu Thr Gly Asp His Ser Arg
1               5

<210> SEQ ID NO 34
<211> LENGTH: 9
<212> TYPE: PRT
<213> ORGANISM: Homo sapiens

<400> SEQUENCE: 34

Ile Leu Glu Asn Asn Ile Gly Asn Arg
1               5

<210> SEQ ID NO 35
<211> LENGTH: 9
<212> TYPE: PRT
<213> ORGANISM: Homo sapiens

<400> SEQUENCE: 35

Ser Thr Asp Ala Gly Leu Phe Thr Asn
1               5

<210> SEQ ID NO 36
<211> LENGTH: 9
<212> TYPE: PRT
<213> ORGANISM: Homo sapiens

<400> SEQUENCE: 36

Leu Glu Glu Pro Ser Lys Asp Tyr Arg
1               5

<210> SEQ ID NO 37
<211> LENGTH: 9
<212> TYPE: PRT
<213> ORGANISM: Homo sapiens

<400> SEQUENCE: 37

Glu Ser Asp Ser Ser Ser Leu Ser Ser
1               5

<210> SEQ ID NO 38
<211> LENGTH: 9
<212> TYPE: PRT
<213> ORGANISM: Homo sapiens

<400> SEQUENCE: 38

Asp Ser Asp Asp Gln Met Leu Val Ala
1               5

<210> SEQ ID NO 39
<211> LENGTH: 9
<212> TYPE: PRT
<213> ORGANISM: Homo sapiens

<400> SEQUENCE: 39

Met Thr Gln Pro Pro Glu Gly Cys Arg
1               5

<210> SEQ ID NO 40
<211> LENGTH: 9
<212> TYPE: PRT
```

<213> ORGANISM: Homo sapiens

<400> SEQUENCE: 40

Thr Gly Asp Ile Lys Arg Arg Arg Lys
1               5

<210> SEQ ID NO 41
<211> LENGTH: 9
<212> TYPE: PRT
<213> ORGANISM: Homo sapiens

<400> SEQUENCE: 41

Asp Asp Glu Gln Ser Asp Trp Phe Tyr
1               5

<210> SEQ ID NO 42
<211> LENGTH: 9
<212> TYPE: PRT
<213> ORGANISM: Homo sapiens

<400> SEQUENCE: 42

Arg Thr Glu His Asp Gln His Gln Leu
1               5

<210> SEQ ID NO 43
<211> LENGTH: 9
<212> TYPE: PRT
<213> ORGANISM: Homo sapiens

<400> SEQUENCE: 43

Met Ser His Pro Ser Arg Arg Gly Phe
1               5

<210> SEQ ID NO 44
<211> LENGTH: 9
<212> TYPE: PRT
<213> ORGANISM: Homo sapiens

<400> SEQUENCE: 44

Glu Ser Glu Glu Thr Asn Gln Thr Asn
1               5

<210> SEQ ID NO 45
<211> LENGTH: 9
<212> TYPE: PRT
<213> ORGANISM: Homo sapiens

<400> SEQUENCE: 45

Met Ser Glu Ser Asp Ser Ser Ser Leu
1               5

<210> SEQ ID NO 46
<211> LENGTH: 9
<212> TYPE: PRT
<213> ORGANISM: Homo sapiens

<400> SEQUENCE: 46

Leu Ser Glu Gly Ser Asp Ser Ser Leu
1               5

<210> SEQ ID NO 47
<211> LENGTH: 9
<212> TYPE: PRT
<213> ORGANISM: Homo sapiens

<400> SEQUENCE: 47

```
Trp Thr Pro Gly Ser Gly Leu Gly Arg
1               5

<210> SEQ ID NO 48
<211> LENGTH: 9
<212> TYPE: PRT
<213> ORGANISM: Homo sapiens

<400> SEQUENCE: 48

Glu His Asp Gln His Gln Leu Leu Arg
1               5

<210> SEQ ID NO 49
<211> LENGTH: 9
<212> TYPE: PRT
<213> ORGANISM: Homo sapiens

<400> SEQUENCE: 49

Val Pro Asp Pro Val Phe Glu Ser Ile
1               5

<210> SEQ ID NO 50
<211> LENGTH: 9
<212> TYPE: PRT
<213> ORGANISM: Homo sapiens

<400> SEQUENCE: 50

Ser Asp Asp Gln Met Leu Val Ala Lys
1               5

<210> SEQ ID NO 51
<211> LENGTH: 9
<212> TYPE: PRT
<213> ORGANISM: Homo sapiens

<400> SEQUENCE: 51

Ala Thr Thr Thr Pro Asn Ala Gly Lys
1               5

<210> SEQ ID NO 52
<211> LENGTH: 9
<212> TYPE: PRT
<213> ORGANISM: Homo sapiens

<400> SEQUENCE: 52

Ser Glu Glu Thr Asn Gln Thr Asn Lys
1               5

<210> SEQ ID NO 53
<211> LENGTH: 9
<212> TYPE: PRT
<213> ORGANISM: Homo sapiens

<400> SEQUENCE: 53

Val Leu Glu Ser Glu Glu Thr Asn Gln
1               5

<210> SEQ ID NO 54
<211> LENGTH: 9
<212> TYPE: PRT
<213> ORGANISM: Homo sapiens

<400> SEQUENCE: 54

Tyr Arg Glu Asn His Asn Asn Asn Lys
1               5
```

```
<210> SEQ ID NO 55
<211> LENGTH: 9
<212> TYPE: PRT
<213> ORGANISM: Homo sapiens

<400> SEQUENCE: 55

Ala Leu Glu Glu Ser Ser Glu Gln Ala
 1               5

<210> SEQ ID NO 56
<211> LENGTH: 9
<212> TYPE: PRT
<213> ORGANISM: Homo sapiens

<400> SEQUENCE: 56

Val Ser Asp Glu Leu Met Ser Glu Ser
 1               5

<210> SEQ ID NO 57
<211> LENGTH: 9
<212> TYPE: PRT
<213> ORGANISM: Homo sapiens

<400> SEQUENCE: 57

Arg Ser Ile Ser Cys Pro Leu Lys Arg
 1               5

<210> SEQ ID NO 58
<211> LENGTH: 9
<212> TYPE: PRT
<213> ORGANISM: Homo sapiens

<400> SEQUENCE: 58

His Ser Asp Ser Asp Asp Gln Met Leu
 1               5

<210> SEQ ID NO 59
<211> LENGTH: 10
<212> TYPE: PRT
<213> ORGANISM: Homo sapiens

<400> SEQUENCE: 59

Ile Ser Glu Pro Ile Gln Ala Met Gln Arg
 1               5                  10

<210> SEQ ID NO 60
<211> LENGTH: 10
<212> TYPE: PRT
<213> ORGANISM: Homo sapiens

<400> SEQUENCE: 60

Asp Ser Asp Asp Gln Met Leu Val Ala Lys
 1               5                  10

<210> SEQ ID NO 61
<211> LENGTH: 10
<212> TYPE: PRT
<213> ORGANISM: Homo sapiens

<400> SEQUENCE: 61

Glu Ser Glu Glu Thr Asn Gln Thr Asn Lys
 1               5                  10

<210> SEQ ID NO 62
```

```
<211> LENGTH: 10
<212> TYPE: PRT
<213> ORGANISM: Homo sapiens

<400> SEQUENCE: 62

Asp Met Asp Ser Asp Arg Ala Tyr Gln Tyr
1               5                   10

<210> SEQ ID NO 63
<211> LENGTH: 10
<212> TYPE: PRT
<213> ORGANISM: Homo sapiens

<400> SEQUENCE: 63

Ala Leu Glu Glu Ser Ser Glu Gln Ala Arg
1               5                   10

<210> SEQ ID NO 64
<211> LENGTH: 10
<212> TYPE: PRT
<213> ORGANISM: Homo sapiens

<400> SEQUENCE: 64

Ser Leu Glu Glu Pro Ser Lys Asp Tyr Arg
1               5                   10

<210> SEQ ID NO 65
<211> LENGTH: 10
<212> TYPE: PRT
<213> ORGANISM: Homo sapiens

<400> SEQUENCE: 65

Glu Lys Glu Asp Pro Thr Glu Leu Asp Lys
1               5                   10

<210> SEQ ID NO 66
<211> LENGTH: 10
<212> TYPE: PRT
<213> ORGANISM: Homo sapiens

<400> SEQUENCE: 66

Asp Gln Asp Met Asp Ser Asp Arg Ala Tyr
1               5                   10

<210> SEQ ID NO 67
<211> LENGTH: 10
<212> TYPE: PRT
<213> ORGANISM: Homo sapiens

<400> SEQUENCE: 67

His Ser Asp Ser Asp Asp Gln Met Leu Val
1               5                   10

<210> SEQ ID NO 68
<211> LENGTH: 10
<212> TYPE: PRT
<213> ORGANISM: Homo sapiens

<400> SEQUENCE: 68

Tyr Gln Glu Phe Thr Lys Asn Lys Val Lys
1               5                   10

<210> SEQ ID NO 69
<211> LENGTH: 10
<212> TYPE: PRT
<213> ORGANISM: Homo sapiens
```

<400> SEQUENCE: 69

Ala Val Asp Leu Pro Gln Asp Ile Ser Asn
1               5                   10

<210> SEQ ID NO 70
<211> LENGTH: 10
<212> TYPE: PRT
<213> ORGANISM: Homo sapiens

<400> SEQUENCE: 70

Arg Thr Glu His Asp Gln His Gln Leu Leu
1               5                   10

<210> SEQ ID NO 71
<211> LENGTH: 10
<212> TYPE: PRT
<213> ORGANISM: Homo sapiens

<400> SEQUENCE: 71

Ile Ser Cys Pro Leu Lys Arg Gln Ala Arg
1               5                   10

<210> SEQ ID NO 72
<211> LENGTH: 10
<212> TYPE: PRT
<213> ORGANISM: Homo sapiens

<400> SEQUENCE: 72

Met Ser Glu Ser Asp Ser Ser Ser Leu Ser
1               5                   10

<210> SEQ ID NO 73
<211> LENGTH: 10
<212> TYPE: PRT
<213> ORGANISM: Homo sapiens

<400> SEQUENCE: 73

Ser Ser Glu Gln Ala Arg Gly Gly Phe Ala
1               5                   10

<210> SEQ ID NO 74
<211> LENGTH: 10
<212> TYPE: PRT
<213> ORGANISM: Homo sapiens

<400> SEQUENCE: 74

Gln Gly Asp Asp Glu Gln Ser Asp Trp Phe
1               5                   10

<210> SEQ ID NO 75
<211> LENGTH: 10
<212> TYPE: PRT
<213> ORGANISM: Homo sapiens

<400> SEQUENCE: 75

Gly Asp Asp Glu Gln Ser Asp Trp Phe Tyr
1               5                   10

<210> SEQ ID NO 76
<211> LENGTH: 10
<212> TYPE: PRT
<213> ORGANISM: Homo sapiens

<400> SEQUENCE: 76

```
Val Pro Asp Pro Val Phe Glu Ser Ile Leu
1               5                   10

<210> SEQ ID NO 77
<211> LENGTH: 10
<212> TYPE: PRT
<213> ORGANISM: Homo sapiens

<400> SEQUENCE: 77

Arg Ala Tyr Gln Tyr Gln Glu Phe Thr Lys
1               5                   10

<210> SEQ ID NO 78
<211> LENGTH: 10
<212> TYPE: PRT
<213> ORGANISM: Homo sapiens

<400> SEQUENCE: 78

Gly Leu Gly Leu Gly Phe Pro Leu Pro Lys
1               5                   10

<210> SEQ ID NO 79
<211> LENGTH: 10
<212> TYPE: PRT
<213> ORGANISM: Homo sapiens

<400> SEQUENCE: 79

Val Leu Glu Ser Glu Glu Thr Asn Gln Thr
1               5                   10

<210> SEQ ID NO 80
<211> LENGTH: 10
<212> TYPE: PRT
<213> ORGANISM: Homo sapiens

<400> SEQUENCE: 80

Tyr Arg Glu Asn His Asn Asn Lys Lys
1               5                   10

<210> SEQ ID NO 81
<211> LENGTH: 10
<212> TYPE: PRT
<213> ORGANISM: Homo sapiens

<400> SEQUENCE: 81

Ile Leu Glu Asn Asn Ile Gly Asn Arg Met
1               5                   10

<210> SEQ ID NO 82
<211> LENGTH: 10
<212> TYPE: PRT
<213> ORGANISM: Homo sapiens

<400> SEQUENCE: 82

Phe Ala Glu Thr Gly Asp His Ser Arg Ser
1               5                   10

<210> SEQ ID NO 83
<211> LENGTH: 10
<212> TYPE: PRT
<213> ORGANISM: Homo sapiens

<400> SEQUENCE: 83

Glu Ser Asp Phe Ala Val Asp Asn Val Gly
1               5                   10
```

<210> SEQ ID NO 84
<211> LENGTH: 10
<212> TYPE: PRT
<213> ORGANISM: Homo sapiens

<400> SEQUENCE: 84

Glu Ser Asp Ser Ser Leu Ser Ser Thr
1               5                   10

<210> SEQ ID NO 85
<211> LENGTH: 10
<212> TYPE: PRT
<213> ORGANISM: Homo sapiens

<400> SEQUENCE: 85

Gly Ser Leu Cys Thr Gly Asp Ile Lys Arg
1               5                   10

<210> SEQ ID NO 86
<211> LENGTH: 10
<212> TYPE: PRT
<213> ORGANISM: Homo sapiens

<400> SEQUENCE: 86

Gln Ser Asp Trp Phe Tyr Glu Lys Glu Ser
1               5                   10

<210> SEQ ID NO 87
<211> LENGTH: 10
<212> TYPE: PRT
<213> ORGANISM: Homo sapiens

<400> SEQUENCE: 87

Ser Ser Leu Glu Glu Pro Ser Lys Asp Tyr
1               5                   10

<210> SEQ ID NO 88
<211> LENGTH: 10
<212> TYPE: PRT
<213> ORGANISM: Homo sapiens

<400> SEQUENCE: 88

Gly Ser Asp Ser Ser Leu Glu Glu Pro Ser
1               5                   10

<210> SEQ ID NO 89
<211> LENGTH: 9
<212> TYPE: PRT
<213> ORGANISM: Homo sapiens

<400> SEQUENCE: 89

Ser Ile Leu Thr Gly Ser Phe Pro Leu
1               5

<210> SEQ ID NO 90
<211> LENGTH: 9
<212> TYPE: PRT
<213> ORGANISM: Homo sapiens

<400> SEQUENCE: 90

Arg Met Leu Gln Asn Met Gly Trp Thr
1               5

<210> SEQ ID NO 91
<211> LENGTH: 9

```
<212> TYPE: PRT
<213> ORGANISM: Homo sapiens

<400> SEQUENCE: 91

Leu Val His Asp Leu Val Ser Ala Leu
1               5

<210> SEQ ID NO 92
<211> LENGTH: 9
<212> TYPE: PRT
<213> ORGANISM: Homo sapiens

<400> SEQUENCE: 92

Ser Leu Ser Ser Thr Asp Ala Gly Leu
1               5

<210> SEQ ID NO 93
<211> LENGTH: 9
<212> TYPE: PRT
<213> ORGANISM: Homo sapiens

<400> SEQUENCE: 93

Lys Ile Gln Asp Glu Gly Val Val Leu
1               5

<210> SEQ ID NO 94
<211> LENGTH: 9
<212> TYPE: PRT
<213> ORGANISM: Homo sapiens

<400> SEQUENCE: 94

Phe Val Gly Glu Asn Ala Gln Pro Ile
1               5

<210> SEQ ID NO 95
<211> LENGTH: 9
<212> TYPE: PRT
<213> ORGANISM: Homo sapiens

<400> SEQUENCE: 95

Ile Leu Thr Gly Ser Phe Pro Leu Met
1               5

<210> SEQ ID NO 96
<211> LENGTH: 9
<212> TYPE: PRT
<213> ORGANISM: Homo sapiens

<400> SEQUENCE: 96

Lys Met Glu Cys Glu Glu Gln Lys Val
1               5

<210> SEQ ID NO 97
<211> LENGTH: 9
<212> TYPE: PRT
<213> ORGANISM: Homo sapiens

<400> SEQUENCE: 97

Lys Gly Leu Gly Leu Gly Phe Pro Leu
1               5

<210> SEQ ID NO 98
<211> LENGTH: 9
<212> TYPE: PRT
<213> ORGANISM: Homo sapiens
```

```
<400> SEQUENCE: 98

Gly Leu Gly Arg Asp Gly Lys Gly Ile
1               5

<210> SEQ ID NO 99
<211> LENGTH: 9
<212> TYPE: PRT
<213> ORGANISM: Homo sapiens

<400> SEQUENCE: 99

Ser Met Val Pro Ile Pro Gly Pro Val
1               5

<210> SEQ ID NO 100
<211> LENGTH: 9
<212> TYPE: PRT
<213> ORGANISM: Homo sapiens

<400> SEQUENCE: 100

Gly Ile Ser Glu Pro Ile Gln Ala Met
1               5

<210> SEQ ID NO 101
<211> LENGTH: 9
<212> TYPE: PRT
<213> ORGANISM: Homo sapiens

<400> SEQUENCE: 101

Ser Met His Leu Gly Ser Leu Cys Thr
1               5

<210> SEQ ID NO 102
<211> LENGTH: 9
<212> TYPE: PRT
<213> ORGANISM: Homo sapiens

<400> SEQUENCE: 102

Lys Ile Ile Arg Gln Gly Pro Lys Ile
1               5

<210> SEQ ID NO 103
<211> LENGTH: 9
<212> TYPE: PRT
<213> ORGANISM: Homo sapiens

<400> SEQUENCE: 103

Pro Leu Trp His Glu Ser Asp Phe Ala
1               5

<210> SEQ ID NO 104
<211> LENGTH: 9
<212> TYPE: PRT
<213> ORGANISM: Homo sapiens

<400> SEQUENCE: 104

Tyr Gln Glu Phe Thr Lys Asn Lys Val
1               5

<210> SEQ ID NO 105
<211> LENGTH: 9
<212> TYPE: PRT
<213> ORGANISM: Homo sapiens

<400> SEQUENCE: 105

Met Gly Trp Thr Pro Gly Ser Gly Leu
```

<210> SEQ ID NO 106
<211> LENGTH: 9
<212> TYPE: PRT
<213> ORGANISM: Homo sapiens

<400> SEQUENCE: 106

Thr Met Thr Gln Pro Pro Glu Gly Cys
 1               5

<210> SEQ ID NO 107
<211> LENGTH: 9
<212> TYPE: PRT
<213> ORGANISM: Homo sapiens

<400> SEQUENCE: 107

Thr Glu His Asp Gln His Gln Leu Leu
 1               5

<210> SEQ ID NO 108
<211> LENGTH: 9
<212> TYPE: PRT
<213> ORGANISM: Homo sapiens

<400> SEQUENCE: 108

Tyr Asn Val His His Pro Trp Glu Thr
 1               5

<210> SEQ ID NO 109
<211> LENGTH: 9
<212> TYPE: PRT
<213> ORGANISM: Homo sapiens

<400> SEQUENCE: 109

Gln Ala Met Gln Arg Pro Lys Gly Leu
 1               5

<210> SEQ ID NO 110
<211> LENGTH: 9
<212> TYPE: PRT
<213> ORGANISM: Homo sapiens

<400> SEQUENCE: 110

Ser Ser Thr Asp Ala Gly Leu Phe Thr
 1               5

<210> SEQ ID NO 111
<211> LENGTH: 9
<212> TYPE: PRT
<213> ORGANISM: Homo sapiens

<400> SEQUENCE: 111

Ala Gln Pro Ile Leu Glu Asn Asn Ile
 1               5

<210> SEQ ID NO 112
<211> LENGTH: 9
<212> TYPE: PRT
<213> ORGANISM: Homo sapiens

<400> SEQUENCE: 112

Gly Gly Ala Cys Gly Ile Thr Gly Val
 1               5

```
<210> SEQ ID NO 113
<211> LENGTH: 9
<212> TYPE: PRT
<213> ORGANISM: Homo sapiens

<400> SEQUENCE: 113

Met Ala Val Asp Leu Pro Gln Asp Ile
1               5

<210> SEQ ID NO 114
<211> LENGTH: 9
<212> TYPE: PRT
<213> ORGANISM: Homo sapiens

<400> SEQUENCE: 114

Leu Glu Ser Glu Glu Thr Asn Gln Thr
1               5

<210> SEQ ID NO 115
<211> LENGTH: 9
<212> TYPE: PRT
<213> ORGANISM: Homo sapiens

<400> SEQUENCE: 115

Arg Ala Tyr Gln Tyr Gln Glu Phe Thr
1               5

<210> SEQ ID NO 116
<211> LENGTH: 9
<212> TYPE: PRT
<213> ORGANISM: Homo sapiens

<400> SEQUENCE: 116

Glu Leu Val His Asp Leu Val Ser Ala
1               5

<210> SEQ ID NO 117
<211> LENGTH: 9
<212> TYPE: PRT
<213> ORGANISM: Homo sapiens

<400> SEQUENCE: 117

Arg Thr Leu Arg Arg Arg Arg Lys Val
1               5

<210> SEQ ID NO 118
<211> LENGTH: 9
<212> TYPE: PRT
<213> ORGANISM: Homo sapiens

<400> SEQUENCE: 118

Lys Glu Ser Gly Gly Ala Cys Gly Ile
1               5

<210> SEQ ID NO 119
<211> LENGTH: 10
<212> TYPE: PRT
<213> ORGANISM: Homo sapiens

<400> SEQUENCE: 119

Leu Met Ser Glu Ser Asp Ser Ser Leu
1               5                   10

<210> SEQ ID NO 120
<211> LENGTH: 10
<212> TYPE: PRT
```

```
<213> ORGANISM: Homo sapiens

<400> SEQUENCE: 120

Cys Leu Ser Glu Gly Ser Asp Ser Ser Leu
1               5                   10

<210> SEQ ID NO 121
<211> LENGTH: 10
<212> TYPE: PRT
<213> ORGANISM: Homo sapiens

<400> SEQUENCE: 121

Pro Leu Trp His Glu Ser Asp Phe Ala Val
1               5                   10

<210> SEQ ID NO 122
<211> LENGTH: 10
<212> TYPE: PRT
<213> ORGANISM: Homo sapiens

<400> SEQUENCE: 122

Asn Met Gly Trp Thr Pro Gly Ser Gly Leu
1               5                   10

<210> SEQ ID NO 123
<211> LENGTH: 10
<212> TYPE: PRT
<213> ORGANISM: Homo sapiens

<400> SEQUENCE: 123

Ala Met Gln Arg Pro Lys Gly Leu Gly Leu
1               5                   10

<210> SEQ ID NO 124
<211> LENGTH: 10
<212> TYPE: PRT
<213> ORGANISM: Homo sapiens

<400> SEQUENCE: 124

Phe Val Gly Glu Asn Ala Gln Pro Ile Leu
1               5                   10

<210> SEQ ID NO 125
<211> LENGTH: 10
<212> TYPE: PRT
<213> ORGANISM: Homo sapiens

<400> SEQUENCE: 125

Arg Leu His Gly Met Ser Ser Lys Asn Ile
1               5                   10

<210> SEQ ID NO 126
<211> LENGTH: 10
<212> TYPE: PRT
<213> ORGANISM: Homo sapiens

<400> SEQUENCE: 126

Arg Met Ala Val Asp Leu Pro Gln Asp Ile
1               5                   10

<210> SEQ ID NO 127
<211> LENGTH: 10
<212> TYPE: PRT
<213> ORGANISM: Homo sapiens

<400> SEQUENCE: 127
```

Gly Leu Gly Phe Pro Leu Pro Lys Ser Thr
1               5                   10

<210> SEQ ID NO 128
<211> LENGTH: 10
<212> TYPE: PRT
<213> ORGANISM: Homo sapiens

<400> SEQUENCE: 128

Ser Ile Leu Thr Gly Ser Phe Pro Leu Met
1               5                   10

<210> SEQ ID NO 129
<211> LENGTH: 10
<212> TYPE: PRT
<213> ORGANISM: Homo sapiens

<400> SEQUENCE: 129

Glu Leu Val His Asp Leu Val Ser Ala Leu
1               5                   10

<210> SEQ ID NO 130
<211> LENGTH: 10
<212> TYPE: PRT
<213> ORGANISM: Homo sapiens

<400> SEQUENCE: 130

Ile Gln Ala Met Gln Arg Pro Lys Gly Leu
1               5                   10

<210> SEQ ID NO 131
<211> LENGTH: 10
<212> TYPE: PRT
<213> ORGANISM: Homo sapiens

<400> SEQUENCE: 131

Asn Val Pro Asp Pro Val Phe Glu Ser Ile
1               5                   10

<210> SEQ ID NO 132
<211> LENGTH: 10
<212> TYPE: PRT
<213> ORGANISM: Homo sapiens

<400> SEQUENCE: 132

Phe Ala Val Asp Asn Val Gly Asn Arg Thr
1               5                   10

<210> SEQ ID NO 133
<211> LENGTH: 10
<212> TYPE: PRT
<213> ORGANISM: Homo sapiens

<400> SEQUENCE: 133

Lys Ser Gly Gly Thr Pro Thr Ser Met Val
1               5                   10

<210> SEQ ID NO 134
<211> LENGTH: 10
<212> TYPE: PRT
<213> ORGANISM: Homo sapiens

<400> SEQUENCE: 134

Asn Ile Gly Asn Arg Met Leu Gln Asn Met
1               5                   10

<210> SEQ ID NO 135
<211> LENGTH: 10
<212> TYPE: PRT
<213> ORGANISM: Homo sapiens

<400> SEQUENCE: 135

Arg Gly Phe Gln Ala Arg Leu Ser Arg Leu
1               5                   10

<210> SEQ ID NO 136
<211> LENGTH: 10
<212> TYPE: PRT
<213> ORGANISM: Homo sapiens

<400> SEQUENCE: 136

Ser Gly Gly Ala Cys Gly Ile Thr Gly Val
1               5                   10

<210> SEQ ID NO 137
<211> LENGTH: 10
<212> TYPE: PRT
<213> ORGANISM: Homo sapiens

<400> SEQUENCE: 137

Glu Leu Asp Lys Asn Val Pro Asp Pro Val
1               5                   10

<210> SEQ ID NO 138
<211> LENGTH: 10
<212> TYPE: PRT
<213> ORGANISM: Homo sapiens

<400> SEQUENCE: 138

Phe Pro Leu Pro Lys Ser Thr Ser Ala Thr
1               5                   10

<210> SEQ ID NO 139
<211> LENGTH: 10
<212> TYPE: PRT
<213> ORGANISM: Homo sapiens

<400> SEQUENCE: 139

Val Leu Glu Ser Glu Glu Thr Asn Gln Thr
1               5                   10

<210> SEQ ID NO 140
<211> LENGTH: 10
<212> TYPE: PRT
<213> ORGANISM: Homo sapiens

<400> SEQUENCE: 140

Arg Gln Thr Ser Met His Leu Gly Ser Leu
1               5                   10

<210> SEQ ID NO 141
<211> LENGTH: 10
<212> TYPE: PRT
<213> ORGANISM: Homo sapiens

<400> SEQUENCE: 141

Leu Pro Gly Pro Thr Thr Ala Gly Phe Val
1               5                   10

<210> SEQ ID NO 142

```
<211> LENGTH: 10
<212> TYPE: PRT
<213> ORGANISM: Homo sapiens

<400> SEQUENCE: 142

Ile Leu Glu Asn Asn Ile Gly Asn Arg Met
1               5                   10

<210> SEQ ID NO 143
<211> LENGTH: 10
<212> TYPE: PRT
<213> ORGANISM: Homo sapiens

<400> SEQUENCE: 143

Ser Ser Leu Ser Ser Thr Asp Ala Gly Leu
1               5                   10

<210> SEQ ID NO 144
<211> LENGTH: 10
<212> TYPE: PRT
<213> ORGANISM: Homo sapiens

<400> SEQUENCE: 144

Ser Ala Leu Glu Glu Ser Ser Glu Gln Ala
1               5                   10

<210> SEQ ID NO 145
<211> LENGTH: 10
<212> TYPE: PRT
<213> ORGANISM: Homo sapiens

<400> SEQUENCE: 145

Asn Gln Thr Asn Lys Asp Lys Met Glu Cys
1               5                   10

<210> SEQ ID NO 146
<211> LENGTH: 10
<212> TYPE: PRT
<213> ORGANISM: Homo sapiens

<400> SEQUENCE: 146

Ile Leu Thr Gly Ser Phe Pro Leu Met Ser
1               5                   10

<210> SEQ ID NO 147
<211> LENGTH: 10
<212> TYPE: PRT
<213> ORGANISM: Homo sapiens

<400> SEQUENCE: 147

Leu Ser Ser Thr Asp Ala Gly Leu Phe Thr
1               5                   10

<210> SEQ ID NO 148
<211> LENGTH: 10
<212> TYPE: PRT
<213> ORGANISM: Homo sapiens

<400> SEQUENCE: 148

Arg Pro Ser Ser Asn Leu Asn Asn Asn Val
1               5                   10

<210> SEQ ID NO 149
<211> LENGTH: 9
<212> TYPE: PRT
<213> ORGANISM: Homo sapiens
```

<400> SEQUENCE: 149

Gly Met Ser Ser Lys Asn Ile Lys Lys
 1               5

<210> SEQ ID NO 150
<211> LENGTH: 9
<212> TYPE: PRT
<213> ORGANISM: Homo sapiens

<400> SEQUENCE: 150

Gly Leu Phe Thr Asn Asp Glu Gly Arg
 1               5

<210> SEQ ID NO 151
<211> LENGTH: 9
<212> TYPE: PRT
<213> ORGANISM: Homo sapiens

<400> SEQUENCE: 151

Thr Leu Arg Arg Arg Arg Lys Val Lys
 1               5

<210> SEQ ID NO 152
<211> LENGTH: 9
<212> TYPE: PRT
<213> ORGANISM: Homo sapiens

<400> SEQUENCE: 152

Asp Leu Pro Gln Asp Ile Ser Asn Lys
 1               5

<210> SEQ ID NO 153
<211> LENGTH: 9
<212> TYPE: PRT
<213> ORGANISM: Homo sapiens

<400> SEQUENCE: 153

Ser Leu Cys Thr Gly Asp Ile Lys Arg
 1               5

<210> SEQ ID NO 154
<211> LENGTH: 9
<212> TYPE: PRT
<213> ORGANISM: Homo sapiens

<400> SEQUENCE: 154

Asn Leu Asn Asn Asn Val Arg Gly Lys
 1               5

<210> SEQ ID NO 155
<211> LENGTH: 9
<212> TYPE: PRT
<213> ORGANISM: Homo sapiens

<400> SEQUENCE: 155

Glu Gln Ser Asp Trp Phe Tyr Glu Lys
 1               5

<210> SEQ ID NO 156
<211> LENGTH: 9
<212> TYPE: PRT
<213> ORGANISM: Homo sapiens

<400> SEQUENCE: 156

```
Ser Leu Glu Glu Pro Ser Lys Asp Tyr
1               5
```

<210> SEQ ID NO 157
<211> LENGTH: 9
<212> TYPE: PRT
<213> ORGANISM: Homo sapiens

<400> SEQUENCE: 157

```
Leu Leu Arg Asp Asn Arg Ala Glu Arg
1               5
```

<210> SEQ ID NO 158
<211> LENGTH: 9
<212> TYPE: PRT
<213> ORGANISM: Homo sapiens

<400> SEQUENCE: 158

```
Ile Leu Glu Asn Asn Ile Gly Asn Arg
1               5
```

<210> SEQ ID NO 159
<211> LENGTH: 9
<212> TYPE: PRT
<213> ORGANISM: Homo sapiens

<400> SEQUENCE: 159

```
Ala Thr Thr Thr Pro Asn Ala Gly Lys
1               5
```

<210> SEQ ID NO 160
<211> LENGTH: 9
<212> TYPE: PRT
<213> ORGANISM: Homo sapiens

<400> SEQUENCE: 160

```
Ile Leu Thr Gly Ser Phe Pro Leu Met
1               5
```

<210> SEQ ID NO 161
<211> LENGTH: 9
<212> TYPE: PRT
<213> ORGANISM: Homo sapiens

<400> SEQUENCE: 161

```
Gly Leu Gly Arg Asp Gly Lys Gly Ile
1               5
```

<210> SEQ ID NO 162
<211> LENGTH: 9
<212> TYPE: PRT
<213> ORGANISM: Homo sapiens

<400> SEQUENCE: 162

```
Asn Val Gly Asn Arg Thr Leu Arg Arg
1               5
```

<210> SEQ ID NO 163
<211> LENGTH: 9
<212> TYPE: PRT
<213> ORGANISM: Homo sapiens

<400> SEQUENCE: 163

```
Ser Leu Ser Ser Thr Asp Ala Gly Leu
1               5
```

<210> SEQ ID NO 164
<211> LENGTH: 9
<212> TYPE: PRT
<213> ORGANISM: Homo sapiens

<400> SEQUENCE: 164

Pro Leu Met Ser His Pro Ser Arg Arg
1               5

<210> SEQ ID NO 165
<211> LENGTH: 9
<212> TYPE: PRT
<213> ORGANISM: Homo sapiens

<400> SEQUENCE: 165

Trp Thr Pro Gly Ser Gly Leu Gly Arg
1               5

<210> SEQ ID NO 166
<211> LENGTH: 9
<212> TYPE: PRT
<213> ORGANISM: Homo sapiens

<400> SEQUENCE: 166

Lys Met Glu Cys Glu Glu Gln Lys Val
1               5

<210> SEQ ID NO 167
<211> LENGTH: 9
<212> TYPE: PRT
<213> ORGANISM: Homo sapiens

<400> SEQUENCE: 167

Lys Glu Asp Pro Thr Glu Leu Asp Lys
1               5

<210> SEQ ID NO 168
<211> LENGTH: 9
<212> TYPE: PRT
<213> ORGANISM: Homo sapiens

<400> SEQUENCE: 168

Gly Ser Leu Cys Thr Gly Asp Ile Lys
1               5

<210> SEQ ID NO 169
<211> LENGTH: 9
<212> TYPE: PRT
<213> ORGANISM: Homo sapiens

<400> SEQUENCE: 169

Gly Ile Thr Gly Val Val Pro Trp Trp
1               5

<210> SEQ ID NO 170
<211> LENGTH: 9
<212> TYPE: PRT
<213> ORGANISM: Homo sapiens

<400> SEQUENCE: 170

Pro Ile Pro Gly Pro Val Gly Asn Lys
1               5

<210> SEQ ID NO 171
<211> LENGTH: 9

<212> TYPE: PRT
<213> ORGANISM: Homo sapiens

<400> SEQUENCE: 171

Lys Val Lys Lys Arg Lys Leu Lys Ile
1               5

<210> SEQ ID NO 172
<211> LENGTH: 9
<212> TYPE: PRT
<213> ORGANISM: Homo sapiens

<400> SEQUENCE: 172

Thr Met Thr Gln Pro Pro Glu Gly Cys
1               5

<210> SEQ ID NO 173
<211> LENGTH: 9
<212> TYPE: PRT
<213> ORGANISM: Homo sapiens

<400> SEQUENCE: 173

Ala Leu Glu Glu Ser Ser Glu Gln Ala
1               5

<210> SEQ ID NO 174
<211> LENGTH: 9
<212> TYPE: PRT
<213> ORGANISM: Homo sapiens

<400> SEQUENCE: 174

Phe Thr Lys Asn Lys Val Lys Lys Arg
1               5

<210> SEQ ID NO 175
<211> LENGTH: 9
<212> TYPE: PRT
<213> ORGANISM: Homo sapiens

<400> SEQUENCE: 175

Cys Pro Leu Lys Arg Gln Ala Arg Lys
1               5

<210> SEQ ID NO 176
<211> LENGTH: 9
<212> TYPE: PRT
<213> ORGANISM: Homo sapiens

<400> SEQUENCE: 176

Gly Ser Gly Leu Gly Arg Asp Gly Lys
1               5

<210> SEQ ID NO 177
<211> LENGTH: 9
<212> TYPE: PRT
<213> ORGANISM: Homo sapiens

<400> SEQUENCE: 177

Lys Ile Ile Arg Gln Gly Pro Lys Ile
1               5

<210> SEQ ID NO 178
<211> LENGTH: 9
<212> TYPE: PRT
<213> ORGANISM: Homo sapiens

```
<400> SEQUENCE: 178

Gly Leu Gly Phe Pro Leu Pro Lys Ser
 1               5

<210> SEQ ID NO 179
<211> LENGTH: 10
<212> TYPE: PRT
<213> ORGANISM: Homo sapiens

<400> SEQUENCE: 179

Gly Leu Gly Leu Gly Phe Pro Leu Pro Lys
 1               5                  10

<210> SEQ ID NO 180
<211> LENGTH: 10
<212> TYPE: PRT
<213> ORGANISM: Homo sapiens

<400> SEQUENCE: 180

Lys Leu Lys Ile Ile Arg Gln Gly Pro Lys
 1               5                  10

<210> SEQ ID NO 181
<211> LENGTH: 10
<212> TYPE: PRT
<213> ORGANISM: Homo sapiens

<400> SEQUENCE: 181

Ser Leu Glu Glu Pro Ser Lys Asp Tyr Arg
 1               5                  10

<210> SEQ ID NO 182
<211> LENGTH: 10
<212> TYPE: PRT
<213> ORGANISM: Homo sapiens

<400> SEQUENCE: 182

Ala Leu Glu Glu Ser Ser Glu Gln Ala Arg
 1               5                  10

<210> SEQ ID NO 183
<211> LENGTH: 10
<212> TYPE: PRT
<213> ORGANISM: Homo sapiens

<400> SEQUENCE: 183

Gln Leu Leu Arg Asp Asn Arg Ala Glu Arg
 1               5                  10

<210> SEQ ID NO 184
<211> LENGTH: 10
<212> TYPE: PRT
<213> ORGANISM: Homo sapiens

<400> SEQUENCE: 184

Tyr Gln Tyr Gln Glu Phe Thr Lys Asn Lys
 1               5                  10

<210> SEQ ID NO 185
<211> LENGTH: 10
<212> TYPE: PRT
<213> ORGANISM: Homo sapiens

<400> SEQUENCE: 185

Ile Thr Gly Val Val Pro Trp Trp Glu Lys
```

```
                   1               5                  10
```

<210> SEQ ID NO 186
<211> LENGTH: 10
<212> TYPE: PRT
<213> ORGANISM: Homo sapiens

<400> SEQUENCE: 186

```
Thr Leu Arg Arg Arg Arg Lys Val Lys Arg
 1               5                  10
```

<210> SEQ ID NO 187
<211> LENGTH: 10
<212> TYPE: PRT
<213> ORGANISM: Homo sapiens

<400> SEQUENCE: 187

```
Asp Met Asp Ser Asp Arg Ala Tyr Gln Tyr
 1               5                  10
```

<210> SEQ ID NO 188
<211> LENGTH: 10
<212> TYPE: PRT
<213> ORGANISM: Homo sapiens

<400> SEQUENCE: 188

```
Arg Ala Tyr Gln Tyr Gln Glu Phe Thr Lys
 1               5                  10
```

<210> SEQ ID NO 189
<211> LENGTH: 10
<212> TYPE: PRT
<213> ORGANISM: Homo sapiens

<400> SEQUENCE: 189

```
Ser Leu Cys Thr Gly Asp Ile Lys Arg Arg
 1               5                  10
```

<210> SEQ ID NO 190
<211> LENGTH: 10
<212> TYPE: PRT
<213> ORGANISM: Homo sapiens

<400> SEQUENCE: 190

```
Thr Met Thr Gln Pro Pro Glu Gly Cys Arg
 1               5                  10
```

<210> SEQ ID NO 191
<211> LENGTH: 10
<212> TYPE: PRT
<213> ORGANISM: Homo sapiens

<400> SEQUENCE: 191

```
Asp Leu Pro Gln Asp Ile Ser Asn Lys Arg
 1               5                  10
```

<210> SEQ ID NO 192
<211> LENGTH: 10
<212> TYPE: PRT
<213> ORGANISM: Homo sapiens

<400> SEQUENCE: 192

```
Asn Leu Asn Asn Asn Val Arg Gly Lys Arg
 1               5                  10
```

```
<210> SEQ ID NO 193
<211> LENGTH: 10
<212> TYPE: PRT
<213> ORGANISM: Homo sapiens

<400> SEQUENCE: 193

Ala Met Gln Arg Pro Lys Gly Leu Gly Leu
 1               5                  10

<210> SEQ ID NO 194
<211> LENGTH: 10
<212> TYPE: PRT
<213> ORGANISM: Homo sapiens

<400> SEQUENCE: 194

Cys Leu Ser Glu Gly Ser Asp Ser Ser Leu
 1               5                  10

<210> SEQ ID NO 195
<211> LENGTH: 10
<212> TYPE: PRT
<213> ORGANISM: Homo sapiens

<400> SEQUENCE: 195

Asn Met Gly Trp Thr Pro Gly Ser Gly Leu
 1               5                  10

<210> SEQ ID NO 196
<211> LENGTH: 10
<212> TYPE: PRT
<213> ORGANISM: Homo sapiens

<400> SEQUENCE: 196

Leu Met Ser Glu Ser Asp Ser Ser Ser Leu
 1               5                  10

<210> SEQ ID NO 197
<211> LENGTH: 10
<212> TYPE: PRT
<213> ORGANISM: Homo sapiens

<400> SEQUENCE: 197

Glu Leu Val His Asp Leu Val Ser Ala Leu
 1               5                  10

<210> SEQ ID NO 198
<211> LENGTH: 10
<212> TYPE: PRT
<213> ORGANISM: Homo sapiens

<400> SEQUENCE: 198

Arg Thr Leu Arg Arg Arg Arg Lys Val Lys
 1               5                  10

<210> SEQ ID NO 199
<211> LENGTH: 10
<212> TYPE: PRT
<213> ORGANISM: Homo sapiens

<400> SEQUENCE: 199

Phe Thr Lys Asn Lys Val Lys Lys Arg Lys
 1               5                  10

<210> SEQ ID NO 200
<211> LENGTH: 10
<212> TYPE: PRT
```

<213> ORGANISM: Homo sapiens

<400> SEQUENCE: 200

Val Pro Ile Pro Gly Pro Val Gly Asn Lys
1               5                   10

<210> SEQ ID NO 201
<211> LENGTH: 10
<212> TYPE: PRT
<213> ORGANISM: Homo sapiens

<400> SEQUENCE: 201

Ser Leu Ser Ser Thr Asp Ala Gly Leu Phe
1               5                   10

<210> SEQ ID NO 202
<211> LENGTH: 10
<212> TYPE: PRT
<213> ORGANISM: Homo sapiens

<400> SEQUENCE: 202

Arg Met Ala Val Asp Leu Pro Gln Asp Ile
1               5                   10

<210> SEQ ID NO 203
<211> LENGTH: 10
<212> TYPE: PRT
<213> ORGANISM: Homo sapiens

<400> SEQUENCE: 203

Asp Glu Gln Ser Asp Trp Phe Tyr Glu Lys
1               5                   10

<210> SEQ ID NO 204
<211> LENGTH: 10
<212> TYPE: PRT
<213> ORGANISM: Homo sapiens

<400> SEQUENCE: 204

Arg Leu His Gly Met Ser Ser Lys Asn Ile
1               5                   10

<210> SEQ ID NO 205
<211> LENGTH: 10
<212> TYPE: PRT
<213> ORGANISM: Homo sapiens

<400> SEQUENCE: 205

Ile Leu Thr Gly Ser Phe Pro Leu Met Ser
1               5                   10

<210> SEQ ID NO 206
<211> LENGTH: 10
<212> TYPE: PRT
<213> ORGANISM: Homo sapiens

<400> SEQUENCE: 206

Pro Leu Trp His Glu Ser Asp Phe Ala Val
1               5                   10

<210> SEQ ID NO 207
<211> LENGTH: 10
<212> TYPE: PRT
<213> ORGANISM: Homo sapiens

<400> SEQUENCE: 207

Ser Ala Thr Thr Thr Pro Asn Ala Gly Lys
1               5                   10

<210> SEQ ID NO 208
<211> LENGTH: 10
<212> TYPE: PRT
<213> ORGANISM: Homo sapiens

<400> SEQUENCE: 208

Tyr Gln Glu Phe Thr Lys Asn Lys Val Lys
1               5                   10

<210> SEQ ID NO 209
<211> LENGTH: 9
<212> TYPE: PRT
<213> ORGANISM: Homo sapiens

<400> SEQUENCE: 209

Gly Met Ser Ser Lys Asn Ile Lys Lys
1               5

<210> SEQ ID NO 210
<211> LENGTH: 9
<212> TYPE: PRT
<213> ORGANISM: Homo sapiens

<400> SEQUENCE: 210

Ala Tyr Gln Tyr Gln Glu Phe Thr Lys
1               5

<210> SEQ ID NO 211
<211> LENGTH: 9
<212> TYPE: PRT
<213> ORGANISM: Homo sapiens

<400> SEQUENCE: 211

Ala Thr Thr Thr Pro Asn Ala Gly Lys
1               5

<210> SEQ ID NO 212
<211> LENGTH: 9
<212> TYPE: PRT
<213> ORGANISM: Homo sapiens

<400> SEQUENCE: 212

Asn Val Gly Asn Arg Thr Leu Arg Arg
1               5

<210> SEQ ID NO 213
<211> LENGTH: 9
<212> TYPE: PRT
<213> ORGANISM: Homo sapiens

<400> SEQUENCE: 213

Gly Leu Phe Thr Asn Asp Glu Gly Arg
1               5

<210> SEQ ID NO 214
<211> LENGTH: 9
<212> TYPE: PRT
<213> ORGANISM: Homo sapiens

<400> SEQUENCE: 214

Trp Thr Pro Gly Ser Gly Leu Gly Arg
1               5

```
<210> SEQ ID NO 215
<211> LENGTH: 9
<212> TYPE: PRT
<213> ORGANISM: Homo sapiens

<400> SEQUENCE: 215

Glu Gln Ser Asp Trp Phe Tyr Glu Lys
 1               5

<210> SEQ ID NO 216
<211> LENGTH: 9
<212> TYPE: PRT
<213> ORGANISM: Homo sapiens

<400> SEQUENCE: 216

Lys Glu Asp Pro Thr Glu Leu Asp Lys
 1               5

<210> SEQ ID NO 217
<211> LENGTH: 9
<212> TYPE: PRT
<213> ORGANISM: Homo sapiens

<400> SEQUENCE: 217

Cys Pro Leu Lys Arg Gln Ala Arg Lys
 1               5

<210> SEQ ID NO 218
<211> LENGTH: 9
<212> TYPE: PRT
<213> ORGANISM: Homo sapiens

<400> SEQUENCE: 218

Thr Leu Arg Arg Arg Arg Lys Val Lys
 1               5

<210> SEQ ID NO 219
<211> LENGTH: 9
<212> TYPE: PRT
<213> ORGANISM: Homo sapiens

<400> SEQUENCE: 219

Gln Tyr Gln Glu Phe Thr Lys Asn Lys
 1               5

<210> SEQ ID NO 220
<211> LENGTH: 9
<212> TYPE: PRT
<213> ORGANISM: Homo sapiens

<400> SEQUENCE: 220

Met Thr Gln Pro Pro Glu Gly Cys Arg
 1               5

<210> SEQ ID NO 221
<211> LENGTH: 9
<212> TYPE: PRT
<213> ORGANISM: Homo sapiens

<400> SEQUENCE: 221

Gln Ala Arg Lys Arg Arg Gly Arg Lys
 1               5

<210> SEQ ID NO 222
```

```
<211> LENGTH: 9
<212> TYPE: PRT
<213> ORGANISM: Homo sapiens

<400> SEQUENCE: 222

Arg Glu Asn His Asn Asn Asn Lys Lys
1               5

<210> SEQ ID NO 223
<211> LENGTH: 9
<212> TYPE: PRT
<213> ORGANISM: Homo sapiens

<400> SEQUENCE: 223

Ser Leu Cys Thr Gly Asp Ile Lys Arg
1               5

<210> SEQ ID NO 224
<211> LENGTH: 9
<212> TYPE: PRT
<213> ORGANISM: Homo sapiens

<400> SEQUENCE: 224

Glu Thr Asn Gln Thr Asn Lys Asp Lys
1               5

<210> SEQ ID NO 225
<211> LENGTH: 9
<212> TYPE: PRT
<213> ORGANISM: Homo sapiens

<400> SEQUENCE: 225

Asp Leu Pro Gln Asp Ile Ser Asn Lys
1               5

<210> SEQ ID NO 226
<211> LENGTH: 9
<212> TYPE: PRT
<213> ORGANISM: Homo sapiens

<400> SEQUENCE: 226

Lys Val Lys Lys Arg Lys Leu Lys Ile
1               5

<210> SEQ ID NO 227
<211> LENGTH: 9
<212> TYPE: PRT
<213> ORGANISM: Homo sapiens

<400> SEQUENCE: 227

Phe Thr Lys Asn Lys Val Lys Lys Arg
1               5

<210> SEQ ID NO 228
<211> LENGTH: 9
<212> TYPE: PRT
<213> ORGANISM: Homo sapiens

<400> SEQUENCE: 228

Gly Ser Leu Cys Thr Gly Asp Ile Lys
1               5

<210> SEQ ID NO 229
<211> LENGTH: 9
<212> TYPE: PRT
<213> ORGANISM: Homo sapiens
```

<400> SEQUENCE: 229

Leu Leu Arg Asp Asn Arg Ala Glu Arg
1               5

<210> SEQ ID NO 230
<211> LENGTH: 9
<212> TYPE: PRT
<213> ORGANISM: Homo sapiens

<400> SEQUENCE: 230

Ile Leu Glu Asn Asn Ile Gly Asn Arg
1               5

<210> SEQ ID NO 231
<211> LENGTH: 9
<212> TYPE: PRT
<213> ORGANISM: Homo sapiens

<400> SEQUENCE: 231

Leu Gly Leu Gly Phe Pro Leu Pro Lys
1               5

<210> SEQ ID NO 232
<211> LENGTH: 9
<212> TYPE: PRT
<213> ORGANISM: Homo sapiens

<400> SEQUENCE: 232

Gly Ser Gly Leu Gly Arg Asp Gly Lys
1               5

<210> SEQ ID NO 233
<211> LENGTH: 9
<212> TYPE: PRT
<213> ORGANISM: Homo sapiens

<400> SEQUENCE: 233

Thr Gly Val Val Pro Trp Trp Glu Lys
1               5

<210> SEQ ID NO 234
<211> LENGTH: 9
<212> TYPE: PRT
<213> ORGANISM: Homo sapiens

<400> SEQUENCE: 234

Lys Val Lys Arg Met Ala Val Asp Leu
1               5

<210> SEQ ID NO 235
<211> LENGTH: 9
<212> TYPE: PRT
<213> ORGANISM: Homo sapiens

<400> SEQUENCE: 235

Ser Glu Glu Thr Asn Gln Thr Asn Lys
1               5

<210> SEQ ID NO 236
<211> LENGTH: 9
<212> TYPE: PRT
<213> ORGANISM: Homo sapiens

<400> SEQUENCE: 236

```
Phe Pro Leu Met Ser His Pro Ser Arg
 1               5

<210> SEQ ID NO 237
<211> LENGTH: 9
<212> TYPE: PRT
<213> ORGANISM: Homo sapiens

<400> SEQUENCE: 237

Gln Glu Phe Thr Lys Asn Lys Val Lys
 1               5

<210> SEQ ID NO 238
<211> LENGTH: 9
<212> TYPE: PRT
<213> ORGANISM: Homo sapiens

<400> SEQUENCE: 238

Glu Phe Thr Lys Asn Lys Val Lys Lys
 1               5

<210> SEQ ID NO 239
<211> LENGTH: 10
<212> TYPE: PRT
<213> ORGANISM: Homo sapiens

<400> SEQUENCE: 239

Arg Ala Tyr Gln Tyr Gln Glu Phe Thr Lys
 1               5                  10

<210> SEQ ID NO 240
<211> LENGTH: 10
<212> TYPE: PRT
<213> ORGANISM: Homo sapiens

<400> SEQUENCE: 240

Gly Leu Gly Leu Gly Phe Pro Leu Pro Lys
 1               5                  10

<210> SEQ ID NO 241
<211> LENGTH: 10
<212> TYPE: PRT
<213> ORGANISM: Homo sapiens

<400> SEQUENCE: 241

Arg Thr Leu Arg Arg Arg Arg Lys Val Lys
 1               5                  10

<210> SEQ ID NO 242
<211> LENGTH: 10
<212> TYPE: PRT
<213> ORGANISM: Homo sapiens

<400> SEQUENCE: 242

Ile Thr Gly Val Val Pro Trp Trp Glu Lys
 1               5                  10

<210> SEQ ID NO 243
<211> LENGTH: 10
<212> TYPE: PRT
<213> ORGANISM: Homo sapiens

<400> SEQUENCE: 243

Arg Gln Ala Arg Lys Arg Arg Gly Arg Lys
 1               5                  10
```

```
<210> SEQ ID NO 244
<211> LENGTH: 10
<212> TYPE: PRT
<213> ORGANISM: Homo sapiens

<400> SEQUENCE: 244

Lys Leu Lys Ile Ile Arg Gln Gly Pro Lys
1               5                   10

<210> SEQ ID NO 245
<211> LENGTH: 10
<212> TYPE: PRT
<213> ORGANISM: Homo sapiens

<400> SEQUENCE: 245

Tyr Gln Tyr Gln Glu Phe Thr Lys Asn Lys
1               5                   10

<210> SEQ ID NO 246
<211> LENGTH: 10
<212> TYPE: PRT
<213> ORGANISM: Homo sapiens

<400> SEQUENCE: 246

Phe Thr Lys Asn Lys Val Lys Lys Arg Lys
1               5                   10

<210> SEQ ID NO 247
<211> LENGTH: 10
<212> TYPE: PRT
<213> ORGANISM: Homo sapiens

<400> SEQUENCE: 247

Tyr Gln Glu Phe Thr Lys Asn Lys Val Lys
1               5                   10

<210> SEQ ID NO 248
<211> LENGTH: 10
<212> TYPE: PRT
<213> ORGANISM: Homo sapiens

<400> SEQUENCE: 248

Val Pro Ile Pro Gly Pro Val Gly Asn Lys
1               5                   10

<210> SEQ ID NO 249
<211> LENGTH: 10
<212> TYPE: PRT
<213> ORGANISM: Homo sapiens

<400> SEQUENCE: 249

Ser Ala Thr Thr Thr Pro Asn Ala Gly Lys
1               5                   10

<210> SEQ ID NO 250
<211> LENGTH: 10
<212> TYPE: PRT
<213> ORGANISM: Homo sapiens

<400> SEQUENCE: 250

Ser Cys Pro Leu Lys Arg Gln Ala Arg Lys
1               5                   10

<210> SEQ ID NO 251
<211> LENGTH: 10
```

<212> TYPE: PRT
<213> ORGANISM: Homo sapiens

<400> SEQUENCE: 251

Gln Glu Phe Thr Lys Asn Lys Val Lys Lys
1               5                   10

<210> SEQ ID NO 252
<211> LENGTH: 10
<212> TYPE: PRT
<213> ORGANISM: Homo sapiens

<400> SEQUENCE: 252

Asp Tyr Arg Glu Asn His Asn Asn Asn Lys
1               5                   10

<210> SEQ ID NO 253
<211> LENGTH: 10
<212> TYPE: PRT
<213> ORGANISM: Homo sapiens

<400> SEQUENCE: 253

Gln Leu Leu Arg Asp Asn Arg Ala Glu Arg
1               5                   10

<210> SEQ ID NO 254
<211> LENGTH: 10
<212> TYPE: PRT
<213> ORGANISM: Homo sapiens

<400> SEQUENCE: 254

Gly Phe Ala Glu Thr Gly Asp His Ser Arg
1               5                   10

<210> SEQ ID NO 255
<211> LENGTH: 10
<212> TYPE: PRT
<213> ORGANISM: Homo sapiens

<400> SEQUENCE: 255

Cys Thr Gly Asp Ile Lys Arg Arg Arg Lys
1               5                   10

<210> SEQ ID NO 256
<211> LENGTH: 10
<212> TYPE: PRT
<213> ORGANISM: Homo sapiens

<400> SEQUENCE: 256

Thr Leu Arg Arg Arg Arg Lys Val Lys Arg
1               5                   10

<210> SEQ ID NO 257
<211> LENGTH: 10
<212> TYPE: PRT
<213> ORGANISM: Homo sapiens

<400> SEQUENCE: 257

Ser Leu Glu Glu Pro Ser Lys Asp Tyr Arg
1               5                   10

<210> SEQ ID NO 258
<211> LENGTH: 10
<212> TYPE: PRT
<213> ORGANISM: Homo sapiens

<400> SEQUENCE: 258

His Gly Met Ser Ser Lys Asn Ile Lys Lys
1               5                   10

<210> SEQ ID NO 259
<211> LENGTH: 10
<212> TYPE: PRT
<213> ORGANISM: Homo sapiens

<400> SEQUENCE: 259

Asn Leu Asn Asn Asn Val Arg Gly Lys Arg
1               5                   10

<210> SEQ ID NO 260
<211> LENGTH: 10
<212> TYPE: PRT
<213> ORGANISM: Homo sapiens

<400> SEQUENCE: 260

Ala Leu Glu Glu Ser Ser Glu Gln Ala Arg
1               5                   10

<210> SEQ ID NO 261
<211> LENGTH: 10
<212> TYPE: PRT
<213> ORGANISM: Homo sapiens

<400> SEQUENCE: 261

Thr Met Thr Gln Pro Pro Glu Gly Cys Arg
1               5                   10

<210> SEQ ID NO 262
<211> LENGTH: 10
<212> TYPE: PRT
<213> ORGANISM: Homo sapiens

<400> SEQUENCE: 262

Lys Asn Lys Val Lys Lys Arg Lys Leu Lys
1               5                   10

<210> SEQ ID NO 263
<211> LENGTH: 10
<212> TYPE: PRT
<213> ORGANISM: Homo sapiens

<400> SEQUENCE: 263

Lys Asp Lys Met Glu Cys Glu Glu Gln Lys
1               5                   10

<210> SEQ ID NO 264
<211> LENGTH: 10
<212> TYPE: PRT
<213> ORGANISM: Homo sapiens

<400> SEQUENCE: 264

Arg Asp Asn Arg Ala Glu Arg Gly His Lys
1               5                   10

<210> SEQ ID NO 265
<211> LENGTH: 10
<212> TYPE: PRT
<213> ORGANISM: Homo sapiens

<400> SEQUENCE: 265

Phe Pro Leu Met Ser His Pro Ser Arg Arg

<210> SEQ ID NO 266
<211> LENGTH: 10
<212> TYPE: PRT
<213> ORGANISM: Homo sapiens

<400> SEQUENCE: 266

Asn Val Gly Asn Arg Thr Leu Arg Arg Arg
1               5                   10

<210> SEQ ID NO 267
<211> LENGTH: 10
<212> TYPE: PRT
<213> ORGANISM: Homo sapiens

<400> SEQUENCE: 267

Asn Val Arg Gly Lys Arg Pro Leu Trp His
1               5                   10

<210> SEQ ID NO 268
<211> LENGTH: 10
<212> TYPE: PRT
<213> ORGANISM: Homo sapiens

<400> SEQUENCE: 268

His Pro Ser Arg Arg Gly Phe Gln Ala Arg
1               5                   10

<210> SEQ ID NO 269
<211> LENGTH: 9
<212> TYPE: PRT
<213> ORGANISM: Homo sapiens

<400> SEQUENCE: 269

Gly Phe Gln Ala Arg Leu Ser Arg Leu
1               5

<210> SEQ ID NO 270
<211> LENGTH: 9
<212> TYPE: PRT
<213> ORGANISM: Homo sapiens

<400> SEQUENCE: 270

Lys Gly Leu Gly Leu Gly Phe Pro Leu
1               5

<210> SEQ ID NO 271
<211> LENGTH: 9
<212> TYPE: PRT
<213> ORGANISM: Homo sapiens

<400> SEQUENCE: 271

Lys Ile Gln Asp Glu Gly Val Val Leu
1               5

<210> SEQ ID NO 272
<211> LENGTH: 9
<212> TYPE: PRT
<213> ORGANISM: Homo sapiens

<400> SEQUENCE: 272

Arg Thr Glu His Asp Gln His Gln Leu
1               5

```
<210> SEQ ID NO 273
<211> LENGTH: 9
<212> TYPE: PRT
<213> ORGANISM: Homo sapiens

<400> SEQUENCE: 273

Lys Asn Lys Val Lys Lys Arg Lys Leu
1               5

<210> SEQ ID NO 274
<211> LENGTH: 9
<212> TYPE: PRT
<213> ORGANISM: Homo sapiens

<400> SEQUENCE: 274

Lys Val Lys Arg Met Ala Val Asp Leu
1               5

<210> SEQ ID NO 275
<211> LENGTH: 9
<212> TYPE: PRT
<213> ORGANISM: Homo sapiens

<400> SEQUENCE: 275

Phe Tyr Glu Lys Glu Ser Gly Gly Ala
1               5

<210> SEQ ID NO 276
<211> LENGTH: 9
<212> TYPE: PRT
<213> ORGANISM: Homo sapiens

<400> SEQUENCE: 276

Asp Tyr Arg Glu Asn His Asn Asn Asn
1               5

<210> SEQ ID NO 277
<211> LENGTH: 9
<212> TYPE: PRT
<213> ORGANISM: Homo sapiens

<400> SEQUENCE: 277

Ser Ile Leu Thr Gly Ser Phe Pro Leu
1               5

<210> SEQ ID NO 278
<211> LENGTH: 9
<212> TYPE: PRT
<213> ORGANISM: Homo sapiens

<400> SEQUENCE: 278

Gln Ala Met Gln Arg Pro Lys Gly Leu
1               5

<210> SEQ ID NO 279
<211> LENGTH: 9
<212> TYPE: PRT
<213> ORGANISM: Homo sapiens

<400> SEQUENCE: 279

Arg Pro Leu Trp His Glu Ser Asp Phe
1               5

<210> SEQ ID NO 280
<211> LENGTH: 9
<212> TYPE: PRT
```

<213> ORGANISM: Homo sapiens

<400> SEQUENCE: 280

Asn Asn Val Arg Gly Lys Arg Pro Leu
1               5

<210> SEQ ID NO 281
<211> LENGTH: 9
<212> TYPE: PRT
<213> ORGANISM: Homo sapiens

<400> SEQUENCE: 281

Met Ser Glu Ser Asp Ser Ser Ser Leu
1               5

<210> SEQ ID NO 282
<211> LENGTH: 9
<212> TYPE: PRT
<213> ORGANISM: Homo sapiens

<400> SEQUENCE: 282

Val Gly Glu Asn Ala Gln Pro Ile Leu
1               5

<210> SEQ ID NO 283
<211> LENGTH: 9
<212> TYPE: PRT
<213> ORGANISM: Homo sapiens

<400> SEQUENCE: 283

Leu Ser Glu Gly Ser Asp Ser Ser Leu
1               5

<210> SEQ ID NO 284
<211> LENGTH: 9
<212> TYPE: PRT
<213> ORGANISM: Homo sapiens

<400> SEQUENCE: 284

Glu Asn Asn Ile Gly Asn Arg Met Leu
1               5

<210> SEQ ID NO 285
<211> LENGTH: 9
<212> TYPE: PRT
<213> ORGANISM: Homo sapiens

<400> SEQUENCE: 285

Leu Val His Asp Leu Val Ser Ala Leu
1               5

<210> SEQ ID NO 286
<211> LENGTH: 9
<212> TYPE: PRT
<213> ORGANISM: Homo sapiens

<400> SEQUENCE: 286

His Ser Arg Ser Ile Ser Cys Pro Leu
1               5

<210> SEQ ID NO 287
<211> LENGTH: 9
<212> TYPE: PRT
<213> ORGANISM: Homo sapiens

<400> SEQUENCE: 287

His Pro Trp Glu Thr Gly His Cys Leu
1               5

<210> SEQ ID NO 288
<211> LENGTH: 9
<212> TYPE: PRT
<213> ORGANISM: Homo sapiens

<400> SEQUENCE: 288

His Ser Asp Ser Asp Asp Gln Met Leu
1               5

<210> SEQ ID NO 289
<211> LENGTH: 9
<212> TYPE: PRT
<213> ORGANISM: Homo sapiens

<400> SEQUENCE: 289

Arg Pro Lys Gly Leu Gly Leu Gly Phe
1               5

<210> SEQ ID NO 290
<211> LENGTH: 9
<212> TYPE: PRT
<213> ORGANISM: Homo sapiens

<400> SEQUENCE: 290

Met Gln Arg Pro Lys Gly Leu Gly Leu
1               5

<210> SEQ ID NO 291
<211> LENGTH: 9
<212> TYPE: PRT
<213> ORGANISM: Homo sapiens

<400> SEQUENCE: 291

Ala Ser Arg Gln Thr Ser Met His Leu
1               5

<210> SEQ ID NO 292
<211> LENGTH: 9
<212> TYPE: PRT
<213> ORGANISM: Homo sapiens

<400> SEQUENCE: 292

Met Gly Trp Thr Pro Gly Ser Gly Leu
1               5

<210> SEQ ID NO 293
<211> LENGTH: 9
<212> TYPE: PRT
<213> ORGANISM: Homo sapiens

<400> SEQUENCE: 293

Ser Leu Ser Ser Thr Asp Ala Gly Leu
1               5

<210> SEQ ID NO 294
<211> LENGTH: 9
<212> TYPE: PRT
<213> ORGANISM: Homo sapiens

<400> SEQUENCE: 294

Gln Thr Ser Met His Leu Gly Ser Leu
1               5

<210> SEQ ID NO 295
<211> LENGTH: 9
<212> TYPE: PRT
<213> ORGANISM: Homo sapiens

<400> SEQUENCE: 295

Lys Ile Ile Arg Gln Gly Pro Lys Ile
1               5

<210> SEQ ID NO 296
<211> LENGTH: 9
<212> TYPE: PRT
<213> ORGANISM: Homo sapiens

<400> SEQUENCE: 296

Val Gly Asn Lys Arg Met Val His Phe
1               5

<210> SEQ ID NO 297
<211> LENGTH: 9
<212> TYPE: PRT
<213> ORGANISM: Homo sapiens

<400> SEQUENCE: 297

Ser Ser Glu Gln Ala Arg Gly Gly Phe
1               5

<210> SEQ ID NO 298
<211> LENGTH: 9
<212> TYPE: PRT
<213> ORGANISM: Homo sapiens

<400> SEQUENCE: 298

Met Ala Val Asp Leu Pro Gln Asp Ile
1               5

<210> SEQ ID NO 299
<211> LENGTH: 10
<212> TYPE: PRT
<213> ORGANISM: Homo sapiens

<400> SEQUENCE: 299

Val Phe Glu Ser Ile Leu Thr Gly Ser Phe
1               5                   10

<210> SEQ ID NO 300
<211> LENGTH: 10
<212> TYPE: PRT
<213> ORGANISM: Homo sapiens

<400> SEQUENCE: 300

Arg Thr Glu His Asp Gln His Gln Leu Leu
1               5                   10

<210> SEQ ID NO 301
<211> LENGTH: 10
<212> TYPE: PRT
<213> ORGANISM: Homo sapiens

<400> SEQUENCE: 301

Gln Tyr Gln Glu Phe Thr Lys Asn Lys Val
1               5                   10

<210> SEQ ID NO 302

```
<211> LENGTH: 10
<212> TYPE: PRT
<213> ORGANISM: Homo sapiens

<400> SEQUENCE: 302

Ala Tyr Gln Tyr Gln Glu Phe Thr Lys Asn
1               5                   10

<210> SEQ ID NO 303
<211> LENGTH: 10
<212> TYPE: PRT
<213> ORGANISM: Homo sapiens

<400> SEQUENCE: 303

Gly Phe Val Gly Glu Asn Ala Gln Pro Ile
1               5                   10

<210> SEQ ID NO 304
<211> LENGTH: 10
<212> TYPE: PRT
<213> ORGANISM: Homo sapiens

<400> SEQUENCE: 304

Ser Tyr Asn Val His His Pro Trp Glu Thr
1               5                   10

<210> SEQ ID NO 305
<211> LENGTH: 10
<212> TYPE: PRT
<213> ORGANISM: Homo sapiens

<400> SEQUENCE: 305

Arg Gln Thr Ser Met His Leu Gly Ser Leu
1               5                   10

<210> SEQ ID NO 306
<211> LENGTH: 10
<212> TYPE: PRT
<213> ORGANISM: Homo sapiens

<400> SEQUENCE: 306

Arg Gly Phe Gln Ala Arg Leu Ser Arg Leu
1               5                   10

<210> SEQ ID NO 307
<211> LENGTH: 10
<212> TYPE: PRT
<213> ORGANISM: Homo sapiens

<400> SEQUENCE: 307

Phe Tyr Glu Lys Glu Ser Gly Gly Ala Cys
1               5                   10

<210> SEQ ID NO 308
<211> LENGTH: 10
<212> TYPE: PRT
<213> ORGANISM: Homo sapiens

<400> SEQUENCE: 308

Glu Leu Val His Asp Leu Val Ser Ala Leu
1               5                   10

<210> SEQ ID NO 309
<211> LENGTH: 10
<212> TYPE: PRT
```

<400> SEQUENCE: 309

Trp Trp Glu Lys Glu Asp Pro Thr Glu Leu
1               5                   10

<210> SEQ ID NO 310
<211> LENGTH: 10
<212> TYPE: PRT
<213> ORGANISM: Homo sapiens

<400> SEQUENCE: 310

Ser Ser Leu Ser Ser Thr Asp Ala Gly Leu
1               5                   10

<210> SEQ ID NO 311
<211> LENGTH: 10
<212> TYPE: PRT
<213> ORGANISM: Homo sapiens

<400> SEQUENCE: 311

Glu Ser Ile Leu Thr Gly Ser Phe Pro Leu
1               5                   10

<210> SEQ ID NO 312
<211> LENGTH: 10
<212> TYPE: PRT
<213> ORGANISM: Homo sapiens

<400> SEQUENCE: 312

Ala Met Gln Arg Pro Lys Gly Leu Gly Leu
1               5                   10

<210> SEQ ID NO 313
<211> LENGTH: 10
<212> TYPE: PRT
<213> ORGANISM: Homo sapiens

<400> SEQUENCE: 313

Asn Asn Asn Val Arg Gly Lys Arg Pro Leu
1               5                   10

<210> SEQ ID NO 314
<211> LENGTH: 10
<212> TYPE: PRT
<213> ORGANISM: Homo sapiens

<400> SEQUENCE: 314

Leu Met Ser Glu Ser Asp Ser Ser Ser Leu
1               5                   10

<210> SEQ ID NO 315
<211> LENGTH: 10
<212> TYPE: PRT
<213> ORGANISM: Homo sapiens

<400> SEQUENCE: 315

Val Pro Asp Pro Val Phe Glu Ser Ile Leu
1               5                   10

<210> SEQ ID NO 316
<211> LENGTH: 10
<212> TYPE: PRT
<213> ORGANISM: Homo sapiens

<400> SEQUENCE: 316

```
Phe Val Gly Glu Asn Ala Gln Pro Ile Leu
1               5                   10
```

<210> SEQ ID NO 317
<211> LENGTH: 10
<212> TYPE: PRT
<213> ORGANISM: Homo sapiens

<400> SEQUENCE: 317

```
Cys Leu Ser Glu Gly Ser Asp Ser Ser Leu
1               5                   10
```

<210> SEQ ID NO 318
<211> LENGTH: 10
<212> TYPE: PRT
<213> ORGANISM: Homo sapiens

<400> SEQUENCE: 318

```
Ala Val Asp Asn Val Gly Asn Arg Thr Leu
1               5                   10
```

<210> SEQ ID NO 319
<211> LENGTH: 10
<212> TYPE: PRT
<213> ORGANISM: Homo sapiens

<400> SEQUENCE: 319

```
Val Ala Lys Arg Arg Pro Ser Ser Asn Leu
1               5                   10
```

<210> SEQ ID NO 320
<211> LENGTH: 10
<212> TYPE: PRT
<213> ORGANISM: Homo sapiens

<400> SEQUENCE: 320

```
Ile Gln Ala Met Gln Arg Pro Lys Gly Leu
1               5                   10
```

<210> SEQ ID NO 321
<211> LENGTH: 10
<212> TYPE: PRT
<213> ORGANISM: Homo sapiens

<400> SEQUENCE: 321

```
Asn Met Gly Trp Thr Pro Gly Ser Gly Leu
1               5                   10
```

<210> SEQ ID NO 322
<211> LENGTH: 10
<212> TYPE: PRT
<213> ORGANISM: Homo sapiens

<400> SEQUENCE: 322

```
Thr Ala Ser Arg Gln Thr Ser Met His Leu
1               5                   10
```

<210> SEQ ID NO 323
<211> LENGTH: 10
<212> TYPE: PRT
<213> ORGANISM: Homo sapiens

<400> SEQUENCE: 323

```
Asn Val Pro Asp Pro Val Phe Glu Ser Ile
1               5                   10
```

<210> SEQ ID NO 324
<211> LENGTH: 10
<212> TYPE: PRT
<213> ORGANISM: Homo sapiens

<400> SEQUENCE: 324

Arg Met Ala Val Asp Leu Pro Gln Asp Ile
1               5                   10

<210> SEQ ID NO 325
<211> LENGTH: 10
<212> TYPE: PRT
<213> ORGANISM: Homo sapiens

<400> SEQUENCE: 325

Asn Ala Gln Pro Ile Leu Glu Asn Asn Ile
1               5                   10

<210> SEQ ID NO 326
<211> LENGTH: 10
<212> TYPE: PRT
<213> ORGANISM: Homo sapiens

<400> SEQUENCE: 326

Gln Gly Asp Asp Glu Gln Ser Asp Trp Phe
1               5                   10

<210> SEQ ID NO 327
<211> LENGTH: 10
<212> TYPE: PRT
<213> ORGANISM: Homo sapiens

<400> SEQUENCE: 327

Glu Ser Ser Glu Gln Ala Arg Gly Gly Phe
1               5                   10

<210> SEQ ID NO 328
<211> LENGTH: 10
<212> TYPE: PRT
<213> ORGANISM: Homo sapiens

<400> SEQUENCE: 328

Arg Leu His Gly Met Ser Ser Lys Asn Ile
1               5                   10

<210> SEQ ID NO 329
<211> LENGTH: 9
<212> TYPE: PRT
<213> ORGANISM: Homo sapiens

<400> SEQUENCE: 329

Ala Ser Arg Gln Thr Ser Met His Leu
1               5

<210> SEQ ID NO 330
<211> LENGTH: 9
<212> TYPE: PRT
<213> ORGANISM: Homo sapiens

<400> SEQUENCE: 330

His Pro Trp Glu Thr Gly His Cys Leu
1               5

<210> SEQ ID NO 331
<211> LENGTH: 9

```
<212> TYPE: PRT
<213> ORGANISM: Homo sapiens

<400> SEQUENCE: 331

Met Gln Arg Pro Lys Gly Leu Gly Leu
1               5

<210> SEQ ID NO 332
<211> LENGTH: 9
<212> TYPE: PRT
<213> ORGANISM: Homo sapiens

<400> SEQUENCE: 332

His Ser Arg Ser Ile Ser Cys Pro Leu
1               5

<210> SEQ ID NO 333
<211> LENGTH: 9
<212> TYPE: PRT
<213> ORGANISM: Homo sapiens

<400> SEQUENCE: 333

Gln Ala Met Gln Arg Pro Lys Gly Leu
1               5

<210> SEQ ID NO 334
<211> LENGTH: 9
<212> TYPE: PRT
<213> ORGANISM: Homo sapiens

<400> SEQUENCE: 334

Leu Val His Asp Leu Val Ser Ala Leu
1               5

<210> SEQ ID NO 335
<211> LENGTH: 9
<212> TYPE: PRT
<213> ORGANISM: Homo sapiens

<400> SEQUENCE: 335

Lys Val Lys Arg Met Ala Val Asp Leu
1               5

<210> SEQ ID NO 336
<211> LENGTH: 9
<212> TYPE: PRT
<213> ORGANISM: Homo sapiens

<400> SEQUENCE: 336

Ala Lys Arg Arg Pro Ser Ser Asn Leu
1               5

<210> SEQ ID NO 337
<211> LENGTH: 9
<212> TYPE: PRT
<213> ORGANISM: Homo sapiens

<400> SEQUENCE: 337

Ala Pro Leu Pro Gly Pro Thr Thr Ala
1               5

<210> SEQ ID NO 338
<211> LENGTH: 9
<212> TYPE: PRT
<213> ORGANISM: Homo sapiens
```

```
<400> SEQUENCE: 338

Met Gly Trp Thr Pro Gly Ser Gly Leu
 1               5

<210> SEQ ID NO 339
<211> LENGTH: 9
<212> TYPE: PRT
<213> ORGANISM: Homo sapiens

<400> SEQUENCE: 339

Ser Val Arg Thr Ala Ser Arg Gln Thr
 1               5

<210> SEQ ID NO 340
<211> LENGTH: 9
<212> TYPE: PRT
<213> ORGANISM: Homo sapiens

<400> SEQUENCE: 340

Gly Pro Lys Ile Gln Asp Glu Gly Val
 1               5

<210> SEQ ID NO 341
<211> LENGTH: 9
<212> TYPE: PRT
<213> ORGANISM: Homo sapiens

<400> SEQUENCE: 341

Lys Asn Lys Val Lys Lys Arg Lys Leu
 1               5

<210> SEQ ID NO 342
<211> LENGTH: 9
<212> TYPE: PRT
<213> ORGANISM: Homo sapiens

<400> SEQUENCE: 342

Asn Asn Val Arg Gly Lys Arg Pro Leu
 1               5

<210> SEQ ID NO 343
<211> LENGTH: 9
<212> TYPE: PRT
<213> ORGANISM: Homo sapiens

<400> SEQUENCE: 343

Lys Ile Gln Asp Glu Gly Val Val Leu
 1               5

<210> SEQ ID NO 344
<211> LENGTH: 9
<212> TYPE: PRT
<213> ORGANISM: Homo sapiens

<400> SEQUENCE: 344

Gln Thr Ser Met His Leu Gly Ser Leu
 1               5

<210> SEQ ID NO 345
<211> LENGTH: 9
<212> TYPE: PRT
<213> ORGANISM: Homo sapiens

<400> SEQUENCE: 345

Ser Leu Ser Ser Thr Asp Ala Gly Leu
```

<210> SEQ ID NO 346
<211> LENGTH: 9
<212> TYPE: PRT
<213> ORGANISM: Homo sapiens

<400> SEQUENCE: 346

Asp Pro Thr Glu Leu Asp Lys Asn Val
1               5

<210> SEQ ID NO 347
<211> LENGTH: 9
<212> TYPE: PRT
<213> ORGANISM: Homo sapiens

<400> SEQUENCE: 347

Ser Ile Leu Thr Gly Ser Phe Pro Leu
1               5

<210> SEQ ID NO 348
<211> LENGTH: 9
<212> TYPE: PRT
<213> ORGANISM: Homo sapiens

<400> SEQUENCE: 348

Gly Pro Val Gly Asn Lys Arg Met Val
1               5

<210> SEQ ID NO 349
<211> LENGTH: 9
<212> TYPE: PRT
<213> ORGANISM: Homo sapiens

<400> SEQUENCE: 349

Lys Gly Leu Gly Leu Gly Phe Pro Leu
1               5

<210> SEQ ID NO 350
<211> LENGTH: 9
<212> TYPE: PRT
<213> ORGANISM: Homo sapiens

<400> SEQUENCE: 350

Lys Arg Arg Arg Lys Ala Ala Pro Leu
1               5

<210> SEQ ID NO 351
<211> LENGTH: 9
<212> TYPE: PRT
<213> ORGANISM: Homo sapiens

<400> SEQUENCE: 351

Glu Asn Asn Ile Gly Asn Arg Met Leu
1               5

<210> SEQ ID NO 352
<211> LENGTH: 9
<212> TYPE: PRT
<213> ORGANISM: Homo sapiens

<400> SEQUENCE: 352

Ser Arg Arg Gly Phe Gln Ala Arg Leu
1               5

```
<210> SEQ ID NO 353
<211> LENGTH: 9
<212> TYPE: PRT
<213> ORGANISM: Homo sapiens

<400> SEQUENCE: 353

Gln Ala Arg Gly Gly Phe Ala Glu Thr
1               5

<210> SEQ ID NO 354
<211> LENGTH: 9
<212> TYPE: PRT
<213> ORGANISM: Homo sapiens

<400> SEQUENCE: 354

Val Pro Asp Pro Val Phe Glu Ser Ile
1               5

<210> SEQ ID NO 355
<211> LENGTH: 9
<212> TYPE: PRT
<213> ORGANISM: Homo sapiens

<400> SEQUENCE: 355

Asp Pro Val Phe Glu Ser Ile Leu Thr
1               5

<210> SEQ ID NO 356
<211> LENGTH: 9
<212> TYPE: PRT
<213> ORGANISM: Homo sapiens

<400> SEQUENCE: 356

His Pro Ser Arg Arg Gly Phe Gln Ala
1               5

<210> SEQ ID NO 357
<211> LENGTH: 9
<212> TYPE: PRT
<213> ORGANISM: Homo sapiens

<400> SEQUENCE: 357

Phe Val Gly Glu Asn Ala Gln Pro Ile
1               5

<210> SEQ ID NO 358
<211> LENGTH: 9
<212> TYPE: PRT
<213> ORGANISM: Homo sapiens

<400> SEQUENCE: 358

Phe Pro Leu Pro Lys Ser Thr Ser Ala
1               5

<210> SEQ ID NO 359
<211> LENGTH: 10
<212> TYPE: PRT
<213> ORGANISM: Homo sapiens

<400> SEQUENCE: 359

Gln Ala Arg Leu Ser Arg Leu His Gly Met
1               5                   10

<210> SEQ ID NO 360
<211> LENGTH: 10
<212> TYPE: PRT
```

<213> ORGANISM: Homo sapiens

<400> SEQUENCE: 360

Val Pro Asp Pro Val Phe Glu Ser Ile Leu
1               5                   10

<210> SEQ ID NO 361
<211> LENGTH: 10
<212> TYPE: PRT
<213> ORGANISM: Homo sapiens

<400> SEQUENCE: 361

Ile Pro Gly Pro Val Gly Asn Lys Arg Met
1               5                   10

<210> SEQ ID NO 362
<211> LENGTH: 10
<212> TYPE: PRT
<213> ORGANISM: Homo sapiens

<400> SEQUENCE: 362

Phe Val Gly Glu Asn Ala Gln Pro Ile Leu
1               5                   10

<210> SEQ ID NO 363
<211> LENGTH: 10
<212> TYPE: PRT
<213> ORGANISM: Homo sapiens

<400> SEQUENCE: 363

Ala Val Asp Asn Val Gly Asn Arg Thr Leu
1               5                   10

<210> SEQ ID NO 364
<211> LENGTH: 10
<212> TYPE: PRT
<213> ORGANISM: Homo sapiens

<400> SEQUENCE: 364

Val Ala Lys Arg Arg Pro Ser Ser Asn Leu
1               5                   10

<210> SEQ ID NO 365
<211> LENGTH: 10
<212> TYPE: PRT
<213> ORGANISM: Homo sapiens

<400> SEQUENCE: 365

Thr Ala Ser Arg Gln Thr Ser Met His Leu
1               5                   10

<210> SEQ ID NO 366
<211> LENGTH: 10
<212> TYPE: PRT
<213> ORGANISM: Homo sapiens

<400> SEQUENCE: 366

Ala Met Gln Arg Pro Lys Gly Leu Gly Leu
1               5                   10

<210> SEQ ID NO 367
<211> LENGTH: 10
<212> TYPE: PRT
<213> ORGANISM: Homo sapiens

<400> SEQUENCE: 367

Asn Met Gly Trp Thr Pro Gly Ser Gly Leu
1               5                   10

<210> SEQ ID NO 368
<211> LENGTH: 10
<212> TYPE: PRT
<213> ORGANISM: Homo sapiens

<400> SEQUENCE: 368

Leu Met Ser Glu Ser Asp Ser Ser Ser Leu
1               5                   10

<210> SEQ ID NO 369
<211> LENGTH: 10
<212> TYPE: PRT
<213> ORGANISM: Homo sapiens

<400> SEQUENCE: 369

Ile Gln Ala Met Gln Arg Pro Lys Gly Leu
1               5                   10

<210> SEQ ID NO 370
<211> LENGTH: 10
<212> TYPE: PRT
<213> ORGANISM: Homo sapiens

<400> SEQUENCE: 370

Pro Ser Arg Arg Gly Phe Gln Ala Arg Leu
1               5                   10

<210> SEQ ID NO 371
<211> LENGTH: 10
<212> TYPE: PRT
<213> ORGANISM: Homo sapiens

<400> SEQUENCE: 371

Leu Pro Gly Pro Thr Thr Ala Gly Phe Val
1               5                   10

<210> SEQ ID NO 372
<211> LENGTH: 10
<212> TYPE: PRT
<213> ORGANISM: Homo sapiens

<400> SEQUENCE: 372

Arg Pro Ser Ser Asn Leu Asn Asn Asn Val
1               5                   10

<210> SEQ ID NO 373
<211> LENGTH: 10
<212> TYPE: PRT
<213> ORGANISM: Homo sapiens

<400> SEQUENCE: 373

Asn Asn Asn Val Arg Gly Lys Arg Pro Leu
1               5                   10

<210> SEQ ID NO 374
<211> LENGTH: 10
<212> TYPE: PRT
<213> ORGANISM: Homo sapiens

<400> SEQUENCE: 374

Cys Leu Ser Glu Gly Ser Asp Ser Ser Leu
1               5                   10

<210> SEQ ID NO 375
<211> LENGTH: 10
<212> TYPE: PRT
<213> ORGANISM: Homo sapiens

<400> SEQUENCE: 375

Arg Gly Phe Gln Ala Arg Leu Ser Arg Leu
1               5                   10

<210> SEQ ID NO 376
<211> LENGTH: 10
<212> TYPE: PRT
<213> ORGANISM: Homo sapiens

<400> SEQUENCE: 376

Ser Ser Leu Ser Ser Thr Asp Ala Gly Leu
1               5                   10

<210> SEQ ID NO 377
<211> LENGTH: 10
<212> TYPE: PRT
<213> ORGANISM: Homo sapiens

<400> SEQUENCE: 377

Ile Lys Arg Arg Arg Lys Ala Ala Pro Leu
1               5                   10

<210> SEQ ID NO 378
<211> LENGTH: 10
<212> TYPE: PRT
<213> ORGANISM: Homo sapiens

<400> SEQUENCE: 378

Gly Pro Lys Ile Gln Asp Glu Gly Val Val
1               5                   10

<210> SEQ ID NO 379
<211> LENGTH: 10
<212> TYPE: PRT
<213> ORGANISM: Homo sapiens

<400> SEQUENCE: 379

Glu Ser Ile Leu Thr Gly Ser Phe Pro Leu
1               5                   10

<210> SEQ ID NO 380
<211> LENGTH: 10
<212> TYPE: PRT
<213> ORGANISM: Homo sapiens

<400> SEQUENCE: 380

Arg Gln Thr Ser Met His Leu Gly Ser Leu
1               5                   10

<210> SEQ ID NO 381
<211> LENGTH: 10
<212> TYPE: PRT
<213> ORGANISM: Homo sapiens

<400> SEQUENCE: 381

Glu Leu Val His Asp Leu Val Ser Ala Leu
1               5                   10

<210> SEQ ID NO 382

```
<211> LENGTH: 10
<212> TYPE: PRT
<213> ORGANISM: Homo sapiens

<400> SEQUENCE: 382

Leu Pro Gln Asp Ile Ser Asn Lys Arg Thr
1               5                   10

<210> SEQ ID NO 383
<211> LENGTH: 10
<212> TYPE: PRT
<213> ORGANISM: Homo sapiens

<400> SEQUENCE: 383

Arg Pro Leu Trp His Glu Ser Asp Phe Ala
1               5                   10

<210> SEQ ID NO 384
<211> LENGTH: 10
<212> TYPE: PRT
<213> ORGANISM: Homo sapiens

<400> SEQUENCE: 384

Val Pro Trp Trp Glu Lys Glu Asp Pro Thr
1               5                   10

<210> SEQ ID NO 385
<211> LENGTH: 10
<212> TYPE: PRT
<213> ORGANISM: Homo sapiens

<400> SEQUENCE: 385

Leu Pro Lys Ser Thr Ser Ala Thr Thr Thr
1               5                   10

<210> SEQ ID NO 386
<211> LENGTH: 10
<212> TYPE: PRT
<213> ORGANISM: Homo sapiens

<400> SEQUENCE: 386

Asn Val Pro Asp Pro Val Phe Glu Ser Ile
1               5                   10

<210> SEQ ID NO 387
<211> LENGTH: 10
<212> TYPE: PRT
<213> ORGANISM: Homo sapiens

<400> SEQUENCE: 387

Arg Gly Arg Lys Arg Arg Ser Tyr Asn Val
1               5                   10

<210> SEQ ID NO 388
<211> LENGTH: 10
<212> TYPE: PRT
<213> ORGANISM: Homo sapiens

<400> SEQUENCE: 388

Phe Pro Leu Pro Lys Ser Thr Ser Ala Thr
1               5                   10

<210> SEQ ID NO 389
<211> LENGTH: 9
<212> TYPE: PRT
<213> ORGANISM: Homo sapiens
```

<400> SEQUENCE: 389

Arg Pro Lys Gly Leu Gly Leu Gly Phe
 1               5

<210> SEQ ID NO 390
<211> LENGTH: 9
<212> TYPE: PRT
<213> ORGANISM: Homo sapiens

<400> SEQUENCE: 390

His Pro Trp Glu Thr Gly His Cys Leu
 1               5

<210> SEQ ID NO 391
<211> LENGTH: 9
<212> TYPE: PRT
<213> ORGANISM: Homo sapiens

<400> SEQUENCE: 391

Arg Pro Leu Trp His Glu Ser Asp Phe
 1               5

<210> SEQ ID NO 392
<211> LENGTH: 9
<212> TYPE: PRT
<213> ORGANISM: Homo sapiens

<400> SEQUENCE: 392

Leu Pro Gly Pro Thr Thr Ala Gly Phe
 1               5

<210> SEQ ID NO 393
<211> LENGTH: 9
<212> TYPE: PRT
<213> ORGANISM: Homo sapiens

<400> SEQUENCE: 393

Lys Ser Gly Gly Thr Pro Thr Ser Met
 1               5

<210> SEQ ID NO 394
<211> LENGTH: 9
<212> TYPE: PRT
<213> ORGANISM: Homo sapiens

<400> SEQUENCE: 394

Ala Ser Arg Gln Thr Ser Met His Leu
 1               5

<210> SEQ ID NO 395
<211> LENGTH: 9
<212> TYPE: PRT
<213> ORGANISM: Homo sapiens

<400> SEQUENCE: 395

His Ser Arg Ser Ile Ser Cys Pro Leu
 1               5

<210> SEQ ID NO 396
<211> LENGTH: 9
<212> TYPE: PRT
<213> ORGANISM: Homo sapiens

<400> SEQUENCE: 396

```
Gly Pro Lys Ile Gln Asp Glu Gly Val
1               5

<210> SEQ ID NO 397
<211> LENGTH: 9
<212> TYPE: PRT
<213> ORGANISM: Homo sapiens

<400> SEQUENCE: 397

Asp Pro Thr Glu Leu Asp Lys Asn Val
1               5

<210> SEQ ID NO 398
<211> LENGTH: 9
<212> TYPE: PRT
<213> ORGANISM: Homo sapiens

<400> SEQUENCE: 398

Leu Ser Ser Thr Asp Ala Gly Leu Phe
1               5

<210> SEQ ID NO 399
<211> LENGTH: 9
<212> TYPE: PRT
<213> ORGANISM: Homo sapiens

<400> SEQUENCE: 399

Lys Val Lys Arg Met Ala Val Asp Leu
1               5

<210> SEQ ID NO 400
<211> LENGTH: 9
<212> TYPE: PRT
<213> ORGANISM: Homo sapiens

<400> SEQUENCE: 400

Glu Gln Lys Val Ser Asp Glu Leu Met
1               5

<210> SEQ ID NO 401
<211> LENGTH: 9
<212> TYPE: PRT
<213> ORGANISM: Homo sapiens

<400> SEQUENCE: 401

Leu Pro Lys Ser Thr Ser Ala Thr Thr
1               5

<210> SEQ ID NO 402
<211> LENGTH: 9
<212> TYPE: PRT
<213> ORGANISM: Homo sapiens

<400> SEQUENCE: 402

Lys Ile Gln Asp Glu Gly Val Val Leu
1               5

<210> SEQ ID NO 403
<211> LENGTH: 9
<212> TYPE: PRT
<213> ORGANISM: Homo sapiens

<400> SEQUENCE: 403

Lys Asn Lys Val Lys Arg Lys Leu
1               5
```

```
<210> SEQ ID NO 404
<211> LENGTH: 9
<212> TYPE: PRT
<213> ORGANISM: Homo sapiens

<400> SEQUENCE: 404

Met Ser His Pro Ser Arg Arg Gly Phe
1               5

<210> SEQ ID NO 405
<211> LENGTH: 9
<212> TYPE: PRT
<213> ORGANISM: Homo sapiens

<400> SEQUENCE: 405

Asp Ser His His His Asp His Trp Phe
1               5

<210> SEQ ID NO 406
<211> LENGTH: 9
<212> TYPE: PRT
<213> ORGANISM: Homo sapiens

<400> SEQUENCE: 406

Arg Ser Tyr Asn Val His His Pro Trp
1               5

<210> SEQ ID NO 407
<211> LENGTH: 9
<212> TYPE: PRT
<213> ORGANISM: Homo sapiens

<400> SEQUENCE: 407

Arg Pro Ser Ser Asn Leu Asn Asn Asn
1               5

<210> SEQ ID NO 408
<211> LENGTH: 9
<212> TYPE: PRT
<213> ORGANISM: Homo sapiens

<400> SEQUENCE: 408

Gly Ile Ser Glu Pro Ile Gln Ala Met
1               5

<210> SEQ ID NO 409
<211> LENGTH: 9
<212> TYPE: PRT
<213> ORGANISM: Homo sapiens

<400> SEQUENCE: 409

Gly Pro Val Gly Asn Lys Arg Met Val
1               5

<210> SEQ ID NO 410
<211> LENGTH: 9
<212> TYPE: PRT
<213> ORGANISM: Homo sapiens

<400> SEQUENCE: 410

Arg Thr Ala Ser Arg Gln Thr Ser Met
1               5

<210> SEQ ID NO 411
<211> LENGTH: 9
```

```
<212> TYPE: PRT
<213> ORGANISM: Homo sapiens

<400> SEQUENCE: 411

Asp Pro Val Phe Glu Ser Ile Leu Thr
1               5

<210> SEQ ID NO 412
<211> LENGTH: 9
<212> TYPE: PRT
<213> ORGANISM: Homo sapiens

<400> SEQUENCE: 412

Met Gln Arg Pro Lys Gly Leu Gly Leu
1               5

<210> SEQ ID NO 413
<211> LENGTH: 9
<212> TYPE: PRT
<213> ORGANISM: Homo sapiens

<400> SEQUENCE: 413

Glu Pro Ser Lys Asp Tyr Arg Glu Asn
1               5

<210> SEQ ID NO 414
<211> LENGTH: 9
<212> TYPE: PRT
<213> ORGANISM: Homo sapiens

<400> SEQUENCE: 414

Gln Ala Met Gln Arg Pro Lys Gly Leu
1               5

<210> SEQ ID NO 415
<211> LENGTH: 9
<212> TYPE: PRT
<213> ORGANISM: Homo sapiens

<400> SEQUENCE: 415

Met Ala Val Asp Leu Pro Gln Asp Ile
1               5

<210> SEQ ID NO 416
<211> LENGTH: 9
<212> TYPE: PRT
<213> ORGANISM: Homo sapiens

<400> SEQUENCE: 416

Lys Val Lys Lys Arg Lys Leu Lys Ile
1               5

<210> SEQ ID NO 417
<211> LENGTH: 9
<212> TYPE: PRT
<213> ORGANISM: Homo sapiens

<400> SEQUENCE: 417

Val Pro Asp Pro Val Phe Glu Ser Ile
1               5

<210> SEQ ID NO 418
<211> LENGTH: 9
<212> TYPE: PRT
<213> ORGANISM: Homo sapiens
```

```
<400> SEQUENCE: 418

His Ser Asp Ser Asp Gln Met Leu
 1               5

<210> SEQ ID NO 419
<211> LENGTH: 10
<212> TYPE: PRT
<213> ORGANISM: Homo sapiens

<400> SEQUENCE: 419

Ile Pro Gly Pro Val Gly Asn Lys Arg Met
 1               5                  10

<210> SEQ ID NO 420
<211> LENGTH: 10
<212> TYPE: PRT
<213> ORGANISM: Homo sapiens

<400> SEQUENCE: 420

Ser Ser Leu Glu Glu Pro Ser Lys Asp Tyr
 1               5                  10

<210> SEQ ID NO 421
<211> LENGTH: 10
<212> TYPE: PRT
<213> ORGANISM: Homo sapiens

<400> SEQUENCE: 421

Gly Pro Lys Ile Gln Asp Glu Gly Val Val
 1               5                  10

<210> SEQ ID NO 422
<211> LENGTH: 10
<212> TYPE: PRT
<213> ORGANISM: Homo sapiens

<400> SEQUENCE: 422

Gln Ala Arg Leu Ser Arg Leu His Gly Met
 1               5                  10

<210> SEQ ID NO 423
<211> LENGTH: 10
<212> TYPE: PRT
<213> ORGANISM: Homo sapiens

<400> SEQUENCE: 423

Glu Ser Ser Glu Gln Ala Arg Gly Gly Phe
 1               5                  10

<210> SEQ ID NO 424
<211> LENGTH: 10
<212> TYPE: PRT
<213> ORGANISM: Homo sapiens

<400> SEQUENCE: 424

Val Ala Lys Arg Arg Pro Ser Ser Asn Leu
 1               5                  10

<210> SEQ ID NO 425
<211> LENGTH: 10
<212> TYPE: PRT
<213> ORGANISM: Homo sapiens

<400> SEQUENCE: 425

Arg Pro Ser Ser Asn Leu Asn Asn Asn Val
```

```
                1               5                  10
```

<210> SEQ ID NO 426
<211> LENGTH: 10
<212> TYPE: PRT
<213> ORGANISM: Homo sapiens

<400> SEQUENCE: 426

```
Arg Pro Leu Trp His Glu Ser Asp Phe Ala
 1               5                  10
```

<210> SEQ ID NO 427
<211> LENGTH: 10
<212> TYPE: PRT
<213> ORGANISM: Homo sapiens

<400> SEQUENCE: 427

```
Leu Pro Lys Ser Thr Ser Ala Thr Thr Thr
 1               5                  10
```

<210> SEQ ID NO 428
<211> LENGTH: 10
<212> TYPE: PRT
<213> ORGANISM: Homo sapiens

<400> SEQUENCE: 428

```
Val Pro Asp Pro Val Phe Glu Ser Ile Leu
 1               5                  10
```

<210> SEQ ID NO 429
<211> LENGTH: 10
<212> TYPE: PRT
<213> ORGANISM: Homo sapiens

<400> SEQUENCE: 429

```
Glu Ser Ile Leu Thr Gly Ser Phe Pro Leu
 1               5                  10
```

<210> SEQ ID NO 430
<211> LENGTH: 10
<212> TYPE: PRT
<213> ORGANISM: Homo sapiens

<400> SEQUENCE: 430

```
Ser Ser Leu Ser Ser Thr Asp Ala Gly Leu
 1               5                  10
```

<210> SEQ ID NO 431
<211> LENGTH: 10
<212> TYPE: PRT
<213> ORGANISM: Homo sapiens

<400> SEQUENCE: 431

```
Lys Gly Ile Ser Glu Pro Ile Gln Ala Met
 1               5                  10
```

<210> SEQ ID NO 432
<211> LENGTH: 10
<212> TYPE: PRT
<213> ORGANISM: Homo sapiens

<400> SEQUENCE: 432

```
His Pro Trp Glu Thr Gly His Cys Leu Ser
 1               5                  10
```

```
<210> SEQ ID NO 433
<211> LENGTH: 10
<212> TYPE: PRT
<213> ORGANISM: Homo sapiens

<400> SEQUENCE: 433

Leu Pro Gln Asp Ile Ser Asn Lys Arg Thr
 1               5                  10

<210> SEQ ID NO 434
<211> LENGTH: 10
<212> TYPE: PRT
<213> ORGANISM: Homo sapiens

<400> SEQUENCE: 434

Leu Pro Gly Pro Thr Thr Ala Gly Phe Val
 1               5                  10

<210> SEQ ID NO 435
<211> LENGTH: 10
<212> TYPE: PRT
<213> ORGANISM: Homo sapiens

<400> SEQUENCE: 435

Ser Pro Asp Ser His His Asp His Trp
 1               5                  10

<210> SEQ ID NO 436
<211> LENGTH: 10
<212> TYPE: PRT
<213> ORGANISM: Homo sapiens

<400> SEQUENCE: 436

Leu Met Ser Glu Ser Asp Ser Ser Ser Leu
 1               5                  10

<210> SEQ ID NO 437
<211> LENGTH: 10
<212> TYPE: PRT
<213> ORGANISM: Homo sapiens

<400> SEQUENCE: 437

Arg Gln Gly Asp Asp Glu Gln Ser Asp Trp
 1               5                  10

<210> SEQ ID NO 438
<211> LENGTH: 10
<212> TYPE: PRT
<213> ORGANISM: Homo sapiens

<400> SEQUENCE: 438

Thr Ala Ser Arg Gln Thr Ser Met His Leu
 1               5                  10

<210> SEQ ID NO 439
<211> LENGTH: 10
<212> TYPE: PRT
<213> ORGANISM: Homo sapiens

<400> SEQUENCE: 439

Lys Val Lys Lys Arg Lys Leu Lys Ile Ile
 1               5                  10

<210> SEQ ID NO 440
<211> LENGTH: 10
<212> TYPE: PRT
```

<213> ORGANISM: Homo sapiens

<400> SEQUENCE: 440

Asn Ile Gly Asn Arg Met Leu Gln Asn Met
1               5                   10

<210> SEQ ID NO 441
<211> LENGTH: 10
<212> TYPE: PRT
<213> ORGANISM: Homo sapiens

<400> SEQUENCE: 441

Arg Gln Thr Ser Met His Leu Gly Ser Leu
1               5                   10

<210> SEQ ID NO 442
<211> LENGTH: 10
<212> TYPE: PRT
<213> ORGANISM: Homo sapiens

<400> SEQUENCE: 442

Ser Ile Leu Thr Gly Ser Phe Pro Leu Met
1               5                   10

<210> SEQ ID NO 443
<211> LENGTH: 10
<212> TYPE: PRT
<213> ORGANISM: Homo sapiens

<400> SEQUENCE: 443

Lys Ser Gly Gly Thr Pro Thr Ser Met Val
1               5                   10

<210> SEQ ID NO 444
<211> LENGTH: 10
<212> TYPE: PRT
<213> ORGANISM: Homo sapiens

<400> SEQUENCE: 444

Phe Val Gly Glu Asn Ala Gln Pro Ile Leu
1               5                   10

<210> SEQ ID NO 445
<211> LENGTH: 10
<212> TYPE: PRT
<213> ORGANISM: Homo sapiens

<400> SEQUENCE: 445

Glu Thr Asn Gln Thr Asn Lys Asp Lys Met
1               5                   10

<210> SEQ ID NO 446
<211> LENGTH: 10
<212> TYPE: PRT
<213> ORGANISM: Homo sapiens

<400> SEQUENCE: 446

Cys Leu Ser Glu Gly Ser Asp Ser Ser Leu
1               5                   10

<210> SEQ ID NO 447
<211> LENGTH: 10
<212> TYPE: PRT
<213> ORGANISM: Homo sapiens

<400> SEQUENCE: 447

Phe Pro Leu Pro Lys Ser Thr Ser Ala Thr
 1               5                  10

<210> SEQ ID NO 448
<211> LENGTH: 10
<212> TYPE: PRT
<213> ORGANISM: Homo sapiens

<400> SEQUENCE: 448

Arg Gly Phe Gln Ala Arg Leu Ser Arg Leu
 1               5                  10

<210> SEQ ID NO 449
<211> LENGTH: 4
<212> TYPE: PRT
<213> ORGANISM: Homo sapiens

<400> SEQUENCE: 449

Arg Lys Arg Arg
 1

<210> SEQ ID NO 450
<211> LENGTH: 4
<212> TYPE: PRT
<213> ORGANISM: Homo sapiens

<400> SEQUENCE: 450

Lys Arg Arg Pro
 1

<210> SEQ ID NO 451
<211> LENGTH: 6
<212> TYPE: PRT
<213> ORGANISM: Homo sapiens

<400> SEQUENCE: 451

Arg Arg Arg Arg Arg Lys
 1               5

<210> SEQ ID NO 452
<211> LENGTH: 4
<212> TYPE: PRT
<213> ORGANISM: Homo sapiens

<400> SEQUENCE: 452

Lys Lys Arg Lys
 1

<210> SEQ ID NO 453
<211> LENGTH: 4
<212> TYPE: PRT
<213> ORGANISM: Homo sapiens

<400> SEQUENCE: 453

Asn Arg Thr Leu
 1

<210> SEQ ID NO 454
<211> LENGTH: 4
<212> TYPE: PRT
<213> ORGANISM: Homo sapiens

<400> SEQUENCE: 454

Asn Gln Thr Asn
 1

<210> SEQ ID NO 455
<211> LENGTH: 4
<212> TYPE: PRT
<213> ORGANISM: Homo sapiens

<400> SEQUENCE: 455

Asn Cys Ser Val
1

<210> SEQ ID NO 456
<211> LENGTH: 4
<212> TYPE: PRT
<213> ORGANISM: Homo sapiens

<400> SEQUENCE: 456

Lys Arg Arg Ser
1

<210> SEQ ID NO 457
<211> LENGTH: 4
<212> TYPE: PRT
<213> ORGANISM: Homo sapiens

<400> SEQUENCE: 457

Arg Arg Pro Ser
1

<210> SEQ ID NO 458
<211> LENGTH: 3
<212> TYPE: PRT
<213> ORGANISM: Homo sapiens

<400> SEQUENCE: 458

Thr Leu Arg
1

<210> SEQ ID NO 459
<211> LENGTH: 3
<212> TYPE: PRT
<213> ORGANISM: Homo sapiens

<400> SEQUENCE: 459

Ser Asn Lys
1

<210> SEQ ID NO 460
<211> LENGTH: 3
<212> TYPE: PRT
<213> ORGANISM: Homo sapiens

<400> SEQUENCE: 460

Ser Asp Arg
1

<210> SEQ ID NO 461
<211> LENGTH: 3
<212> TYPE: PRT
<213> ORGANISM: Homo sapiens

<400> SEQUENCE: 461

Thr Asn Lys
1

<210> SEQ ID NO 462

```
<211> LENGTH: 3
<212> TYPE: PRT
<213> ORGANISM: Homo sapiens

<400> SEQUENCE: 462

Ser Arg Arg
 1

<210> SEQ ID NO 463
<211> LENGTH: 3
<212> TYPE: PRT
<213> ORGANISM: Homo sapiens

<400> SEQUENCE: 463

Ser Ser Lys
 1

<210> SEQ ID NO 464
<211> LENGTH: 3
<212> TYPE: PRT
<213> ORGANISM: Homo sapiens

<400> SEQUENCE: 464

Ser Val Arg
 1

<210> SEQ ID NO 465
<211> LENGTH: 4
<212> TYPE: PRT
<213> ORGANISM: Homo sapiens

<400> SEQUENCE: 465

Ser Ala Leu Glu
 1

<210> SEQ ID NO 466
<211> LENGTH: 4
<212> TYPE: PRT
<213> ORGANISM: Homo sapiens

<400> SEQUENCE: 466

Ser Ser Leu Glu
 1

<210> SEQ ID NO 467
<211> LENGTH: 4
<212> TYPE: PRT
<213> ORGANISM: Homo sapiens

<400> SEQUENCE: 467

Ser Leu Glu Glu
 1

<210> SEQ ID NO 468
<211> LENGTH: 4
<212> TYPE: PRT
<213> ORGANISM: Homo sapiens

<400> SEQUENCE: 468

Ser Asp Ser Asp
 1

<210> SEQ ID NO 469
<211> LENGTH: 4
<212> TYPE: PRT
<213> ORGANISM: Homo sapiens
```

<400> SEQUENCE: 469

Thr Asn Lys Asp
 1

<210> SEQ ID NO 470
<211> LENGTH: 4
<212> TYPE: PRT
<213> ORGANISM: Homo sapiens

<400> SEQUENCE: 470

Ser Glu Ser Asp
 1

<210> SEQ ID NO 471
<211> LENGTH: 4
<212> TYPE: PRT
<213> ORGANISM: Homo sapiens

<400> SEQUENCE: 471

Ser Ser Thr Asp
 1

<210> SEQ ID NO 472
<211> LENGTH: 4
<212> TYPE: PRT
<213> ORGANISM: Homo sapiens

<400> SEQUENCE: 472

Thr Asn Asp Glu
 1

<210> SEQ ID NO 473
<211> LENGTH: 4
<212> TYPE: PRT
<213> ORGANISM: Homo sapiens

<400> SEQUENCE: 473

Thr Glu Leu Asp
 1

<210> SEQ ID NO 474
<211> LENGTH: 4
<212> TYPE: PRT
<213> ORGANISM: Homo sapiens

<400> SEQUENCE: 474

Thr Glu His Asp
 1

<210> SEQ ID NO 475
<211> LENGTH: 6
<212> TYPE: PRT
<213> ORGANISM: Homo sapiens

<400> SEQUENCE: 475

Gly Ser Asp Ser Ser Leu
 1               5

<210> SEQ ID NO 476
<211> LENGTH: 6
<212> TYPE: PRT
<213> ORGANISM: Homo sapiens

<400> SEQUENCE: 476

```
Gly Leu Phe Thr Asn Asp
1               5

<210> SEQ ID NO 477
<211> LENGTH: 6
<212> TYPE: PRT
<213> ORGANISM: Homo sapiens

<400> SEQUENCE: 477

Gly Gly Ala Cys Gly Ile
1               5

<210> SEQ ID NO 478
<211> LENGTH: 6
<212> TYPE: PRT
<213> ORGANISM: Homo sapiens

<400> SEQUENCE: 478

Gly Gly Thr Pro Thr Ser
1               5

<210> SEQ ID NO 479
<211> LENGTH: 6
<212> TYPE: PRT
<213> ORGANISM: Homo sapiens

<400> SEQUENCE: 479

Gly Thr Pro Thr Ser Met
1               5

<210> SEQ ID NO 480
<211> LENGTH: 6
<212> TYPE: PRT
<213> ORGANISM: Homo sapiens

<400> SEQUENCE: 480

Gly Ser Leu Cys Thr Gly
1               5

<210> SEQ ID NO 481
<211> LENGTH: 6
<212> TYPE: PRT
<213> ORGANISM: Homo sapiens

<400> SEQUENCE: 481

Gly Ser Gly Leu Gly Arg
1               5

<210> SEQ ID NO 482
<211> LENGTH: 6
<212> TYPE: PRT
<213> ORGANISM: Homo sapiens

<400> SEQUENCE: 482

Gly Leu Gly Leu Gly Phe
1               5

<210> SEQ ID NO 483
<211> LENGTH: 4
```

```
<212> TYPE: PRT
<213> ORGANISM: Homo sapiens

<400> SEQUENCE: 483

Arg Gly Arg Lys
 1

<210> SEQ ID NO 484
<211> LENGTH: 4
<212> TYPE: PRT
<213> ORGANISM: Homo sapiens

<400> SEQUENCE: 484

Arg Gly Lys Arg
 1
```